United States Patent
Echigo

(10) Patent No.: US 10,723,690 B2
(45) Date of Patent: Jul. 28, 2020

(54) (METH)ACRYLOYL COMPOUND AND METHOD FOR PRODUCING SAME

(71) Applicant: Mitsubishi Gas Chemical Company, Inc., Tokyo (JP)

(72) Inventor: Masatoshi Echigo, Tokyo (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 81 days.

(21) Appl. No.: 15/746,703

(22) PCT Filed: Jul. 21, 2016

(86) PCT No.: PCT/JP2016/071448
§ 371 (c)(1),
(2) Date: Jan. 22, 2018

(87) PCT Pub. No.: WO2017/014285
PCT Pub. Date: Jan. 26, 2017

(65) Prior Publication Data
US 2018/0210341 A1    Jul. 26, 2018

(30) Foreign Application Priority Data
Jul. 23, 2015   (JP) ................................ 2015-145643

(51) Int. Cl.
| | | |
|---|---|---|
| *C07C 69/017* | (2006.01) | |
| *C07C 69/14* | (2006.01) | |
| *C07C 69/54* | (2006.01) | |
| *G03F 7/023* | (2006.01) | |
| *G03F 7/30* | (2006.01) | |

(Continued)

(52) U.S. Cl.
CPC ............ *C07C 69/017* (2013.01); *C07B 61/00* (2013.01); *C07C 67/14* (2013.01); *C07C 69/533* (2013.01); *C07C 69/54* (2013.01); *C07C 69/587* (2013.01); *C07D 311/82* (2013.01); *C07D 311/92* (2013.01); *C08F 20/30* (2013.01); *G03F 7/023* (2013.01); *G03F 7/0226* (2013.01); *G03F 7/039* (2013.01); *G03F 7/0758* (2013.01); *G03F 7/094* (2013.01)

(58) Field of Classification Search
CPC ..... C07C 69/533; C07C 69/587; C07C 69/54; C07C 69/017; G03F 7/0226; G03F 7/023
USPC .............................. 560/205, 218, 220, 221 Q
See application file for complete search history.

(56) References Cited

U.S. PATENT DOCUMENTS

| | | | | |
|---|---|---|---|---|
| 4,320,144 A | * | 3/1982 | Resnick .................. | A01N 37/02 514/548 |
| 4,387,204 A | | 6/1983 | Zahir et al. | |

(Continued)

FOREIGN PATENT DOCUMENTS

| | | |
|---|---|---|
| EP | 0038300 A1 | 10/1981 |
| EP | 2878591 A1 | 6/2015 |

(Continued)

OTHER PUBLICATIONS

Costantino, Andrea R. et al., "Efficient Routes to Racemic and Enantiomerically Pure (S)-BINOL Diesters," Synthetic Communications, 2013, vol. 43, No. 23, pp. 3192-3202.

(Continued)

*Primary Examiner* — John S Chu
(74) *Attorney, Agent, or Firm* — Fitch, Even, Tabin & Flannery LLP

(57) ABSTRACT

A (meth)acryloyl compound represented by the following formula (A):

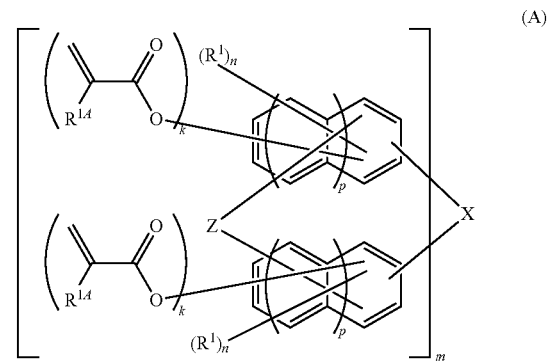

wherein X is a 2m-valent group having 1 to 60 carbon atoms or a single bond; each Z is independently an oxygen atom, a sulfur atom, or not a crosslink; each $R^1$ is independently a linear, branched, or cyclic alkyl group having 1 to 30 carbon atoms, an aryl group having 6 to 30 carbon atoms and optionally having a substituent, an alkenyl group having 2 to 30 carbon atoms and optionally having a substituent, an alkoxy group having 1 to 30 carbon atoms and optionally having a substituent, a halogen atom, a nitro group, an amino group, a carboxylic acid group, a thiol group, a hydroxy group, or a group in which a hydrogen atom of a hydroxy group is replaced with a vinylphenylmethyl group, wherein the alkyl group, the aryl group, the alkenyl group, or the alkoxy group optionally contains an ether bond, a ketone bond, or an ester bond; each $R^{1A}$ is independently a methyl group or a hydrogen atom; each k is independently an integer of 0 to 2, provided that all of the k moieties are not 0 at the same time; m is an integer of 1 to 3; each n is independently an integer of 0 to 5; and each p is independently 0 or 1.

10 Claims, No Drawings

(51) Int. Cl.

| | |
|---|---|
| *C07C 67/14* | (2006.01) |
| *C08F 20/30* | (2006.01) |
| *C07D 311/82* | (2006.01) |
| *C07B 61/00* | (2006.01) |
| *C07D 311/92* | (2006.01) |
| *G03F 7/022* | (2006.01) |
| *C07C 69/587* | (2006.01) |
| *C07C 69/533* | (2006.01) |
| *G03F 7/039* | (2006.01) |
| *G03F 7/075* | (2006.01) |
| *G03F 7/09* | (2006.01) |

(56) References Cited

U.S. PATENT DOCUMENTS

| | | | | |
|---|---|---|---|---|
| 4,439,291 | A * | 3/1984 | Irving | C08F 20/40 430/287.1 |
| 2011/0244218 | A1* | 10/2011 | Suzuki | C08F 2/44 428/323 |
| 2014/0329178 | A1 | 11/2014 | Echigo et al. | |
| 2015/0102259 | A1 | 4/2015 | Gotoh et al. | |
| 2015/0368224 | A1 | 12/2015 | Echigo | |
| 2016/0046551 | A1 | 2/2016 | Shiota et al. | |
| 2016/0046552 | A1 | 2/2016 | Shiota et al. | |

FOREIGN PATENT DOCUMENTS

| | | |
|---|---|---|
| JP | S62-191850 A | 8/1987 |
| JP | 1997-263560 A | 10/1997 |
| JP | 1999-043524 A | 2/1999 |
| JP | 2002-284740 A | 10/2002 |
| JP | 2010-138393 A | 6/2010 |
| JP | 2015-078282 A | 4/2015 |
| JP | 2015-087715 A | 5/2015 |
| JP | 2015-174877 A | 10/2015 |
| WO | 2006/132139 A1 | 12/2006 |
| WO | 2013/073582 A1 | 5/2013 |
| WO | 2014/123005 A1 | 8/2014 |
| WO | 2014/157675 A1 | 10/2014 |
| WO | 2014/157676 A1 | 10/2014 |

OTHER PUBLICATIONS

Hagiwara, Hisahiro et al., "Annulation by Sequential Double Michael Reaction: Synthesis of Decalones and Its Application to the Syntheses of ϵ-Cadinere, Khusitone and Khusilal," Journal of the Chemical Society Perkin Transactions 1, 993, No. 18, pp. 2173-2184.

Kokado, Kenta et al., "Rigidity-induced emission enhancement of network polymers crosslinked by tetraphenylethene derivatives," Journal of Materials Chemistry C, 2015, vol. 3, No. 33, pp. 8504-8509.

Shibayev, V.P. et al., "Liquid Crystalline Polymers," Polymer Science U.S.S.R., 1977, vol. 19, No. 5, pp. 1065-1122.

Yoon, Hyuk et al., "Effect of acrylate monomers on the diffraction behavior of photopolymers fabricated with cellulose ester polymer binder," Optical Materials, 2005, vol. 27, No. 6, pp. 1190-1196.

Jedrzej Kielkiewicz, Polimerzation of acrylates on matrixes of β-naphthol derivatives, Polimery, 1984, 29(6), 216-219.

International Search Report for PCT/JP2016/071448 dated Oct. 18, 2016; English translation submitted herewith (7 pages).

\* cited by examiner

(METH)ACRYLOYL COMPOUND AND METHOD FOR PRODUCING SAME

CROSS-REFERENCE TO RELATED APPLICATIONS

This application is a U.S. national phase application filed under 35 U.S.C. § 371 of International Application PCT/JP2016/071448, filed on Jul. 21, 2016, designating the United States, which claims priority from Japanese Application Number 2015-145643, filed Jul. 23, 2015.

FIELD OF THE INVENTION

The present invention relates to a novel (meth)acryloyl compound and a method for producing the same.

BACKGROUND OF THE INVENTION

For photoresist components, resin raw materials intended for materials for electric or electronic components or structural materials, or resin curing agents, (meth)acryloyl compounds having a bisphenol skeleton are known to be useful from the viewpoint of various properties (such as optical properties, heat resistance, water resistance, moisture resistance, chemical resistance, electrical properties, mechanical properties, and dimensional stability) (see Patent Literatures 1 to 5).

Various materials have also been proposed for optical component forming compositions. For example, acrylic resins (see Patent Literatures 6 to 8) and polyphenol having a specific structure derived from an allyl group (see Patent Literature 14) have been proposed.

CITATION LIST

Patent Literature

Patent Literature 1: Japanese Patent Laid-Open No. 2002-284740
Patent Literature 2: Japanese Patent Laid-Open No. 1999-043524
Patent Literature 3: Japanese Patent Laid-Open No. 1997-263560
Patent Literature 4: International Publication No. WO 2006/132139
Patent Literature 5: International Publication No. WO 2013/073582
Patent Literature 6: Japanese Patent Laid-Open No. 2010-138393
Patent Literature 7: Japanese Patent Laid-Open No. 2015-174877
Patent Literature 8: International Publication No. WO 2014/123005

SUMMARY OF INVENTION

In recent years, a further improvement of the above properties has been required. Thus, there is a demand for further developing novel (meth)acryloyl compounds.

The present invention has been made in light of the above problems. An object of the present invention is to provide a novel (meth)acryloyl compound excellent in heat resistance and a method for producing the same.

The inventor has, as a result of devoted examinations to solve the above problems, found out that a (meth)acryloyl compound having a specific structure can solve the above problems, and reached the present invention.

More specifically, the present invention is as follows.

[1]

A (meth)acryloyl compound represented by the following formula (A):

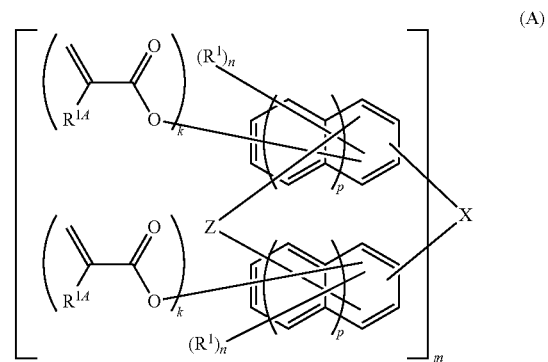

wherein X is a 2m-valent group having 1 to 60 carbon atoms or a single bond; each Z is independently an oxygen atom, a sulfur atom, or not a crosslink; each $R^1$ is independently a linear, branched, or cyclic alkyl group having 1 to 30 carbon atoms, an aryl group having 6 to 30 carbon atoms and optionally having a substituent, an alkenyl group having 2 to 30 carbon atoms and optionally having a substituent, an alkoxy group having 1 to 30 carbon atoms and optionally having a substituent, a halogen atom, a nitro group, an amino group, a carboxylic acid group, a thiol group, a hydroxy group, or a group in which a hydrogen atom of a hydroxy group is replaced with a vinylphenylmethyl group, wherein the alkyl group, the aryl group, the alkenyl group, or the alkoxy group optionally contains an ether bond, a ketone bond, or an ester bond; each $R^{1A}$ is independently a methyl group or a hydrogen atom; each k is independently an integer of 0 to 2, provided that all of the k moieties are not 0 at the same time; m is an integer of 1 to 3; each n is independently an integer of 0 to 5; and each p is independently 0 or 1.

[2]

The (meth)acryloyl compound according to [1], wherein X is a 2m-valent group having 1 to 19 carbon atoms or a single bond, each Z is independently an oxygen atom, a sulfur atom, or not a crosslink, each $R^1$ is independently an alkyl group having 1 to 4 carbon atoms or a halogen atom, each $R^{1A}$ is independently a methyl group or a hydrogen atom, each k is independently an integer of 0 to 2, provided that all of the k moieties are not 0 at the same time, m is an integer of 1 to 3, each n is independently an integer of 0 to 5, and each p is independently 0 or 1, in the above formula (A).

[3]

The (meth)acryloyl compound according to [1] or [2], wherein every p is 1, in the above formula (A).

[4]

The (meth)acryloyl compound according to [1] or [2], wherein Z is an oxygen atom, in the above formula (A).

[5]

The (meth)acryloyl compound according to [1] or [2], wherein Z is not a crosslink, in the above formula (A).

[6]

The (meth)acryloyl compound according to [4], wherein the compound represented by the above formula (A) is a compound represented by the following formula (1):

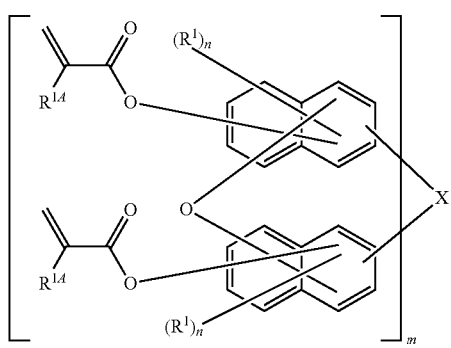

(1)

wherein X, $R^1$, $R^{1A}$, m, and n are the same as the groups in the above formula (A).

[7]

A method for producing the (meth)acryloyl compound according to [6], comprising the step of reacting a compound represented by the following formula (2) with a (meth)acryloyl group introducing agent in the presence of a basic catalyst:

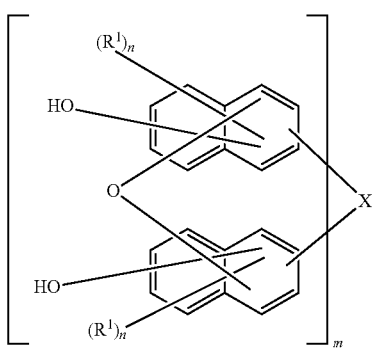

(2)

wherein X is a 2m-valent group having 1 to 19 carbon atoms or a single bond; each $R^1$ is independently an alkyl group having 1 to 4 carbon atoms or a halogen atom; m is an integer of 1 to 3; and each n is independently an integer of 0 to 5.

[8]

The (meth)acryloyl compound according to [4], wherein the compound represented by the above formula (A) is a compound represented by the following formula (1'):

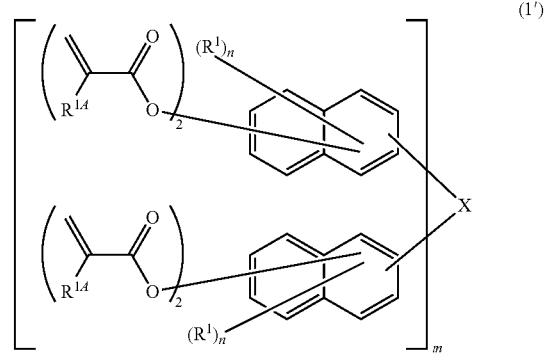

(1')

wherein X, $R^1$, $R^{1A}$, m, and n are the same as the groups in the above formula (A).

[9]

A method for producing the (meth)acryloyl compound according to [8], comprising the step of reacting a compound represented by the following formula (2') with a (meth)acryloyl group introducing agent in the presence of a basic catalyst:

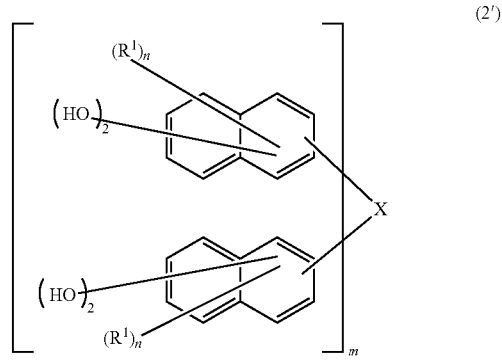

(2')

wherein X is a 2m-valent group having 1 to 19 carbon atoms or a single bond; each $R^1$ is independently an alkyl group having 1 to 4 carbon atoms or a halogen atom; m is an integer of 1 to 3; and each n is independently an integer of 0 to 5.

[10]

The (meth)acryloyl compound according to [6], wherein the compound represented by the above formula (1) is a compound represented by the following formula (4) or (7):

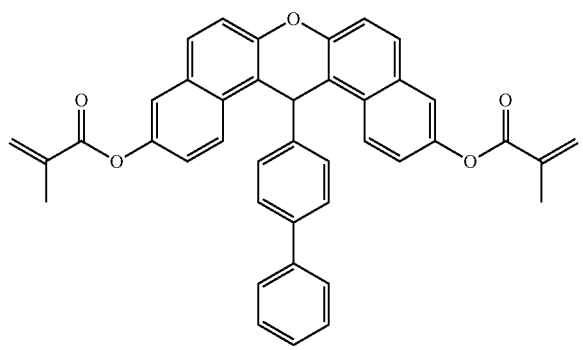

(4)

-continued (7)

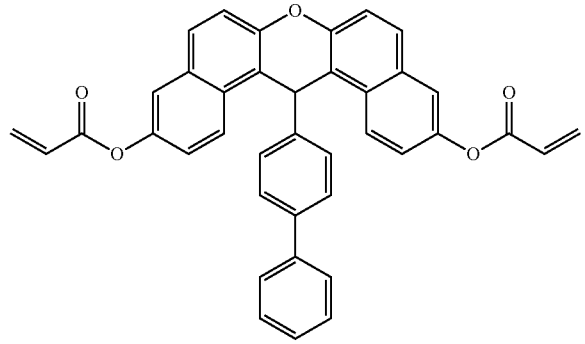

[11]

The (meth)acryloyl compound according to [8], wherein the compound represented by the above formula (1') is a compound represented by the following formula (4'):

(4')

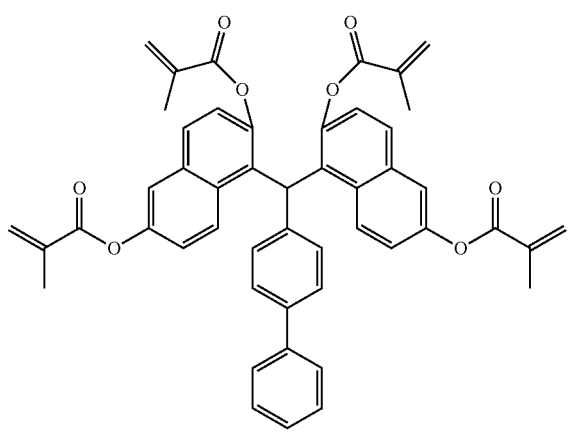

[12]

A resin comprising a constituent unit derived from the compound according to any one of [1] to [6], [8], [10], and [11].

[13]

A composition comprising: one or more selected from the group consisting of the compound according to any one of [1] to [6], [8], [10], and [11]; and the resin according to [12].

[14]

A composition for forming optical component comprising: one or more selected from the group consisting of the compound according to any one of [1] to [6], [8], [10], and [11]; and the resin according to [12].

[15]

A film forming composition for lithography comprising: one or more selected from the group consisting of the compound according to any one of [1] to [6], [8], [10], and [11]; and the resin according to [12].

[16]

A resist composition comprising: one or more selected from the group consisting of the compound according to any one of [1] to [6], [8], [10], and [11]; and the resin according to [12].

[17]

The resist composition according to [16], further comprising a solvent.

[18]

The resist composition according to [16] or [17], further comprising an acid generating agent.

[19]

The resist composition according to any one of [16] to [18], further comprising an acid diffusion controlling agent.

[20]

A method for forming a resist pattern, comprising:
a step of forming a resist film on a substrate using the resist composition according to any one of [16] to [19];
a step of exposing at least a portion of the formed resist film; and
a step of developing the exposed resist film, thereby forming a resist pattern.

[21]

A radiation-sensitive composition comprising:
a component (A) which is one or more selected from the group consisting of the compound according to any one of [1] to [6], [8], [10], and [11]; and the resin according to [12],
an optically active diazonaphthoquinone compound (B); and
a solvent, wherein
the content of the solvent is 20 to 99% by mass based on 100% by mass in total of the radiation-sensitive composition, and
the content of components except for the solvent is 1 to 80% by mass based on 100% by mass in total of the radiation-sensitive composition.

[22]

The radiation-sensitive composition according to [21], wherein the content ratio among the compound and/or the resin (A), the optically active diazonaphthoquinone compound (B), and a further optional component (D) optionally contained in the radiation-sensitive composition ((A)/(B)/(D)) is (1 to 99% by mass)/(99 to 1% by mass)/(0 to 98% by mass), based on 100% by mass of solid components of the radiation-sensitive composition.

[23]

The radiation-sensitive composition according to [21] or [22], wherein the radiation-sensitive composition is capable of forming an amorphous film by spin coating.

[24]

A method for producing an amorphous film, comprising the step of forming an amorphous film on a substrate using the radiation-sensitive composition according to any one of [21] to [23].

[25]

A method for forming a resist pattern, comprising:
a step of forming a resist film on a substrate using the radiation-sensitive composition according to any one of [21] to [23];
a step of exposing at least a portion of the formed resist film; and
a step of developing the exposed resist film, thereby forming a resist pattern.

[26]

An underlayer film forming material for lithography comprising: one or more selected from the group consisting of the compound according to any one of [1] to [6], [8], [10], and [11]; and the resin according to [12].

[27]

A composition for underlayer film formation for lithography comprising:
the underlayer film forming material for lithography according to [26]; and
a solvent.

[28]
The composition for underlayer film formation for lithography according to [27], further comprising an acid generating agent.
[29]
The composition for underlayer film formation for lithography according to [27] or [28], further comprising a cross-linking agent.
[30]
A method for producing an underlayer film for lithography, comprising the step of forming an underlayer film on a substrate using the composition for underlayer film formation for lithography according to any one of [27] to [29].
[31]
A method for forming a resist pattern, comprising:
a step of forming an underlayer film on a substrate using the composition for underlayer film formation for lithography according to any one of [27] to [29];
a step of forming at least one photoresist layer on the underlayer film; and
a step of irradiating a predetermined region of the photoresist layer with radiation for development, thereby forming a resist pattern.
[32]
A method for forming a circuit pattern, comprising:
a step of forming an underlayer film on a substrate using the composition for underlayer film formation for lithography according to any one of [27] to [29];
a step of forming an intermediate layer film on the underlayer film using a resist intermediate layer film material containing a silicon atom;
a step of forming at least one photoresist layer on the intermediate layer film;
a step of irradiating a predetermined region of the photoresist layer with radiation for development, thereby forming a resist pattern;
a step of etching the intermediate layer film with the resist pattern as a mask, thereby forming an intermediate layer film pattern;
a step of etching the underlayer film with the intermediate layer film pattern as an etching mask, thereby forming an underlayer film pattern; and
a step of etching the substrate with the underlayer film pattern as an etching mask, thereby forming a pattern on the substrate.
[33]
A purification method comprising:
a step of obtaining a solution (S) by dissolving one or more selected from the group consisting of the compound according to any one of [1] to [6], [8], [10], and [11] and the resin according to [12] in a solvent; and
a step of extracting impurities in the compound and/or the resin by bringing the obtained solution (S) into contact with an acidic aqueous solution (a first extraction step), wherein
the solvent used in the step of obtaining the solution (S) comprises a solvent that does not mix with water.
[34]
The purification method according to [33], wherein
the acidic aqueous solution is an aqueous mineral acid solution or an aqueous organic acid solution;
the aqueous mineral acid solution is an aqueous mineral acid solution in which one or more selected from the group consisting of hydrochloric acid, sulfuric acid, nitric acid, and phosphoric acid is dissolved in water; and
the aqueous organic acid solution is an aqueous organic acid solution in which one or more selected from the group consisting of acetic acid, propionic acid, oxalic acid, malonic acid, succinic acid, fumaric acid, maleic acid, tartaric acid, citric acid, methanesulfonic acid, phenolsulfonic acid, p-toluenesulfonic acid, and trifluoroacetic acid is dissolved in water.
[35]
The purification method according to [33] or [34], wherein the solvent that does not mix with water is one or more solvents selected from the group consisting of toluene, 2-heptanone, cyclohexanone, cyclopentanone, methyl isobutyl ketone, propylene glycol monomethyl ether acetate, and ethyl acetate.
[36]
The purification method according to any one of [33] to [35], comprising the step of extracting impurities in the compound and/or the resin by further bringing a solution phase comprising the compound and/or the resin into contact with water after the first extraction step (a second extraction step).

The present invention can provide a novel (meth)acryloyl compound excellent in heat resistance and a method for producing the same.

DESCRIPTION OF EMBODIMENTS

Hereinafter, an embodiment of the present invention (hereinafter, referred to as "present embodiment") will be described in detail. However, the present invention is not limited to only the present embodiment, and various changes or modifications can be made without departing from the spirit of the present invention. In the present specification, the "(meth)acryloyl compound" means an acryloyl compound or a methacryloyl compound. The "acryloyl compound" means a compound containing an acryloyl group ($H_2C=CH-C(=O)-$). The "methacryloyl compound" means a compound containing a methacryloyl group ($H_2C=C(CH_3)-C(=O)-$).

[Compound]
The compound of the present embodiment is represented by the formula (A) given below. The compound of the present embodiment has a polycyclic aromatic structure and is therefore excellent in heat resistance. Therefore, the compound of the present embodiment can be suitably used in photoresist components, resin raw materials for materials for electric or electronic components, raw materials for curable resins such as photocurable resins, resin raw materials for structural materials, resin curing agents, or various optical formation compositions.

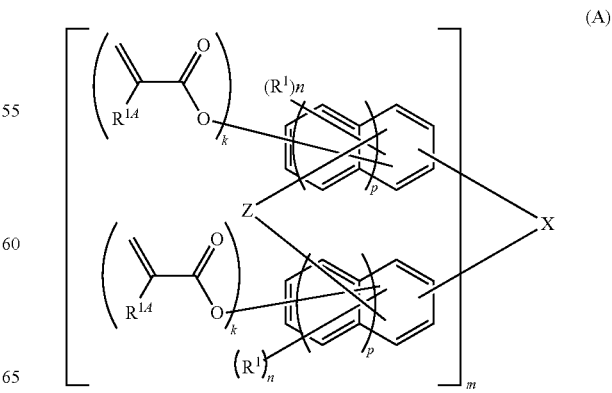

wherein X is a 2m-valent group having 1 to 60 carbon atoms or a single bond; each Z is independently an oxygen atom, a sulfur atom, or not a crosslink; each $R^1$ is independently a linear, branched, or cyclic alkyl group having 1 to 30 carbon atoms, an aryl group having 6 to 30 carbon atoms and optionally having a substituent, an alkenyl group having 2 to 30 carbon atoms and optionally having a substituent, an alkoxy group having 1 to 30 carbon atoms and optionally having a substituent, a halogen atom, a nitro group, an amino group, a carboxylic acid group, a thiol group, a hydroxy group, or a group in which a hydrogen atom of a hydroxy group is replaced with a vinylphenylmethyl group, wherein the alkyl group, the aryl group, the alkenyl group, or the alkoxy group optionally contains an ether bond, a ketone bond, or an ester bond; each $R^{14}$ is independently a methyl group or a hydrogen atom; each k is independently an integer of 0 to 2, provided that all of the k moieties are not 0 at the same time; m is an integer of 1 to 3; each n is independently an integer of 0 to 5; and each p is independently 0 or 1.

X in the above formula (A) is a 2m-valent group having 1 to 60 carbon atoms or a single bond, and each aromatic ring is bonded via this X. The above 2m-valent group refers to an alkylene group having 1 to 60 carbon atoms when m is 1, an alkanetetrayl group having 1 to 60 carbon atoms when m is 2, and an alkanehexayl group having 2 to 60 carbon atoms when m is 3.

Examples of the 2m-valent group include linear hydrocarbon groups, branched hydrocarbon groups, and alicyclic hydrocarbon groups. Herein, the alicyclic hydrocarbon group also includes bridged alicyclic hydrocarbon groups. Also, the 2m-valent group may have a double bond, a heteroatom, or an aromatic group having 6 to 60 carbon atoms.

Examples of the above divalent group having 1 to 60 carbon atoms (alkylene group) include, but not particularly limited to, a methylene group, an ethylene group, a propylene group, a butylene group, a pentylene group, a hexylene group, a heptylene group, an octylene group, a nonylene group, a decylene group, an octadecylene group, a cyclopropylene group, a cyclohexylene group, an adamantylene group, a phenylene group, a tosylene group, a dimethylphenylene group, an ethylphenylene group, a propylphenylene group, a butylphenylene group, a cyclohexylphenylene group, a biphenylene group, a terphenylene group, a naphthylene group, an anthracylene group, a phenanthrylene group, a pyrenylene group, a cyclopropylmethylene group, a cyclohexylmethylene group, an adamantylmethylene group, a phenylmethylene group, a tosylmethylene group, a dimethylphenylmethylene group, an ethylphenylmethylene group, a propylphenylmethylene group, a butylphenylmethylene group, a cyclohexylphenylmethylene group, a biphenylmethylene group, a terphenylmethylene group, a naphthylmethylene group, an anthracylmethylene group, a phenanthrylmethylene group, and a pyrenylmethylene group.

Examples of the above tetravalent group having 1 to 60 carbon atoms (alkanetetrayl group) include, but not particularly limited to, a methanetetrayl group, an ethanetetrayl group, a propanetetrayl group, a butanetetrayl group, a pentanetetrayl group, a hexanetetrayl group, a heptanetetrayl group, an octanetetrayl group, a nonanetetrayl group, a decanetetrayl group, an octadecanetetrayl group, a cyclopropanetetrayl group, a cyclohexanetetrayl group, an adamantanetetrayl group, a benzenetetrayl group, a toluenetetrayl group, a dimethylbenzenetetrayl group, an ethanetetrayl group, a propylbenzenetetrayl group, a butylbenzenetetrayl group, a cyclohexylbenzenetetrayl group, a biphenyltetrayl group, a terphenyltetrayl group, a naphthalenetetrayl group, an anthracenetetrayl group, a phenanthrenetetrayl group, a pyrenetetrayl group, a cyclopropanedimethylene group, a cyclohexanedimethylene group, an adamantanedimethylene group, a benzenedimethylene group, a toluenedimethylene group, a dimethylbenzenedimethylene group, an ethylbenzenedimethylene group, a propylbenzenedimethylene group, a butylbenzenedimethylene group, a cyclohexylbenzenedimethylene group, a biphenyldimethylene group, a terphenyldimethylene group, a naphthalenedimethylene group, an anthracenedimethylene group, a phenanthrenedimethylene group, and a pyrenedimethylene group.

Examples of the above hexavalent group having 2 to 60 carbon atoms (alkanehexayl group) include, but not particularly limited to, an ethanehexayl group, a propanehexayl group, a butanehexayl group, a pentanehexayl group, a hexanehexayl group, a heptanehexayl group, an octanehexayl group, a nonanehexayl group, a decanehexayl group, an octadecanehexayl group, a cyclopropanehexayl group, a cyclohexanehexayl group, an adamantanehexayl group, a benzenehexayl group, a toluenehexayl group, a dimethylbenzenehexayl group, an ethanehexayl group, a propylbenzenehexayl group, a butylbenzenehexayl group, a cyclohexylbenzenehexayl group, a biphenylhexayl group, a terphenylhexayl group, a naphthalenehexayl group, an anthracenehexayl group, a phenanthrenehexayl group, a pyrenehexayl group, a cyclopropanetrimethylene group, a cyclohexanetrimethylene group, an adamantanetrimethylene group, a benzenetrimethylene group, a toluenetrimethylene group, a dimethylbenzenetrimethylene group, a ethylbenzenetrimethylene group, a propylbenzenetrimethylene group, a butylbenzenetrimethylene group, a biphenyltrimethylene group, a terphenyltrimethylene group, a naphthalenetrimethylene group, an anthracenetrimethylene group, a phenanthrenetrimethylene group, and a pyrenetrimethylene group.

Among them, a phenylene group, a tosylene group, a dimethylphenylene group, an ethylphenylene group, a propylphenylene group, a butylphenylene group, a cyclohexylphenylene group, a biphenylene group, a terphenylene group, a naphthylene group, an anthracylene group, a phenanthrylene group, a pyrenylene group, a phenylmethylene group, a tosylmethylene group, a dimethylphenylmethylene group, an ethylphenylmethylene group, a propylphenylmethylene group, a butylphenylmethylene group, a cyclohexylphenylmethylene group, a biphenylmethylene group, a terphenylmethylene group, a naphthylmethylene group, an anthracylmethylene group, a phenanthrylmethylene group, or a pyrenylmethylene group is preferable from the viewpoint of heat resistance. Among them, a phenylmethylene group, a tosylmethylene group, a dimethylphenylmethylene group, an ethylphenylmethylene group, a propylphenylmethylene group, a butylphenylmethylene group, a cyclohexylphenylmethylene group, a biphenylmethylene group, a terphenylmethylene group, a naphthylmethylene group, an anthracylmethylene group, a phenanthrylmethylene group, or a pyrenylmethylene group is particularly preferable from the viewpoint of the availability of raw materials.

Each Z in the above formula (A) is independently an oxygen atom, a sulfur atom or not a crosslink. Z is preferably an oxygen atom from the viewpoint of high heat resistance. Also, Z is preferably not a crosslink from the viewpoint of high solubility.

Each $R^1$ in the above formula (A) is independently a linear, branched, or cyclic alkyl group having 1 to 30 carbon atoms, an aryl group having 6 to 30 carbon atoms and optionally having a substituent, an alkenyl group having 2 to 30 carbon atoms and optionally having a substituent, an alkoxy group having 1 to 30 carbon atoms and optionally having a substituent, a halogen atom, a nitro group, an amino group, a carboxylic acid group, a thiol group, a hydroxy group, or a group in which a hydrogen atom of a hydroxy group is replaced with a vinylphenylmethyl group, wherein the alkyl group, the aryl group, the alkenyl group, or the alkoxy group optionally contains an ether bond, a ketone bond, or an ester bond. Among them, an alkyl group having 1 to 4 carbon atoms or a halogen atom is preferred. Examples thereof include a methyl group, an ethyl group, a propyl group, a butyl group, a fluorine atom, a chlorine atom, a bromine atom, and an iodine atom.

Each $R^{1A}$ in the above formula (A) is independently a methyl group or a hydrogen atom.

Each k in the above formula (A) is independently an integer of 0 to 2, provided that all of the k moieties are not 0 at the same time.

m in the above formula (A) is an integer of 1 to 3. m is preferably 1 or 2 from the viewpoint of solubility.

Each n in the above formula (A) is independently an integer of 0 to 5. n is preferably an integer of 1 to 5 from the viewpoint of solubility. Also, n is preferably 0 from the viewpoint of heat resistance.

Each p in the above formula (A) is independently 0 or 1. Every p in the above formula (A) is preferably 1 from the viewpoint of heat resistance.

It is preferable that X is a 2m-valent group having 1 to 19 carbon atoms or a single bond, each Z is independently an oxygen atom, a sulfur atom, or not a crosslink, each $R^1$ is independently an alkyl group having 1 to 4 carbon atoms or a halogen atom, each $R^{1A}$ is independently a methyl group or a hydrogen atom, each k is independently an integer of 0 to 2, provided that all of the k moieties are not 0 at the same time, m is an integer of 1 to 3, each n is independently an integer of 0 to 5, and each p is preferably independently 0 or 1, in the above formula (A).

The (meth)acryloyl compound of the present embodiment is preferably a compound represented by the following formula (1) from the viewpoint of heat resistance.

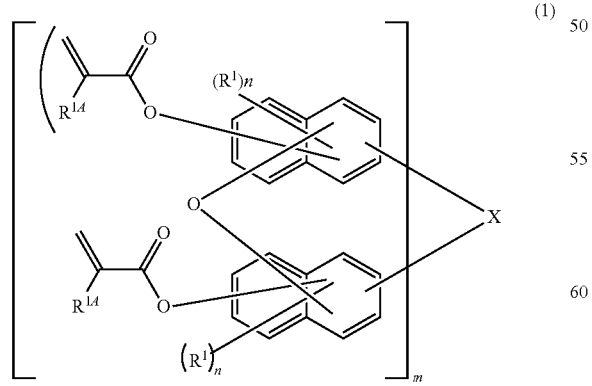

wherein X, $R^1$, $R^{1A}$, m, and n are the same as the groups in the above formula (A).

In the present embodiment, the compound represented by the above formula (1) is preferably a compound represented by the formula (1-1) from the viewpoint of heat resistance.

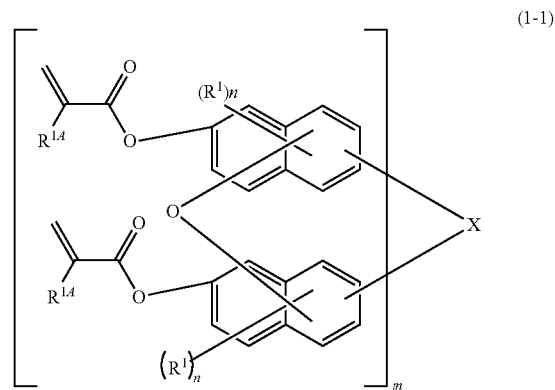

wherein X, $R^1$, $R^{1A}$, m, and n are the same as the groups in the above formula (A).

In the present embodiment, specific examples of the compound represented by the above formula (1) include, but not limited to, those described below, from the viewpoint of heat resistance and solubility in an organic solvent. A compound represented by the following formula (4) or (7) is preferable.

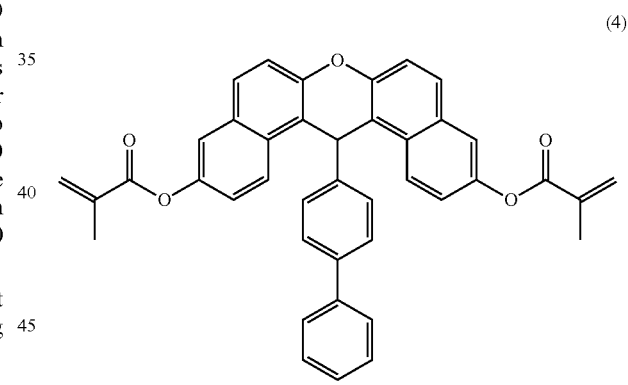

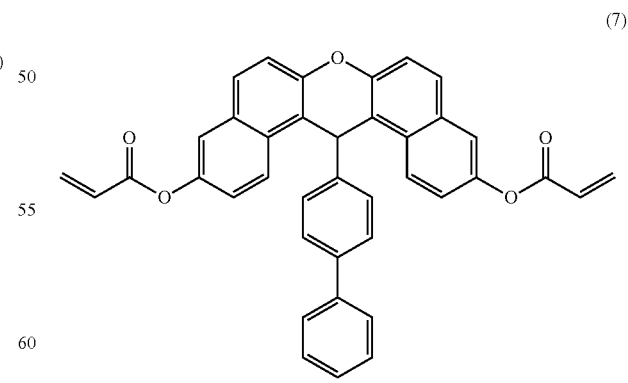

In the following formula, $R^2$ is a group represented by the following formula (6'), Y is an oxygen atom, a sulfur atom, or not a crosslink, and m' and m" are each independently an integer of 0 to 5.

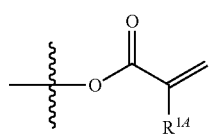
(6')
In the formula (6'), $R^{1A}$ is a methyl group or a hydrogen atom.
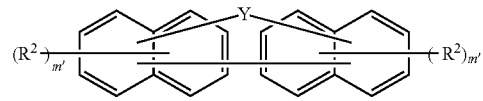
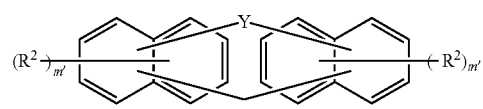
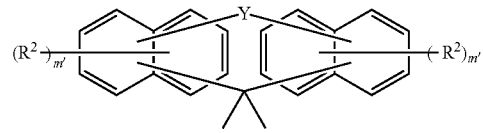
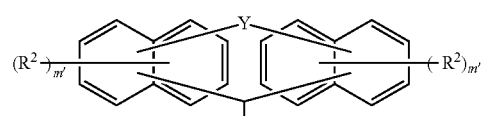
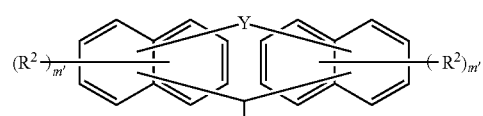
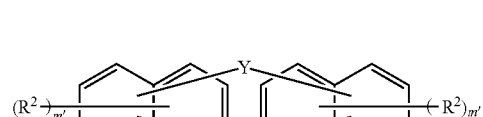
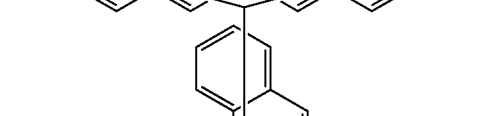
-continued
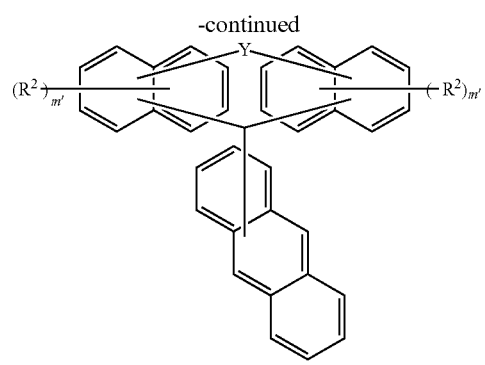
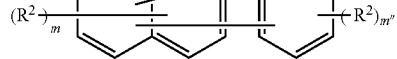
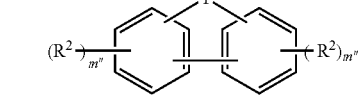
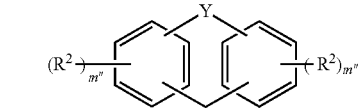
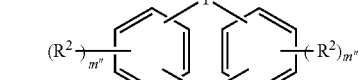
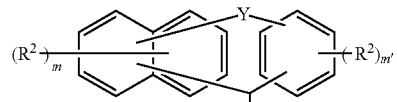
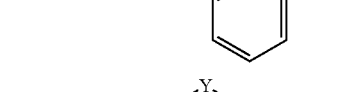
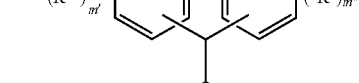

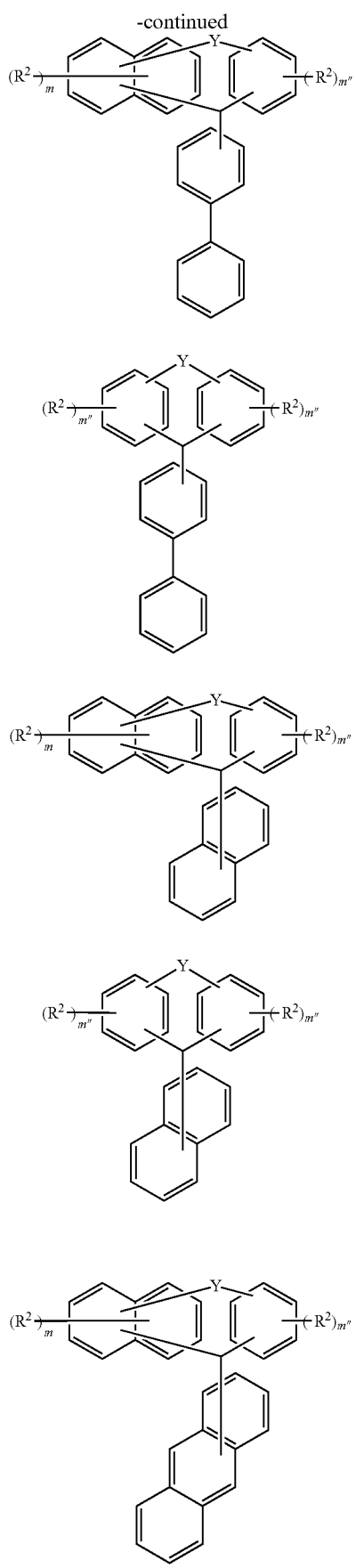
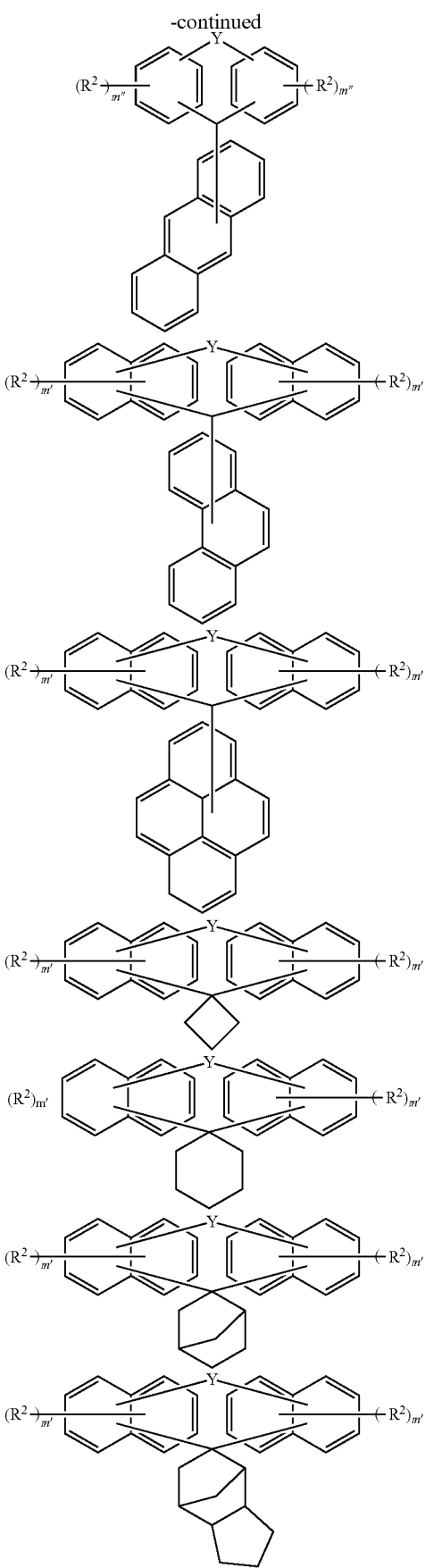

-continued
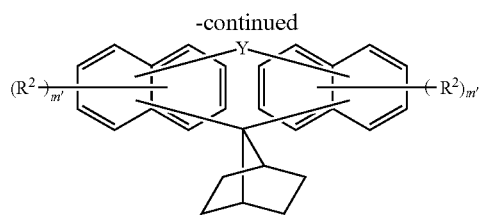
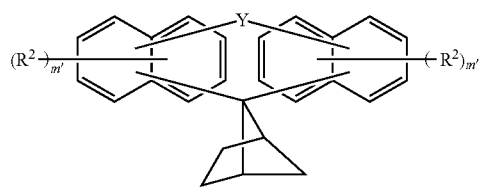
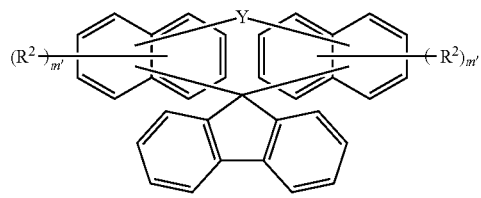
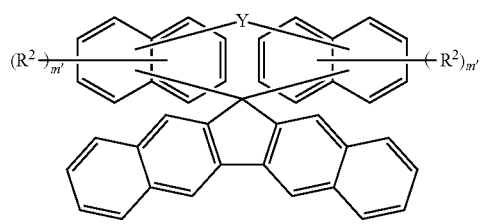
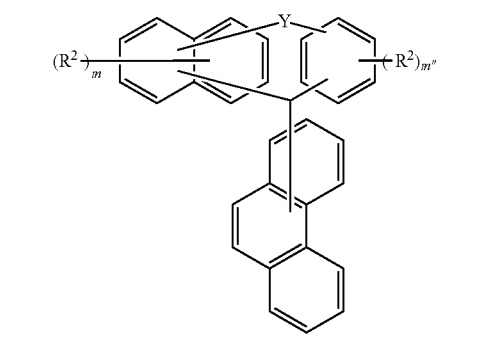
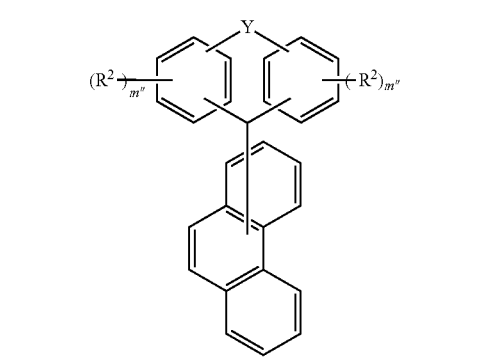
-continued
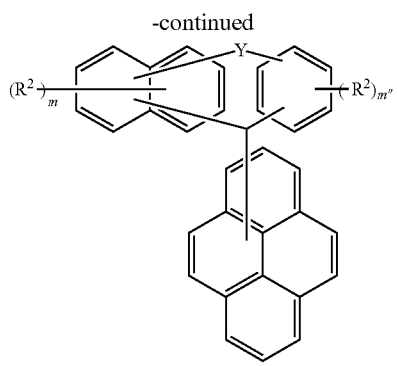
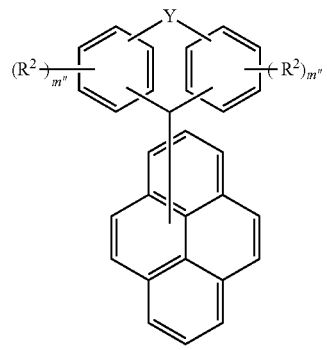
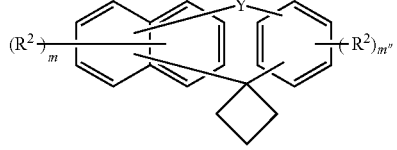
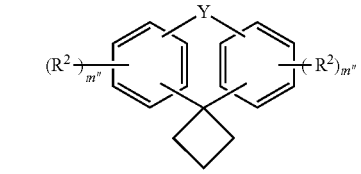
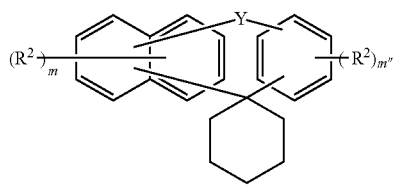
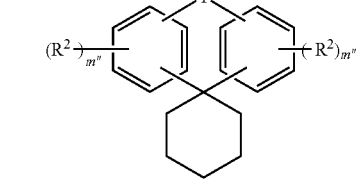
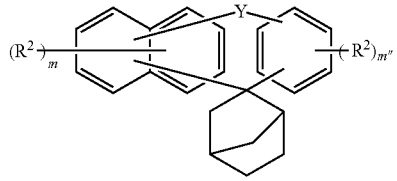

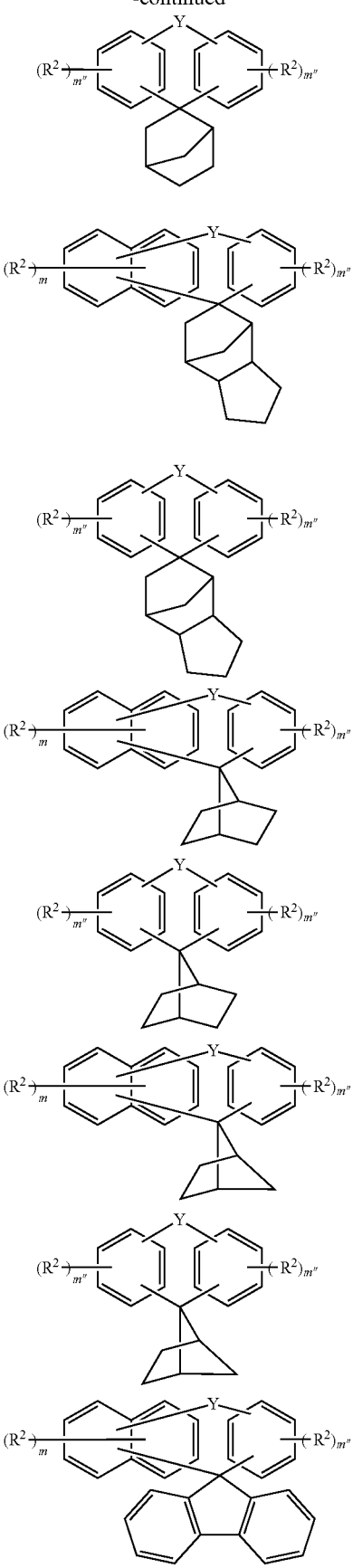
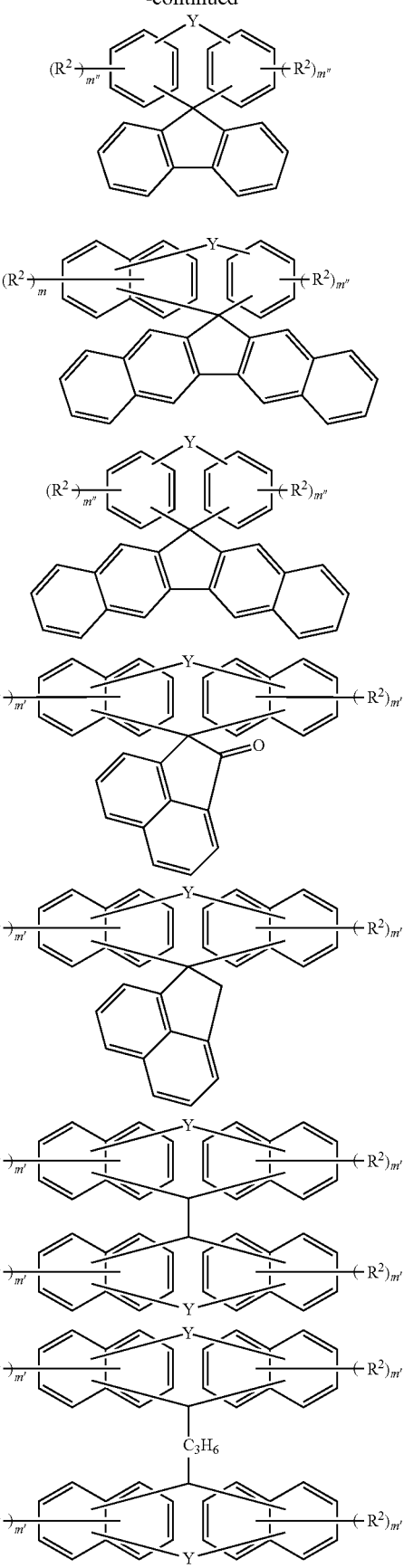

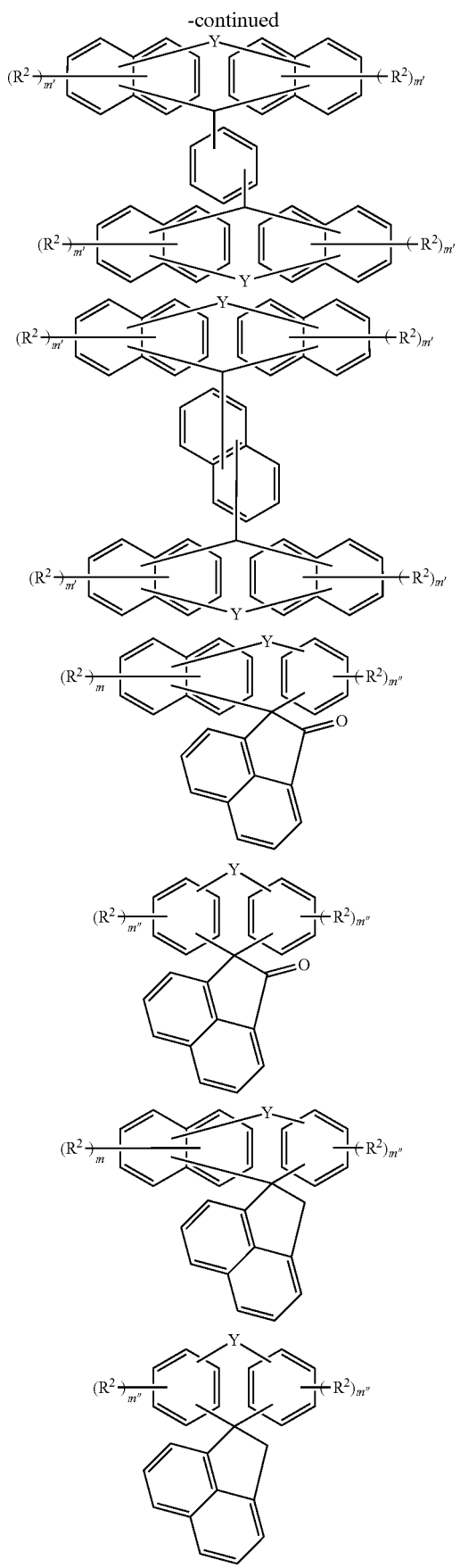
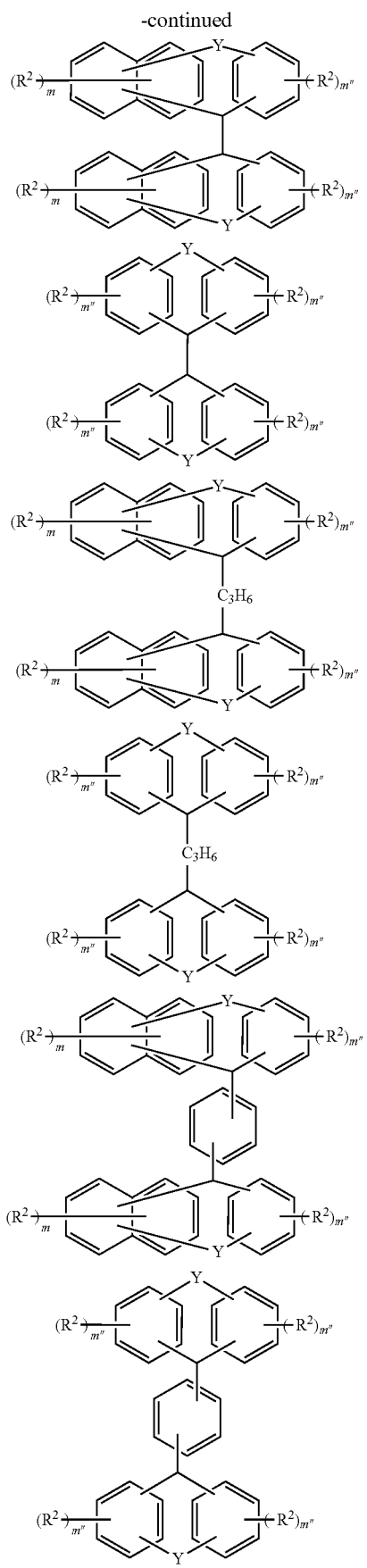

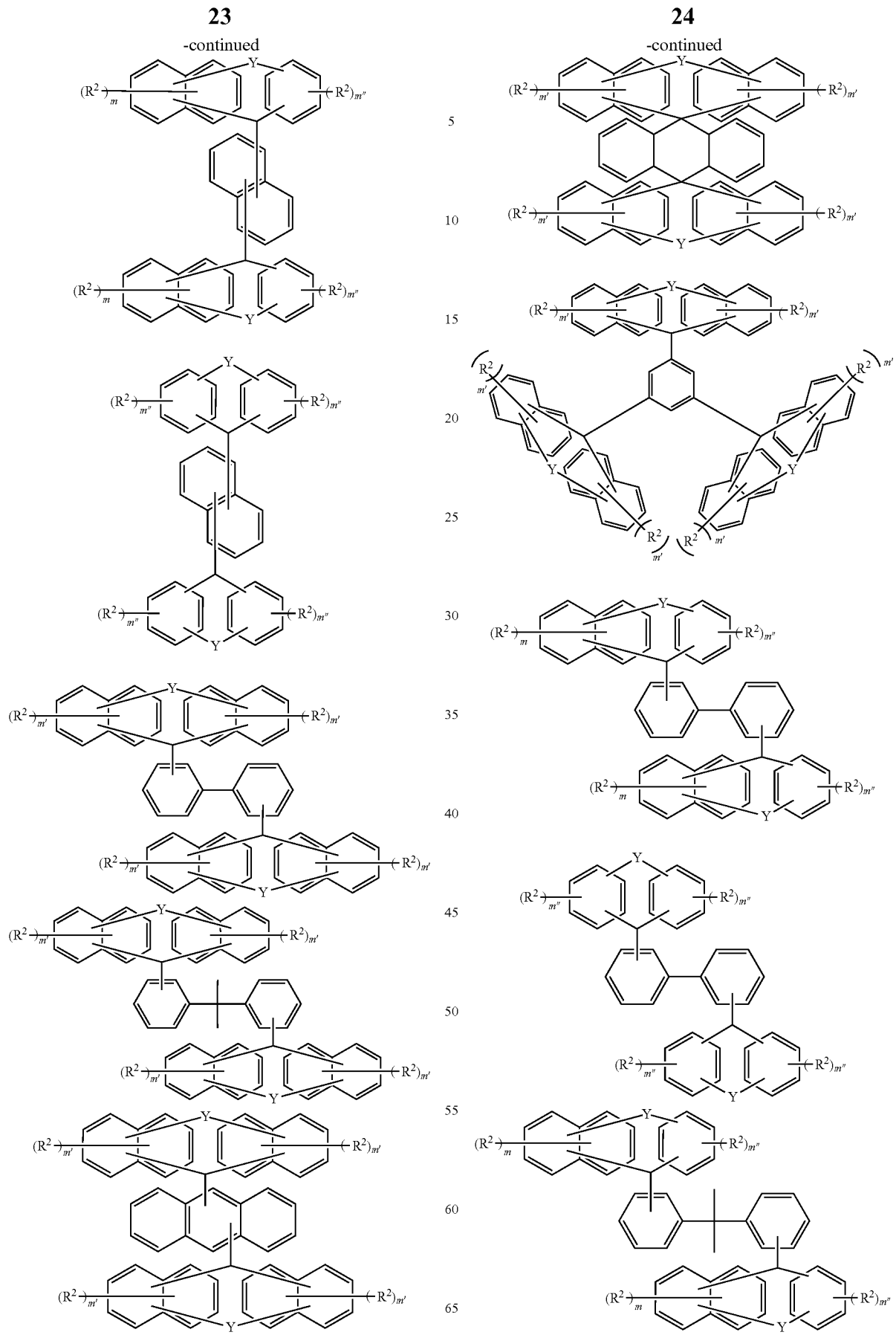

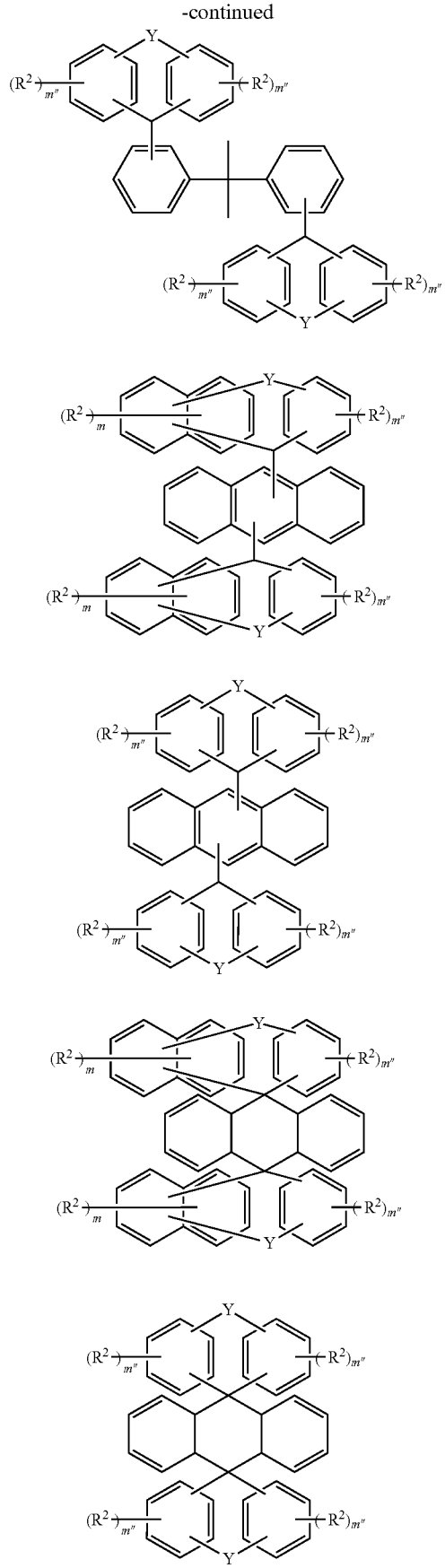

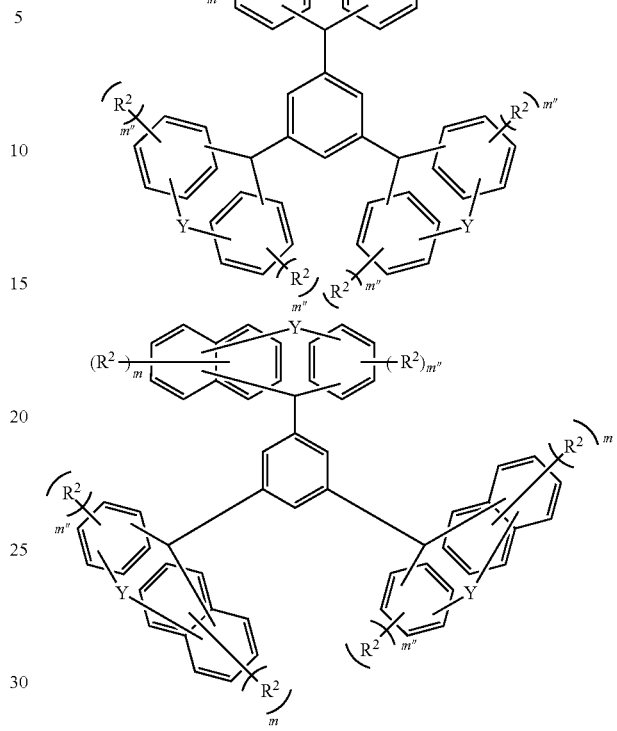

The compound represented by the formula (1) of the present embodiment can be produced by a publicly known method. Examples thereof include a production method comprising the step of reacting a compound represented by the formula (2) given below with a (meth)acryloyl group introducing agent in the presence of a basic catalyst. Examples of the method for purifying the compound represented by the formula (1) obtained by this production method include, but not particularly limited to, crystallization. This production method can achieve efficient production, especially, with a small amount of by-product. Alternatively, the compound represented by the formula (1) may be obtained by reacting a compound represented by the formula (2) given below with a (meth)acryloyl group introducing agent in the presence of an acidic catalyst. For these reactions, a polymerization inhibitor may be used in combination therewith.

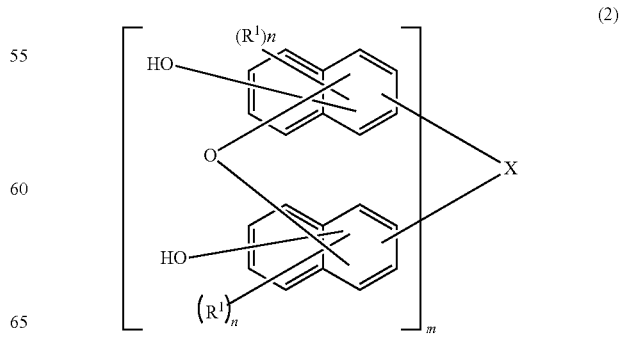

wherein X is a 2m-valent group having 1 to 19 carbon atoms or a single bond; each R¹ is independently an alkyl group having 1 to 4 carbon atoms or a halogen atom; m is an integer of 1 to 3; and each n is independently an integer of 0 to 5.

In the present embodiment, the compound represented by the above formula (2) is preferably a compound represented by the formula (2-1) from the viewpoint of heat resistance and solubility in an organic solvent.

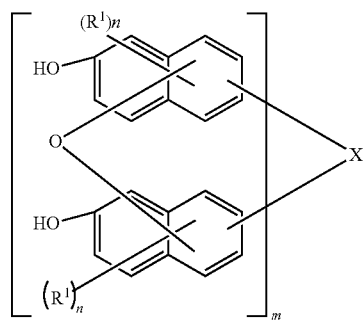

(2-1)

wherein X, R¹, m, and n are the same as in the above formula (2).

More specifically, for example, 1 mol of a compound represented by the formula (3) given below, 2.6 mol of methacrylic acid chloride, and 5.2 mol of potassium carbonate are placed in a 3 L flask and reacted in a dimethylformamide solvent at 90° C. while heated in an oil bath in the dimethylformamide. Then, the reaction solution is cooled, and crude crystals are isolated by crystallization. The obtained crude crystals and sodium hydroxide are refluxed for 4 hours in a methanol solvent and cooled by air cooling. Then, the precipitated crystals can be collected by filtration and rinsed to produce a compound represented by the following formula (4).

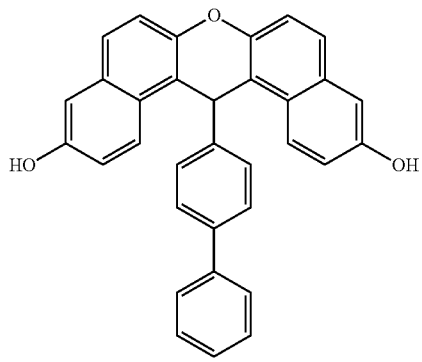

(3)

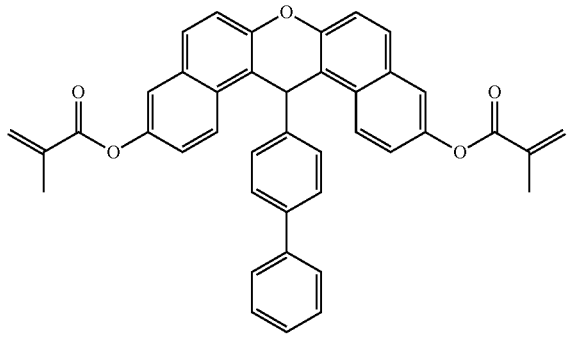

(4)

The compound represented by the formula (2) used in the present embodiment can be produced by, for example, reacting a compound represented by the formula (5) with an aldehyde of 1 to 19 carbon atoms at a relatively high temperature in the presence of an acid catalyst. The production method which involves reacting a compound represented by the formula (5) with an aldehyde of 1 to 19 carbon atoms at a relatively high temperature of 60 to 120° C. in the presence of an acid catalyst can achieve efficient production, especially, with a small amount of by-product. The structure of the group X in the produced compound of the formula (1) is determined depending on the type of the aldehyde used. Specifically, for example, the compound represented by the formula (3) can be produced by reacting 2,6-naphthalenediol with 4-biphenylcarboxyaldehyde at 100° C. in the presence of a sulfuric acid catalyst.

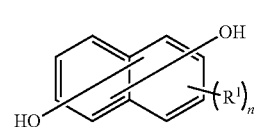

(5)

wherein R¹ is an alkyl group having 1 to 4 carbon atoms or a halogen atom; and n is an integer of 0 to 5.

The compound represented by the above formula (5) is used without particular limitations as long as the compound has a dihydroxynaphthalene skeleton. Use of the compound having a naphthalene skeleton can be expected to improve performance in terms of heat resistance over a polyphenol compound produced using a dihydroxy compound having a benzene ring skeleton. For example, naphthalenediol, methylnaphthalenediol, ethylnaphthalenediol, propylnaphthalenediol, butylnaphthalenediol, fluoronaphthalenediol, chloronaphthalenediol, bromonaphthalenediol, or iodonaphthalenediol is used. These are easily available as reagents. One kind or two or more kinds can be used as the compound represented by the formula (5).

The structure of the group X in the produced compound of the formula (2) is determined depending on the type of the aldehyde of 1 to 19 carbon atoms used in the present embodiment. Examples of the aldehyde of 1 to 19 carbon atoms include formaldehyde, acetaldehyde, propionaldehyde, butylaldehyde, pentylaldehyde, hexylaldehyde, heptylaldehyde, octylaldehyde, nonylaldehyde, decylaldehyde, octadecylaldehyde, cyclopropylaldehyde, cyclohexylaldehyde, adamantylcarboxyaldehyde, benzaldehyde, methylbenzaldehyde, dimethylbenzaldehyde, ethylbenzaldehyde, propylbenzaldehyde, butylbenzaldehyde, cyclohexylbenzaldehyde, biphenylcarboxyaldehyde, terphenylcarboxyaldehyde, naphthalenecarboxyaldehyde, anthracenecarboxyaldehyde, phenanthrenecarboxyaldehyde, pyrenecarboxyaldehyde, methanedialdehyde, ethanedialdehyde, propiondialdehyde, butyldialdehyde, pentyldialdehyde, hexyldialdehyde, heptyldialdehyde, octyldialdehyde, nonyldialdehyde, decyldialdehyde, octadecyldialdehyde, cyclopropyldialdehyde, cyclohexyldialdehyde, adamantyldicarboxyaldehyde, benzenedialdehyde, methylbenzenedialdehyde, dimethylbenzenedialdehyde, ethylbenzenedialdehyde, propylbenzenedialdehyde, butylbenzenedialdehyde, cyclohexylbenzenedialdehyde, biphenyldicarboxyaldehyde, terphenyldicarboxyaldehyde, naphthalenedicarboxyaldehyde, anthracenedicarboxyaldehyde, phenanthrenedicarboxyaldehyde, pyrenedicarboxyaldehyde, methanetrialdehyde, ethanetrialdehyde, propiontrialdehyde, butyltrialdehyde, pentyltrialdehyde, hexyltrialdehyde, heptyltrialdehyde, octyltrialdehyde, nonyltrialdehyde, decyltrialdehyde, octadecyltrialdehyde, cyclopropyltrialdehyde, cyclohexyltrialdehyde, adamantyltricarboxyaldehyde, benzenetrialdehyde, methylbenzenetrialdehyde, dimethylbenzenetrialdehyde, ethylbenzenetrialdehyde, propylbenzenetrialdehyde, butylbenzenetrialdehyde, cyclohexylbenzenetrialdehyde, biphenyltricarboxyaldehyde, terphenyltricarboxyaldehyde, naphthalenetricarboxyaldehyde, anthracenetricarboxyaldehyde, phenanthrenetricarboxyaldehyde, and pyrenetricarboxyaldehyde.

Among them, benzaldehyde, methylbenzaldehyde, dimethylbenzaldehyde, ethylbenzaldehyde, propylbenzaldehyde, butylbenzaldehyde, cyclohexylbenzaldehyde, biphenylcarboxyaldehyde, terphenylcarboxyaldehyde, naphthalenecarboxyaldehyde, anthracenecarboxyaldehyde, phenanthrenecarboxyaldehyde, pyrenecarboxyaldehyde, benzenedialdehyde, methylbenzenedialdehyde, dimethylbenzenedialdehyde, ethylbenzenedialdehyde, propylbenzenedialdehyde, butylbenzenedialdehyde, cyclohexylbenzenedialdehyde, biphenyldicarboxyaldehyde, terphenyldicarboxyaldehyde, naphthalenedicarboxyaldehyde, anthracenedicarboxyaldehyde, phenanthrenedicarboxyaldehyde, pyrenedicarboxyaldehyde, benzenetrialdehyde, methylbenzenetrialdehyde, dimethylbenzenetrialdehyde, ethylbenzenetrialdehyde, propylbenzenetrialdehyde, butylbenzenetrialdehyde, cyclohexylbenzenetrialdehyde, biphenyltricarboxyaldehyde, terphenyltricarboxyaldehyde, naphthalenetricarboxyaldehyde, anthracenetricarboxyaldehyde, phenanthrenetricarboxyaldehyde, or pyrenetricarboxyaldehyde having an aromatic ring is preferable from the viewpoint of heat resistance. Among them, benzaldehyde, biphenylcarboxyaldehyde, terphenylcarboxyaldehyde, naphthalenecarboxyaldehyde, anthracenecarboxyaldehyde, phenanthrenecarboxyaldehyde, pyrenecarboxyaldehyde, benzenedialdehyde, biphenyldicarboxyaldehyde, terphenyldicarboxyaldehyde, naphthalenedicarboxyaldehyde, anthracenedicarboxyaldehyde, phenanthrenedicarboxyaldehyde, or pyrenedicarboxyaldehyde is particularly preferable.

The aldehyde of 1 to 19 carbon atoms is easily available as an industrial product or a reagent. One type or two or more types can be used as the aldehyde of 1 to 19 carbon atoms.

The (meth)acryloyl group introducing agent used in the present embodiment is used without particular limitations as long as the compound can replace a hydrogen atom of a hydroxy group in the compound represented by the formula (2) with a (meth)acryloyl group represented by the formula (6) given below. Examples of such a compound include (meth)acryloyl acid chloride, (meth)acryloyl acid bromide, (meth)acryloyl acid iodide, and (meth)acryloyl acid. One type or two or more types can be used as the (meth)acryloyl group introducing agent.

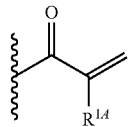

(6)

wherein $R^{14}$ is a methyl group or a hydrogen atom.

The basic catalyst used in the reaction of the compound represented by the formula (2) of the present embodiment with the (meth)acryloyl group introducing agent can be arbitrarily selected from well-known basic catalysts. Examples thereof include: inorganic bases such as metal hydroxides (e.g., alkali metal or alkaline earth metal hydroxides such as sodium hydroxide and potassium hydroxide), metal carbonates (e.g., alkali metal or alkaline earth metal carbonates such as sodium carbonate and potassium carbonate), and alkali metal or alkaline earth metal bicarbonates such as sodium bicarbonate and potassium bicarbonate; and organic bases such as amines (e.g., tertiary amines (trialkylamines such as triethylamine, aromatic tertiary amines such as N,N-dimethylaniline, and heterocyclic tertiary amines such as 1-methylimidazole), and carboxylic acid metal salts (e.g., acetic acid alkali metal or alkaline earth metal salts such as sodium acetate and calcium acetate). Sodium carbonate or potassium carbonate is preferable from the viewpoint of production such as easy availability and handleability. One type or two or more types can be used as the basic catalyst.

Next, conditions for the reaction of the compound represented by the formula (2) with the (meth)acryloyl group introducing agent will be described in detail.

The reaction proceeds by using 1 mol to an excess of the (meth)acryloyl group introducing agent and 0.001 to 1 mol of the basic catalyst based on 1 mol of the compound represented by the formula (2), and reacting them at 20 to 150° C. at normal pressure for about 20 minutes to 100 hours. The target component can be isolated by a publicly known method after the reaction. Examples thereof include a method which involves cooling the reaction solution in ice water or the like to precipitate crystals, which are then isolated to obtain crude crystals.

Subsequently, the crude crystals are dissolved in an organic solvent. To the solution, a strong base is added, and the mixture is reacted at 20 to 150° C. at normal pressure for about 20 minutes to 100 hours. The target component can be isolated by a publicly known method after the reaction. Examples thereof include a method which involves concentrating the reaction solution, precipitating the reaction product by the addition of pure water, cooling the reaction solution to room temperature, then separating the precipitates by filtration, filtering and drying the obtained solid matter, then separating and purifying the solid matter from by-products by column chromatography, and distilling off the solvent, followed by filtration and drying to obtain the target compound represented by the formula (1).

Next, the compound of the present embodiment represented by the formula (1') will be described. The compound represented by the above formula (A) is preferably a compound represented by the following formula (1') from the viewpoint of heat resistance.

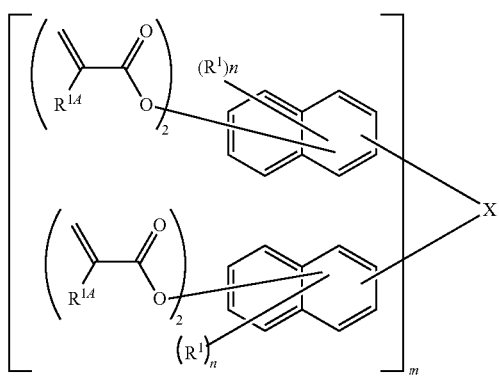

(1')

wherein X, $R^1$, $R^{1A}$, m, and n are the same as the groups in the above formula (A).

In the present embodiment, the compound represented by the above formula (1') is preferably a compound represented by the following formula (1'-1) from the viewpoint of heat resistance and solubility in an organic solvent.

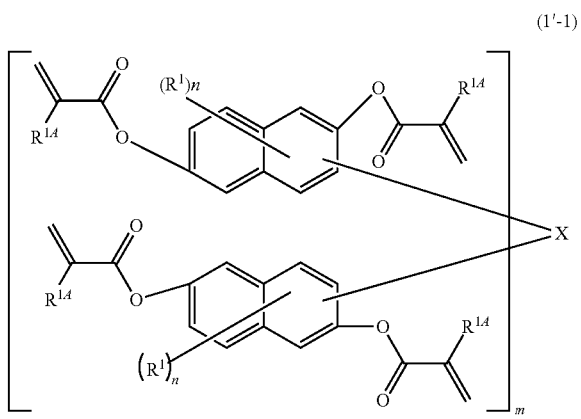

(1'-1)

wherein X, $R^1$, $R^{1A}$, m, and n are the same as the groups in the above formula (A).

In the present embodiment, the compound represented by the above formula (1') is preferably a compound represented by the following formula (4') from the viewpoint of heat resistance.

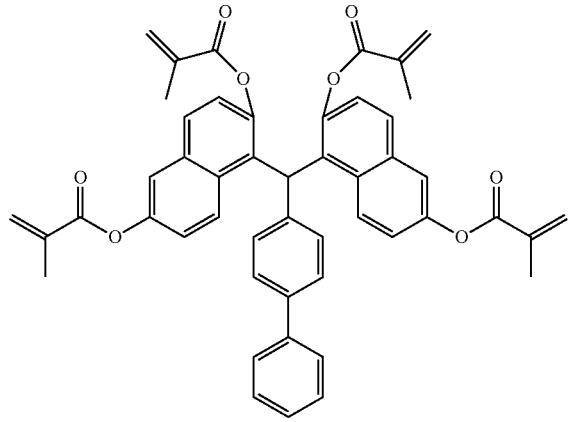

(4')

The compound of the formula (1') of the present embodiment can be produced by a publicly known method. Examples thereof include a production method comprising the step of reacting a compound represented by the formula (2') given below with a (meth)acryloyl group introducing agent in the presence of a basic catalyst. Examples of the method for purifying the compound represented by the formula (1') obtained by this production method include, but not particularly limited to, crystallization. This production method can achieve efficient production, especially, with a small amount of by-product. Alternatively, the compound represented by the formula (1') may be obtained by reacting a compound represented by the formula (2') with a (meth)acryloyl group introducing agent in the presence of an acidic catalyst. For these reactions, a polymerization inhibitor may be used in combination therewith.

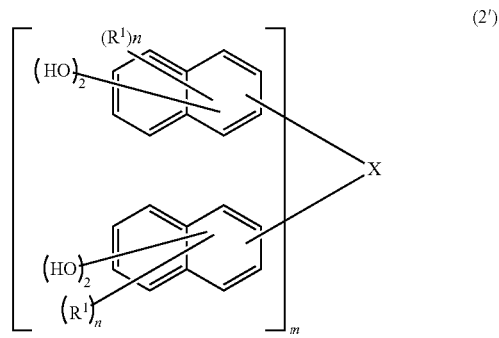

(2')

wherein X is a 2m-valent group having 1 to 19 carbon atoms or a single bond; each $R^1$ is independently an alkyl group having 1 to 4 carbon atoms or a halogen atom; m is an integer of 1 to 3; and each n is independently an integer of 0 to 5.

In the present embodiment, the compound represented by the above formula (2') is preferably a compound represented by the formula (2'-1) from the viewpoint of heat resistance and solubility in an organic solvent.

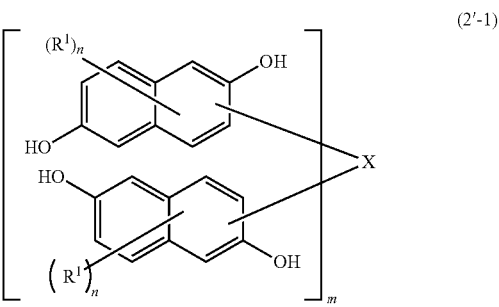

(2'-1)

wherein X, $R^1$, m, and n are the same as in the above formula (2').

Specifically, for example, 1 mol of a compound represented by the formula (3') given below, 5.2 mol of methacryloyl chloride, and 10.4 mol of potassium carbonate are placed in a 3 L flask and reacted in a dimethylformamide solvent at 90° C. while heated in an oil bath in the dimethylformamide. Then, the reaction solution is cooled, and crude crystals are isolated by crystallization. The obtained crude crystals and sodium hydroxide are refluxed for 4 hours in a methanol solvent and cooled by air cooling. Then, the precipitated crystals can be collected by filtration and rinsed to produce a compound represented by the following formula (4').

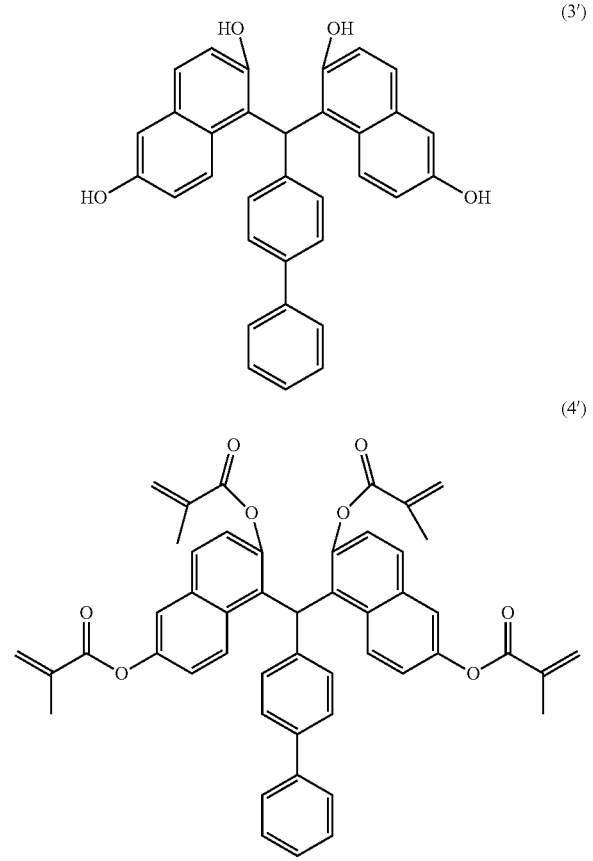

The compound represented by the formula (2') used in the present embodiment can be produced by, for example, reacting a compound represented by the formula (5) given below with an aldehyde of 1 to 19 carbon atoms at a relatively low temperature of 20 to 60° C. in the presence of an acid catalyst. The production method which involves reacting a compound represented by the formula (5) given below with an aldehyde of 1 to 19 carbon atoms at a relatively low temperature in the presence of an acid catalyst can achieve efficient production, especially, with a small amount of by-product. The structure of the group X in the produced compound of the formula (1') is determined depending on the type of the aldehyde used. Specifically, for example, the compound represented by the above formula (3') can be produced by reacting 2,6-naphthalenediol with 4-biphenylcarboxyaldehyde at 30° C. in the presence of a sulfuric acid catalyst.

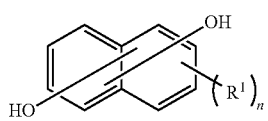

wherein $R^1$ is an alkyl group having 1 to 4 carbon atoms or a halogen atom; and n is an integer of 0 to 5.

The compound represented by the formula (5) used in the present embodiment is used without particular limitations as long as the compound has a dihydroxynaphthalene skeleton. Use of the compound having a naphthalene skeleton can be expected to improve performance in terms of heat resistance over a polyphenol compound produced using a dihydroxy compound having a benzene ring skeleton. For example, naphthalenediol, methylnaphthalenediol, ethylnaphthalenediol, propylnaphthalenediol, butylnaphthalenediol, fluoronaphthalenediol, chloronaphthalenediol, bromonaphthalenediol, or iodonaphthalenediol is used. These are easily available as reagents. One kind or two or more kinds can be used as the compound represented by the formula (5).

The structure of the group X in the produced compound of the formula (2) is determined depending on the type of the aldehyde of 1 to 19 carbon atoms used in the present embodiment. Examples of the aldehyde of 1 to 19 carbon atoms include formaldehyde, acetaldehyde, propionaldehyde, butylaldehyde, pentylaldehyde, hexylaldehyde, heptylaldehyde, octylaldehyde, nonylaldehyde, decylaldehyde, octadecylaldehyde, cyclopropylaldehyde, cyclohexylaldehyde, adamantylcarboxyaldehyde, benzaldehyde, methylbenzaldehyde, dimethylbenzaldehyde, ethylbenzaldehyde, propylbenzaldehyde, butylbenzaldehyde, cyclohexylbenzaldehyde, biphenylcarboxyaldehyde, terphenylcarboxyaldehyde, naphthalenecarboxyaldehyde, anthracenecarboxyaldehyde, phenanthrenecarboxyaldehyde, pyrenecarboxyaldehyde, methanedialdehyde, ethanedialdehyde, propiondialdehyde, butyldialdehyde, pentyldialdehyde, hexyldialdehyde, heptyldialdehyde, octyldialdehyde, nonyldialdehyde, decyldialdehyde, octadecyldialdehyde, cyclopropyldialdehyde, cyclohexyldialdehyde, adamantyldicarboxyaldehyde, benzenedialdehyde, methylbenzenedialdehyde, dimethylbenzenedialdehyde, ethylbenzenedialdehyde, propylbenzenedialdehyde, butylbenzenedialdehyde, cyclohexylbenzenedialdehyde, biphenyldicarboxyaldehyde, terphenyldicarboxyaldehyde, naphthalenedicarboxyaldehyde, anthracenedicarboxyaldehyde, phenanthrenedicarboxyaldehyde, pyrenedicarboxyaldehyde, methanetrialdehyde, ethanetrialdehyde, propiontrialdehyde, butyltrialdehyde, pentyltrialdehyde, hexyltrialdehyde, heptyltrialdehyde, octyltrialdehyde, nonyltrialdehyde, decyltrialdehyde, octadecyltrialdehyde, cyclopropyltrialdehyde, cyclohexyltrialdehyde, adamantyltricarboxyaldehyde, benzenetrialdehyde, methylbenzenetrialdehyde, dimethylbenzenetrialdehyde, ethylbenzenetrialdehyde, propylbenzenetrialdehyde, butylbenzenetrialdehyde, cyclohexylbenzenetrialdehyde, biphenyltricarboxyaldehyde, terphenyltricarboxyaldehyde, naphthalenetricarboxyaldehyde, anthracenetricarboxyaldehyde, phenanthrenetricarboxyaldehyde, and pyrenetricarboxyaldehyde.

Among them, benzaldehyde, methylbenzaldehyde, dimethylbenzaldehyde, ethylbenzaldehyde, propylbenzaldehyde, butylbenzaldehyde, cyclohexylbenzaldehyde, biphenylcarboxyaldehyde, terphenylcarboxyaldehyde, naphthalenecarboxyaldehyde, anthracenecarboxyaldehyde, phenanthrenecarboxyaldehyde, pyrenecarboxyaldehyde, benzenedialdehyde, methylbenzenedialdehyde, dimethylbenzenedialdehyde, ethylbenzenedialdehyde, propylbenzenedialdehyde, butylbenzenedialdehyde, cyclohexylbenzenedialdehyde, biphenyldicarboxyaldehyde, terphenyldicarboxyaldehyde, naphthalenedicarboxyaldehyde, anthracenedicarboxyaldehyde, phenanthrenedicarboxyaldehyde, pyrenedicarboxyaldehyde, benzenetrialdehyde, methylbenzenetrialdehyde, dimethylbenzenetrialdehyde, ethylbenzenetrialdehyde, propylbenzenetrialdehyde, butylbenzenetrialdehyde, cyclohexylbenzenetrialdehyde, biphenyltricarboxyaldehyde, terphenyltricarboxyaldehyde, naphthalenetricarboxyaldehyde, anthracenetricarboxyaldehyde, phenanthrenetricarboxyaldehyde, or pyrenetricarboxyaldehyde having an aromatic ring is preferable from the viewpoint of heat resistance. Among them, benzaldehyde, biphenylcarboxyaldehyde, terphenylcarboxyaldehyde, naphthalenecarboxyaldehyde, anthracenecarboxyaldehyde, phenanthrenecarboxyaldehyde, pyrenecarboxyaldehyde, benzenedialdehyde, biphenyldicarboxyaldehyde, terphenyldicarboxyaldehyde, naphthalenedicarboxyaldehyde, anthracenedicarboxyaldehyde, phenanthrenedicarboxyaldehyde, or pyrenedicarboxyaldehyde is particularly preferable.

The aldehyde of 1 to 19 carbon atoms is easily available as an industrial product or a reagent. One type or two or more types can be used as the aldehyde of 1 to 19 carbon atoms.

The (meth)acryloyl group introducing agent used in the present embodiment is used without particular limitations as long as the compound can replace a hydrogen atom of a hydroxy group in the compound represented by the formula (2') with a (meth)acryloyl group represented by the formula (6) given below. Examples of such a compound include (meth)acryloyl acid chloride, (meth)acryloyl acid bromide, and (meth)acryloyl acid iodide. One type or two or more types can be used as the (meth)acryloyl group introducing agent.

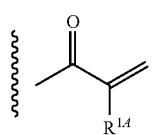

(6)

wherein $R^{1.4}$ is a methyl group or a hydrogen atom.

The basic catalyst used in the reaction of the compound of the general formula (2') of the present embodiment with the (meth)acryloyl group introducing agent can be arbitrarily selected from well-known basic catalysts. Examples thereof include: inorganic bases such as metal hydroxides (e.g., alkali metal or alkaline earth metal hydroxides such as sodium hydroxide and potassium hydroxide), metal carbonates (e.g., alkali metal or alkaline earth metal carbonates such as sodium carbonate and potassium carbonate), and alkali metal or alkaline earth metal bicarbonates such as sodium bicarbonate and potassium bicarbonate; and organic bases such as amines (e.g., tertiary amines (trialkylamines such as triethylamine, aromatic tertiary amines such as N,N-dimethylaniline, and heterocyclic tertiary amines such as 1-methylimidazole), and carboxylic acid metal salts (e.g., acetic acid alkali metal or alkaline earth metal salts such as sodium acetate and calcium acetate). Sodium carbonate or potassium carbonate is preferable from the viewpoint of production such as easy availability and handleability. One type or two or more types can be used as the basic catalyst.

Next, conditions for the reaction of the compound represented by the formula (2') with the (meth)acryloyl group introducing agent will be described in detail.

The reaction proceeds by using 1 mol to an excess of the (meth)acryloyl group introducing agent and 0.001 to 1 mol of the basic catalyst based on 1 mol of the compound represented by the formula (2'), and reacting them at 20 to 150° C. at normal pressure for about 20 minutes to 100 hours. The target component can be isolated by a publicly known method after the reaction. Examples thereof include a method which involves cooling the reaction solution in ice water or the like to precipitate crystals, which are then isolated to obtain crude crystals.

Subsequently, the crude crystals are dissolved in an organic solvent. To the solution, a strong base is added, and the mixture is reacted at 20 to 150° C. at normal pressure for about 20 minutes to 100 hours. The target component can be isolated by a publicly known method after the reaction. Examples thereof include a method which involves concentrating the reaction solution, precipitating the reaction product by the addition of pure water, cooling the reaction solution to room temperature, then separating the precipitates by filtration, filtering and drying the obtained solid matter, then separating and purifying the solid matter from by-products by column chromatography, and distilling off the solvent, followed by filtration and drying to obtain the target compound represented by the formula (1').

[Resin Having Constituent Unit Derived from Compound Represented by Formula (A)]

The resin of the present embodiment is a resin having a constituent unit derived from the compound represented by the above formula (A) (hereinafter, also referred to as "compound of the present embodiment"). The compound represented by the above formula (A) can be used directly as a film forming composition for lithography or the like. The compound represented by the above formula (A) can also be used in the resin having a constituent unit derived from the compound represented by the above formula (A). The resin having a constituent unit derived from the compound represented by the formula (A) includes a resin having a constituent unit derived from the compound represented by the formula (1), a resin having a constituent unit derived from the compound represented by the formula (1'), a resin having a constituent unit derived from the compound represented by the formula (4), a resin having a constituent unit derived from the compound represented by the formula (4'), and a resin having a constituent unit derived from the compound represented by the formula (7). Hereinafter, the "compound represented by the formula (A)" can be used interchangeably with the "compound represented by the formula (1)", the "compound represented by the formula (1')", the "compound represented by the formula (4)", the "compound represented by the formula (4')", or the "compound represented by the formula (7)".

The resin of the present embodiment is obtained by, for example, reacting the compound represented by the above formula (A) with a crosslinking compound.

As the crosslinking compound, a publicly known monomer can be used without particular limitations as long as it can oligomerize or polymerize the compound represented by the above formula (A). Specific examples thereof include, but not particularly limited to, aldehydes, ketones, carboxylic acids, carboxylic acid halides, halogen-containing compounds, amino compounds, imino compounds, isocyanates, and unsaturated hydrocarbon group-containing compounds.

Specific examples of the resin according to the present embodiment include resins that are made novolac by, for example, a condensation reaction between the compound represented by the above formula (A) with an aldehyde that is a crosslinking compound.

Herein, examples of the aldehyde used when making the compound represented by the above formula (A) novolac include, but not particularly limited to, formaldehyde, trioxane, paraformaldehyde, benzaldehyde, acetaldehyde, propylaldehyde, phenylacetaldehyde, phenylpropylaldehyde, hydroxybenzaldehyde, chlorobenzaldehyde, nitrobenzaldehyde, methylbenzaldehyde, ethylbenzaldehyde, butylbenzaldehyde, biphenylaldehyde, naphthaldehyde, anthracenecarboaldehyde, phenanthrenecarboaldehyde, pyrenecarboaldehyde, and furfural. Among these, formaldehyde is more preferable. These aldehydes can be used alone as one kind or may be used in combination of two or more kinds. The amount of the above aldehydes used is not particularly limited, but is preferably 0.2 to 5 mol and more preferably 0.5 to 2 mol based on 1 mol of the compound represented by the above formula (A).

An acid catalyst can also be used in the condensation reaction between the compound represented by the above formula (A) and the aldehyde. The acid catalyst used herein can be arbitrarily selected and used from publicly known catalysts and is not particularly limited. Inorganic acids, organic acids, Lewis acids, and solid acids are widely known as such acid catalysts, and examples include, but not particularly limited to, inorganic acids such as hydrochloric acid, sulfuric acid, phosphoric acid, hydrobromic acid, and hydrofluoric acid; organic acids such as oxalic acid, malonic acid, succinic acid, adipic acid, sebacic acid, citric acid, fumaric acid, maleic acid, formic acid, p-toluenesulfonic acid, methanesulfonic acid, trifluoroacetic acid, dichloroacetic acid, trichloroacetic acid, trifluoromethanesulfonic acid, benzenesulfonic acid, naphthalenesulfonic acid, and naphthalenedisulfonic acid; Lewis acids such as zinc chloride, aluminum chloride, iron chloride, and boron trifluoride; and solid acids such as tungstosilicic acid, tungstophosphoric acid, silicomolybdic acid, and phosphomolybdic acid. Among them, organic acids and solid acids are preferable from the viewpoint of production, and hydrochloric acid or sulfuric acid is preferable from the viewpoint of production such as easy availability and handleability. The acid catalysts can be used alone as one kind, or can be used in combination of two or more kinds.

Also, the amount of the acid catalyst used can be arbitrarily set according to, for example, the kind of the raw materials used and the catalyst used and moreover the reaction conditions and is not particularly limited, but is preferably 0.01 to 100 parts by mass based on 100 parts by mass of the reaction raw materials.

The aldehyde is not necessarily needed in the case of a copolymerization reaction with a compound having a non-conjugated double bond, such as indene, hydroxyindene, benzofuran, hydroxyanthracene, acenaphthylene, biphenyl, bisphenol, trisphenol, dicyclopentadiene, tetrahydroindene, 4-vinylcyclohexene, norbornadiene, 5-vinylnorborn-2-ene, α-pinene, β-pinene, and limonene, as the crosslinking compound.

A reaction solvent can also be used in the condensation reaction between the compound represented by the above formula (A) and the aldehyde. The reaction solvent in the polycondensation can be arbitrarily selected and used from publicly known solvents and is not particularly limited, and examples include water, methanol, ethanol, propanol, butanol, tetrahydrofuran, dioxane, or a mixed solvent thereof. The reaction solvents can be used alone as one kind, or can be used in combination of two or more kinds.

Also, the amount of these reaction solvents used can be arbitrarily set according to, for example, the kind of the raw materials used and the catalyst used and moreover the reaction conditions and is not particularly limited, but is preferably in the range of 0 to 2000 parts by mass based on 100 parts by mass of the reaction raw materials. Furthermore, the reaction temperature can be arbitrarily selected according to the reactivity of the reaction raw materials and is not particularly limited, but is usually within the range of 10 to 200° C. The reaction method can be arbitrarily selected and used from publicly known approaches and is not particularly limited, and there are a method of charging the compound represented by the above formula (A), the aldehyde, and the catalyst in one portion, and a method of dropping the compound represented by the above formula (A) and the aldehyde in the presence of the catalyst.

After the polycondensation reaction terminates, isolation of the obtained resin can be carried out according to a conventional method, and is not particularly limited. For example, by adopting a commonly used approach in which the temperature of the reaction vessel is elevated to 130 to 230° C. in order to remove unreacted raw materials, catalyst, etc. present in the system, and volatile portions are removed at about 1 to 50 mmHg, a novolac resin that is the target compound can be obtained.

Herein, the resin according to the present embodiment may be a homopolymer of a compound represented by the above formula (A), or may be a copolymer with a further phenol. Herein, examples of the copolymerizable phenol include, but not particularly limited to, phenol, cresol, dimethylphenol, trimethylphenol, butylphenol, phenylphenol, diphenylphenol, naphthylphenol, resorcinol, methylresorcinol, catechol, butylcatechol, methoxyphenol, methoxyphenol, propylphenol, pyrogallol, and thymol.

The resin according to the present embodiment may be a copolymer with a polymerizable monomer other than the above-described further phenols. Examples of such a copolymerization monomer include, but not particularly limited to, naphthol, methylnaphthol, methoxynaphthol, dihydroxynaphthalene, indene, hydroxyindene, benzofuran, hydroxyanthracene, acenaphthylene, biphenyl, bisphenol, trisphenol, dicyclopentadiene, tetrahydroindene, 4-vinylcyclohexene, norbornadiene, vinylnorbornene, pinene, and limonene. The resin according to the present embodiment may be a copolymer of two or more components (for example, a binary to quaternary system) composed of the compound represented by the above formula (A) and the above-described phenol, may be a copolymer of two or more components (for example, a binary to quaternary system) composed of the compound represented by the above formula (A) and the above-described copolymerization monomer, or may be a copolymer of three or more components (for example, a tertiary to quaternary system) composed of the compound represented by the above formula (A), the above-described phenol, and the above-described copolymerization monomer.

The molecular weight of the resin according to the present embodiment is not particularly limited, and the weight average molecular weight (Mw) in terms of polystyrene is preferably 500 to 30,000 and more preferably 750 to 20,000. The resin according to the present embodiment preferably has dispersibility (weight average molecular weight Mw/number average molecular weight Mn) within the range of 1.2 to 7 from the viewpoint of enhancing crosslinking efficiency while suppressing volatile components during baking. The above Mn can be determined by a method described in Examples mentioned later.

[Composition]

The composition of the present embodiment contains one or more selected from the group consisting of the compound represented by the above formula (A) and the resin having a constituent unit derived from the compound. Also, the composition of the present embodiment may contain both of the compound of the present embodiment and the resin of the present embodiment. Hereinafter, the "one or more selected from the group consisting of the compound represented by the above formula (A) and the resin having a constituent unit derived from the compound" is also referred to as "compound and/or resin of the present embodiment" or "component (A)".

[Composition for Forming Optical Component]

The composition for forming optical component of the present embodiment contains one or more selected from the group consisting of the compound represented by the above formula (A) and the resin having a constituent unit derived from the compound. Also, the composition for forming optical component of the present embodiment may contain both of the compound of the present embodiment and the resin of the present embodiment. Herein, the "optical component" refers to a component in the form of a film or a sheet as well as a plastic lens (a prism lens, a lenticular lens, a microlens, a Fresnel lens, a viewing angle control lens, a contrast improving lens, etc.), a phase difference film, a film for electromagnetic wave shielding, a prism, an optical fiber, a solder resist for flexible printed wiring, a plating resist, an interlayer insulating film for multilayer printed circuit boards, or a photosensitive optical waveguide. The compound and the resin of the present invention are useful for forming these optical components.

[Film Forming Composition for Lithography]

The film forming composition for lithography of the present embodiment contains one or more selected from the group consisting of the compound represented by the above formula (A) and the resin having a constituent unit derived from the compound. Also, the film forming composition for lithography of the present embodiment may contain both of the compound of the present embodiment and the resin of the present embodiment.

[Resist Composition]

The resist composition of the present embodiment contains one or more selected from the group consisting of the compound represented by the above formula (A) and the resin having a constituent unit derived from the compound. Also, the resist composition of the present embodiment may contain both of the compound of the present embodiment and the resin of the present embodiment.

It is preferable that the resist composition of the present embodiment should contain a solvent. Examples of the solvent can include, but not particularly limited to, ethylene glycol monoalkyl ether acetates such as ethylene glycol monomethyl ether acetate, ethylene glycol monoethyl ether acetate, ethylene glycol mono-n-propyl ether acetate, and ethylene glycol mono-n-butyl ether acetate; ethylene glycol monoalkyl ethers such as ethylene glycol monomethyl ether and ethylene glycol monoethyl ether; propylene glycol monoalkyl ether acetates such as propylene glycol monomethyl ether acetate (PGMEA), propylene glycol monoethyl ether acetate, propylene glycol mono-n-propyl ether acetate, and propylene glycol mono-n-butyl ether acetate; propylene glycol monoalkyl ethers such as propylene glycol monomethyl ether (PGME) and propylene glycol monoethyl ether; ester lactates such as methyl lactate, ethyl lactate, n-propyl lactate, n-butyl lactate, and n-amyl lactate; aliphatic carboxylic acid esters such as methyl acetate, ethyl acetate, n-propyl acetate, n-butyl acetate, n-amyl acetate, n-hexyl acetate, methyl propionate, and ethyl propionate; other esters such as methyl 3-methoxypropionate, ethyl 3-methoxypropionate, methyl 3-ethoxypropionate, ethyl 3-ethoxypropionate, methyl 3-methoxy-2-methylpropionate, 3-methoxybutylacetate, 3-methyl-3-methoxybutylacetate, butyl 3-methoxy-3-methylpropionate, butyl 3-methoxy-3-methylbutyrate, methyl acetoacetate, methyl pyruvate, and ethyl pyruvate; aromatic hydrocarbons such as toluene and xylene; ketones such as 2-heptanone, 3-heptanone, 4-heptanone, cyclopentanone (CPN), and cyclohexanone (CHN); amides such as N,N-dimethylformamide, N-methylacetamide, N,N-dimethylacetamide, and N-methylpyrrolidone; and lactones such as γ-lactone. These solvents can be used alone or in combination of two or more kinds.

The solvent used in the present embodiment is preferably a safe solvent, more preferably at least one selected from PGMEA, PGME, CHN, CPN, 2-heptanone, anisole, butyl acetate, ethyl propionate, and ethyl lactate, and still more preferably at least one selected from PGMEA, PGME, and CHN.

In the present embodiment, the amount of the solid component and the amount of the solvent are not particularly limited, but preferably the solid component is 1 to 80% by mass and the solvent is 20 to 99% by mass, more preferably the solid component is 1 to 50% by mass and the solvent is 50 to 99% by mass, still more preferably the solid component is 2 to 40% by mass and the solvent is 60 to 98% by mass, and particularly preferably the solid component is 2 to 10% by mass and the solvent is 90 to 98% by mass, based on 100% by mass of the total mass of the amount of the solid component and the solvent.

The resist composition of the present embodiment may contain at least one selected from the group consisting of an acid generating agent (C), an acid crosslinking agent (G), an acid diffusion controlling agent (E), and a further component (F), as other solid components. In the present specification, the solid components refer to components except for the solvent.

Hereinafter, the acid generating agent (C), the acid crosslinking agent (G), the acid diffusion controlling agent (E), and the further component (F) will be described.

[Acid Generating Agent (C)]

The resist composition of the present embodiment preferably contains one or more acid generating agents (C) generating an acid directly or indirectly by irradiation of any radiation selected from visible light, ultraviolet, excimer laser, electron beam, extreme ultraviolet (EUV), X-ray, and ion beam. The acid generating agent (C) is not particularly limited, and, for example, an acid generating agent described in International Publication No. WO2013/024778 can be used. The acid generating agent (C) can be used alone or in combination of two or more kinds.

The amount of the acid generating agent (C) used is preferably 0.001 to 49% by mass of the total weight of the solid components, more preferably 1 to 40% by mass, still more preferably 3 to 30% by mass, and particularly preferably 10 to 25% by mass. By using the acid generating agent (C) within the above range, a pattern profile with high sensitivity and low edge roughness is obtained. In the present embodiment, the acid generation method is not particularly limited as long as an acid is generated in the system. By using excimer laser instead of ultraviolet such as g-ray and i-ray, finer processing is possible, and also by using electron beam, extreme ultraviolet, X-ray or ion beam as a high energy ray, further finer processing is possible.

[Acid Crosslinking Agent (G)]

In the present embodiment, the resist composition preferably contains one or more acid crosslinking agents (G). The acid crosslinking agent (G) is a compound capable of intramolecular or intermolecular crosslinking the component (A) in the presence of the acid generated from the acid generating agent (C). Examples of such an acid crosslinking agent (G) include a compound having one or more groups (hereinafter, referred to as "crosslinkable group") capable of crosslinking the component (A).

Examples of such a crosslinkable group can include (i) a hydroxyalkyl group such as a hydroxy (C1-C6 alkyl group), a C1-C6 alkoxy (C1-C6 alkyl group), and an acetoxy (C1-C6 alkyl group), or a group derived therefrom; (ii) a carbonyl group such as a formyl group and a carboxy (C1-C6 alkyl group), or a group derived therefrom; (iii) a nitrogenous group-containing group such as a dimethylaminomethyl group, a diethylaminomethyl group, a dimethylolaminomethyl group, a diethylolaminomethyl group, and a morpholinomethyl group; (iv) a glycidyl group-containing group such as a glycidyl ether group, a glycidyl ester group, and a glycidylamino group; (v) a group derived from an aromatic group such as a C1-C6 allyloxy (C1-C6 alkyl group) and a C1-C6 aralkyloxy (C1-C6 alkyl group) such as a benzyloxymethyl group and a benzoyloxymethyl group; and (vi) a polymerizable multiple bond-containing group such as a vinyl group and a isopropenyl group. As the crosslinkable group of the acid crosslinking agent (G), a hydroxyalkyl group and an alkoxyalkyl group or the like are preferable, and an alkoxymethyl group is particularly preferable.

The acid crosslinking agent (G) having the above crosslinkable group is not particularly limited, and, for example, an acid crosslinking agent described in International Publication No. WO2013/024778 can be used. The acid crosslinking agent (G) can be used alone or in combination of two or more kinds.

In the present embodiment, the amount of the acid crosslinking agent (G) used is preferably 0.5 to 49% by mass of the total weight of the solid components, more preferably 0.5 to 40% by mass, still more preferably 1 to 30% by mass, and particularly preferably 2 to 20% by mass. When the content ratio of the above acid crosslinking agent (G) is 0.5% by mass or more, the inhibiting effect of the solubility of a resist film in an alkaline developing solution is improved, and a decrease in the film remaining rate, and occurrence of swelling and meandering of a pattern can be inhibited, which is preferable. On the other hand, when the content is 49% by mass or less, a decrease in heat resistance as a resist can be inhibited, which is preferable.

[Acid Diffusion Controlling Agent (E)]

In the present embodiment, the resist composition may contain an acid diffusion controlling agent (E) having a function of controlling diffusion of an acid generated from an acid generating agent by radiation irradiation in a resist film to inhibit any unpreferable chemical reaction in an unexposed region or the like. By using such an acid diffusion controlling agent (E), the storage stability of a resist composition is improved. Also, along with the improvement of the resolution, the line width change of a resist pattern due to variation in the post exposure delay time before radiation irradiation and the post exposure delay time after radiation irradiation can be inhibited, and the composition has extremely excellent process stability. Such an acid diffusion controlling agent (E) is not particularly limited, and examples include a radiation degradable basic compound such as a nitrogen atom-containing basic compound, a basic sulfonium compound, and a basic iodonium compound.

The above acid diffusion controlling agent (E) is not particularly limited, and, for example, an acid diffusion controlling agent described in International Publication No. WO2013/024778 can be used. The acid diffusion controlling agent (E) can be used alone or in combination of two or more kinds.

The content of the acid diffusion controlling agent (E) is preferably 0.001 to 49% by mass of the total weight of the solid component, more preferably 0.01 to 10% by mass, still more preferably 0.01 to 5% by mass, and particularly preferably 0.01 to 3% by mass. Within the above range, a decrease in resolution, and deterioration of the pattern shape and the dimension fidelity or the like can be prevented. Moreover, even though the post exposure delay time from electron beam irradiation to heating after radiation irradiation becomes longer, the shape of the pattern upper layer portion does not deteriorate. When the content is 10% by mass or less, a decrease in sensitivity, and developability of the unexposed portion or the like can be prevented. By using such an acid diffusion controlling agent, the storage stability of a resist composition improves, also along with improvement of the resolution, the line width change of a resist pattern due to variation in the post exposure delay time before radiation irradiation and the post exposure delay time after radiation irradiation can be inhibited, and the composition is extremely excellent process stability.

[Further Component (F)]

To the resist composition of the present embodiment, if required, as the further component (F), one kind or two kinds or more of various additive agents such as a dissolution promoting agent, a dissolution controlling agent, a sensitizing agent, a surfactant, and an organic carboxylic acid or an oxo acid of phosphor or derivative thereof can be added.

[Dissolution Promoting Agent]

A low molecular weight dissolution promoting agent is a component having a function of increasing the solubility of a compound represented by the formula (A) in a developing solution to moderately increase the dissolution rate of the compound upon developing, when the solubility of the compound is too low. The low molecular weight dissolution promoting agent can be used, if required. Examples of the above dissolution promoting agent can include low molecular weight phenolic compounds, such as bisphenols and tris(hydroxyphenyl)methane. These dissolution promoting agents can be used alone or in mixture of two or more kinds.

The content of the dissolution promoting agent, which is arbitrarily adjusted according to the kind of the compound to be used, is preferably 0 to 49% by mass of the total weight of the solid component, more preferably 0 to 5% by mass, still more preferably 0 to 1% by mass, and particularly preferably 0% by mass.

[Dissolution Controlling Agent]

The dissolution controlling agent is a component having a function of controlling the solubility of the compound represented by the formula (A) in a developing solution to moderately decrease the dissolution rate upon developing, when the solubility of the compound is too high. As such a dissolution controlling agent, the one which does not chemically change in steps such as calcination of resist coating, radiation irradiation, and development is preferable.

The dissolution controlling agent is not particularly limited, and examples can include aromatic hydrocarbons such as phenanthrene, anthracene, and acenaphthene; ketones such as acetophenone, benzophenone, and phenyl naphthyl ketone; and sulfones such as methyl phenyl sulfone, diphenyl sulfone, and dinaphthyl sulfone. These dissolution controlling agents can be used alone or in two or more kinds.

The content of the dissolution controlling agent, which is arbitrarily adjusted according to the kind of the compound to be used, is preferably 0 to 49% by mass of the total weight of the solid component, more preferably 0 to 5% by mass, still more preferably 0 to 1% by mass, and particularly preferably 0% by mass.

[Sensitizing Agent]

The sensitizing agent is a component having a function of absorbing irradiated radiation energy, transmitting the energy to the acid generating agent (C), and thereby increasing the acid production amount, and improving the apparent sensitivity of a resist. Such a sensitizing agent is not particularly limited, and examples can include benzophenones, biacetyls, pyrenes, phenothiazines, and fluorenes. These sensitizing agents can be used alone or in two or more kinds.

The content of the sensitizing agent, which is arbitrarily adjusted according to the kind of the compound to be used, is preferably 0 to 49% by mass of the total weight of the solid component, more preferably 0 to 5% by mass, still more preferably 0 to 1% by mass, and particularly preferably 0% by mass.

[Surfactant]

The surfactant is a component having a function of improving coatability and striation of the resist composition of the present embodiment, and developability of a resist or the like. Such a surfactant may be any of anionic, cationic, nonionic, and amphoteric surfactants. A preferable surfactant is a nonionic surfactant. The nonionic surfactant has a good affinity with a solvent used in production of resist compositions and more effects. Examples of the nonionic surfactant include, but not particularly limited to, a polyoxyethylene higher alkyl ethers, polyoxyethylene higher alkyl phenyl ethers, and higher fatty acid diesters of polyethylene glycol. Examples of commercially available products include, hereinafter by trade name, EFTOP (manufactured by Jemco Inc.), MEGAFAC (manufactured by DIC Corporation), Fluorad (manufactured by Sumitomo 3M Limited), AsahiGuard, Surflon (hereinbefore, manufactured by Asahi Glass Co., Ltd.), Pepole (manufactured by Toho Chemical Industry Co., Ltd.), KP (manufactured by Shin-Etsu Chemical Co., Ltd.), and Polyflow (manufactured by Kyoeisha Chemical Co., Ltd.).

The content of the surfactant, which is arbitrarily adjusted according to the kind of the compound to be used, is preferably 0 to 49% by mass of the total weight of the solid component, more preferably 0 to 5% by mass, still more preferably 0 to 1% by mass, and particularly preferably 0% by mass.

[Organic Carboxylic Acid or Oxo Acid of Phosphor or Derivative Thereof]

For the purpose of prevention of sensitivity deterioration or improvement of a resist pattern shape and post exposure delay stability or the like, and as an additional optional component, the resist composition of the present embodiment can contain an organic carboxylic acid or an oxo acid of phosphor or derivative thereof. The organic carboxylic acid or the oxo acid of phosphor or derivative thereof can be used in combination with the acid diffusion controlling agent, or may be used alone. The organic carboxylic acid is, for example, suitably malonic acid, citric acid, malic acid, succinic acid, benzoic acid, salicylic acid, or the like. Examples of the oxo acid of phosphor or derivative thereof include phosphoric acid or derivative thereof such as ester including phosphoric acid, di-n-butyl ester phosphate, and diphenyl ester phosphate; phosphonic acid or derivative thereof such as ester including phosphonic acid, dimethyl ester phosphonate, di-n-butyl ester phosphonate, phenylphosphonic acid, diphenyl ester phosphonate, and dibenzyl ester phosphonate; and phosphinic acid and derivative thereof such as ester including phosphinic acid and phenylphosphinic acid. Among these, phosphonic acid is particularly preferable.

The organic carboxylic acid or the oxo acid of phosphor or derivative thereof can be used alone or in combination of two or more kinds. The content of the organic carboxylic acid or the oxo acid of phosphor or derivative thereof, which is arbitrarily adjusted according to the kind of the compound to be used, is preferably 0 to 49% by mass of the total weight of the solid component, more preferably 0 to 5% by mass, still more preferably 0 to 1% by mass, and particularly preferably 0% by mass.

[Further Additive Agent Other than Above Additive Agents (Dissolution Promoting Agent, Dissolution Controlling Agent, Sensitizing Agent, Surfactant, and Organic Carboxylic Acid or Oxo Acid of Phosphor or Derivative Thereof)]

Furthermore, the resist composition of the present embodiment can contain one kind or two kinds or more of additive agents other than the above dissolution controlling agent, sensitizing agent, surfactant, and organic carboxylic acid or oxo acid of phosphor or derivative thereof if required. Examples of such an additive agent include a dye, a pigment, and an adhesion aid. For example, the composition contains the dye or the pigment, and thereby a latent image of the exposed portion is visualized and influence of halation upon exposure can be alleviated, which is preferable. The composition contains the adhesion aid, and thereby adhesiveness to a substrate can be improved, which is preferable. Furthermore, examples of other additive agent can include a halation preventing agent, a storage stabilizing agent, a defoaming agent, and a shape improving agent. Specific examples thereof can include 4-hydroxy-4'-methylchalkone.

In the resist composition of the present embodiment, the total content of the optional component (F) is preferably 0 to 99% by mass of the total weight of the solid component, more preferably 0 to 49% by mass, still more preferably 0 to 10% by mass, further preferably 0 to 5% by mass, still further preferably 0 to 1% by mass, and particularly preferably 0% by mass.

[Content Ratio of Each Component]

In the resist composition of the present embodiment, the content of the compound and/or the resin of the present embodiment is not particularly limited, but is preferably 50 to 99.4% by mass of the total mass of the solid components (summation of solid components including the compound represented by the formula (A), the resin having the compound represented by the formula (A) as a constituent, and optionally used components such as acid generating agent (C), acid crosslinking agent (G), acid diffusion controlling agent (E), and further component (F) (also referred to as "optional component (F)"), hereinafter the same), more preferably 55 to 90% by mass, still more preferably 60 to 80% by mass, and particularly preferably 60 to 70% by mass. In the case of the above content, resolution is further improved, and line edge roughness (LER) is further decreased. When both the compound and the resin of the present embodiment are contained, the above content refers to the total amount of the compound and the resin of the present embodiment.

In the resist composition of the present embodiment, the content ratio of the compound and/or the resin of the present embodiment (component (A)), the acid generating agent (C), the acid crosslinking agent (G), the acid diffusion controlling agent (E), and the optional component (F) (the component (A)/the acid generating agent (C)/the acid crosslinking agent (G)/the acid diffusion controlling agent (E)/the optional component (F)) is preferably 50 to 99.4% by mass/0.001 to 49% by mass/0.5 to 49% by mass/0.001 to 49% by mass/0 to 49% by mass based on 100% by mass of the solid components of the resist composition, more preferably 55 to 90% by mass/1 to 40% by mass/0.5 to 40% by mass/0.01 to 10% by mass/0 to 5% by mass, still more preferably 60 to 80% by mass/3 to 30% by mass/1 to 30% by mass/0.01 to 5% by mass/0 to 1% by mass, and particularly preferably 60 to 70% by mass/10 to 25% by mass/2 to 20% by mass/0.01 to 3% by mass/0% by mass. The content ratio of each component is selected from each range so that the summation thereof is 100% by mass. By the above content ratio, performance such as sensitivity, resolution, and developability is excellent. The "solid components" refer to components except for the solvent. "100% by mass of the solid components" refer to 100% by mass of the components except for the solvent.

The resist composition of the present embodiment is generally prepared by dissolving each component in a solvent upon use into a homogeneous solution, and then if required, filtering through a filter or the like with a pore diameter of about 0.2 μm, for example.

The resist composition of the present embodiment can contain an additional resin other than the resin of the present embodiment, if required. Examples of the resin include, but not particularly limited to, a novolac resin, polyvinyl phenols, polyacrylic acid, polyvinyl alcohol, a styrene-maleic anhydride resin, and polymers containing an acrylic acid, vinyl alcohol or vinylphenol as a monomeric unit, and derivatives thereof. The content of the resin is not particularly limited and is arbitrarily adjusted according to the kind of the component (A) to be used, and is preferably 30 parts by mass or less per 100 parts by mass of the component (A), more preferably 10 parts by mass or less, still more preferably 5 parts by mass or less, and particularly preferably 0 part by mass.

[Physical Properties and the Like of Resist Composition]

The resist composition of the present embodiment can form an amorphous film by spin coating. Also, the resist composition of the present embodiment can be applied to a general semiconductor production process. Any of positive type and negative type resist patterns can be individually prepared depending on the kind of a developing solution to be used.

In the case of a positive type resist pattern, the dissolution rate of the amorphous film formed by spin coating with the resist composition of the present embodiment in a developing solution at 23° C. is preferably 5 angstrom/sec or less, more preferably 0.05 to 5 angstrom/sec, and still more preferably 0.0005 to 5 angstrom/sec. When the dissolution rate is 5 angstrom/sec or less, the above portion is insoluble in a developing solution, and thus the amorphous film can form a resist. When the amorphous film has a dissolution rate of 0.0005 angstrom/sec or more, the resolution may improve. It is presumed that this is because due to the change in the solubility before and after exposure of the component (A), contrast at the interface between the exposed portion being dissolved in a developing solution and the unexposed portion not being dissolved in a developing solution is increased. Also, there are effects of reducing LER and defects.

In the case of a negative type resist pattern, the dissolution rate of the amorphous film formed by spin coating with the resist composition of the present embodiment in a developing solution at 23° C. is preferably 10 angstrom/sec or more. When the dissolution rate is 10 angstrom/sec or more, the amorphous film more easily dissolves in a developing solution, and is more suitable for a resist. When the amorphous film has a dissolution rate of 10 angstrom/sec or more, the resolution may improve. It is presumed that this is because the micro surface portion of the component (A) dissolves, and LER is reduced. Also, there are effects of reducing defects.

The dissolution rate can be determined by immersing the amorphous film in a developing solution for a predetermined period of time at 23° C. and then measuring the film thickness before and after immersion by a publicly known method such as visual, ellipsometric, or QCM method.

In the case of a positive type resist pattern, the dissolution rate of the portion exposed by radiation such as KrF excimer laser, extreme ultraviolet, electron beam or X-ray, of the amorphous film formed by spin coating with the resist composition of the present embodiment, in a developing solution at 23° C. is preferably 10 angstrom/sec or more. When the dissolution rate is 10 angstrom/sec or more, the amorphous film more easily dissolves in a developing solution, and is more suitable for a resist. When the amorphous film has a dissolution rate of 10 angstrom/sec or more, the resolution may improve. It is presumed that this is because the micro surface portion of the component (A) dissolves, and LER is reduced. Also, there are effects of reducing defects.

In the case of a negative type resist pattern, the dissolution rate of the portion exposed by radiation such as KrF excimer laser, extreme ultraviolet, electron beam or X-ray, of the amorphous film formed by spin coating with the resist composition of the present embodiment, in a developing solution at 23° C. is preferably 5 angstrom/sec or less, more preferably 0.05 to 5 angstrom/sec, and still more preferably 0.0005 to 5 angstrom/sec. When the dissolution rate is 5 angstrom/sec or less, the above portion is insoluble in a developing solution, and thus the amorphous film can form a resist. When the amorphous film has a dissolution rate of 0.0005 angstrom/sec or more, the resolution may improve. It is presumed that this is because due to the change in the solubility before and after exposure of the component (A), contrast at the interface between the unexposed portion being dissolved in a developing solution and the exposed portion not being dissolved in a developing solution is increased. Also, there are effects of reducing LER and defects.

[Film Forming Composition for Lithography]

The resist composition of the present embodiment can also be used as a film forming composition for lithography.

[Radiation-Sensitive Composition]

The radiation-sensitive composition of the present embodiment is a radiation-sensitive composition containing the compound of the present embodiment and/or the resin of the present embodiment (A), an optically active diazonaphthoquinone compound (B), and a solvent, wherein the content of the solvent is 20 to 99% by mass based on 100% by mass in total of the radiation-sensitive composition; and the content of components except for the solvent is 1 to 80% by mass based on 100% by mass in total of the radiation-sensitive composition.

The component (A) to be contained in the radiation-sensitive composition of the present embodiment is used in combination with the optically active diazonaphthoquinone compound (B) mentioned later and is useful as a base material for positive type resists that becomes a compound easily soluble in a developing solution by irradiation with g-ray, h-ray, i-ray, KrF excimer laser, ArF excimer laser, extreme ultraviolet, electron beam, or X-ray. Although the properties of the component (A) are not largely altered by g-ray, h-ray, i-ray, KrF excimer laser, ArF excimer laser, extreme ultraviolet, electron beam, or X-ray, the optically active diazonaphthoquinone compound (B) poorly soluble in a developing solution is converted to an easily soluble compound so that a resist pattern can be formed in a development step.

Since the component (A) to be contained in the radiation-sensitive composition of the present embodiment is a relatively low molecular weight compound as shown in the above formula (A), the obtained resist pattern has very small roughness. In the above formula (A), at least one selected from the group consisting of $R^1$ to $R^5$ is preferably a group containing an iodine atom. In the case of applying the component (A) having such a group containing an iodine atom which is a preferable form to the radiation-sensitive composition of the present embodiment, the ability to absorb radiation such as electron beam, extreme ultraviolet (EUV), or X-ray is increased. As a result, this enables the enhancement of the sensitivity, which is very preferable.

The glass transition temperature of the component (A) to be contained in the radiation-sensitive composition of the present embodiment is preferably 100° C. or higher, more preferably 120° C. or higher, still more preferably 140° C. or higher, and particularly preferably 150° C. or higher. The upper limit of the glass transition temperature of the component (A) is not particularly limited and is, for example, 400° C. When the glass transition temperature of the component (A) falls within the above range, the resulting radiation-sensitive composition has heat resistance capable of maintaining a pattern shape in a semiconductor lithography process, and improves performance such as high resolution.

The heat of crystallization determined by the differential scanning calorimetry of the glass transition temperature of the component (A) to be contained in the radiation-sensitive composition of the present embodiment is preferably less than 20 J/g. (Crystallization temperature)–(Glass transition temperature) is preferably 70° C. or more, more preferably 80° C. or more, still more preferably 100° C. or more, and particularly preferably 130° C. or more. When the heat of crystallization is less than 20 J/g or (Crystallization temperature)–(Glass transition temperature) falls within the above range, the radiation-sensitive composition easily forms an amorphous film by spin coating, can maintain film formability necessary for a resist over a long period, and can improve resolution.

In the present embodiment, the above heat of crystallization, crystallization temperature, and glass transition temperature can be determined by differential scanning calorimetry using "DSC/TA-50WS" manufactured by Shimadzu Corp. For example, about 10 mg of a sample is placed in an unsealed container made of aluminum, and the temperature is raised to the melting point or more at a temperature increase rate of 20° C./min in a nitrogen gas stream (50 mL/min). After quenching, again the temperature is raised to the melting point or more at a temperature increase rate of 20° C./min in a nitrogen gas stream (30 mL/min). After further quenching, again the temperature is raised to 400° C. at a temperature increase rate of 20° C./min in a nitrogen gas stream (30 mL/min). The temperature at the middle point (where the specific heat is changed into the half) of steps in the baseline shifted in a step-like pattern is defined as the glass transition temperature (Tg). The temperature of the subsequently appearing exothermic peak is defined as the crystallization temperature. The heat is determined from the area of a region surrounded by the exothermic peak and the baseline and defined as the heat of crystallization.

The component (A) to be contained in the radiation-sensitive composition of the present embodiment is preferably low sublimable at 100° C. or lower, preferably 120° C. or lower, more preferably 130° C. or lower, still more preferably 140° C. or lower, and particularly preferably 150° C. or lower at normal pressure. The low sublimability means that in thermogravimetry, weight reduction when the resist base material is kept at a predetermined temperature for 10 minutes is 10% or less, preferably 5% or less, more preferably 3% or less, still more preferably 1% or less, and particularly preferably 0.1% or less. The low sublimability can prevent an exposure apparatus from being contaminated by outgassing upon exposure. In addition, a good pattern shape with low roughness can be obtained.

The component (A) to be contained in the radiation-sensitive composition of the present embodiment dissolves at preferably 1% by mass or more, more preferably 5% by mass or more, and still more preferably 10% by mass or more at 23° C. in a solvent that is selected from propylene glycol monomethyl ether acetate (PGMEA), propylene glycol monomethyl ether (PGME), cyclohexanone (CHN), cyclopentanone (CPN), 2-heptanone, anisole, butyl acetate, ethyl propionate, and ethyl lactate and exhibits the highest ability to dissolve the component (A). Particularly preferably, the component (A) dissolves at 20% by mass or more at 23° C. in a solvent that is selected from PGMEA, PGME, and CHN and exhibits the highest ability to dissolve the resist base material (A). Particularly preferably, the component (A) dissolves at 20% by mass or more at 23° C. in PGMEA. When the above conditions are met, the radiation-sensitive composition is easily used in a semiconductor production process at a full production scale.

[Optically Active Diazonaphthoquinone Compound (B)]

The optically active diazonaphthoquinone compound (B) to be contained in the radiation-sensitive composition of the present embodiment is a diazonaphthoquinone substance including a polymer or non-polymer optically active diazonaphthoquinone compound and is not particularly limited as long as it is generally used as a photosensitive component (sensitizing agent) in positive type resist compositions. One kind or two or more kinds can be optionally selected and used.

Such a sensitizing agent is preferably a compound obtained by reacting naphthoquinonediazide sulfonic acid chloride, benzoquinonediazide sulfonic acid chloride, or the like with a low molecular weight compound or a high molecular weight compound having a functional group condensable with these acid chlorides. Herein, examples of the above functional group condensable with the acid chlorides include, but not particularly limited to, a hydroxyl group and an amino group. Particularly, a hydroxyl group is preferable. Examples of the compound containing a hydroxyl group condensable with the acid chlorides can include, but not particularly limited to, hydroquinone, resorcin, hydroxybenzophenones such as 2,4-dihydroxybenzophenone, 2,3,4-trihydroxybenzophenone, 2,4,6-trihydroxybenzophenone, 2,4,4'-trihydroxybenzophenone, 2,3,4,4'-tetrahydroxybenzophenone, 2,2',4,4'-tetrahydroxybenzophenone, and 2,2',3,4,6'-pentahydroxybenzophenone, hydroxyphenylalkanes such as bis(2,4-dihydroxyphenyl)methane, bis(2,3,4-trihydroxyphenyl)methane, and bis(2,4-dihydroxyphenyl)propane, and hydroxytriphenylmethanes such as 4,4',3",4"-tetrahydroxy-3,5,3',5'-tetramethyltriphenylmethane and 4,4',2",3",4"-pentahydroxy-3,5,3',5'-tetramethyltriphenylmethane.

Preferable examples of the acid chloride such as naphthoquinonediazide sulfonic acid chloride or benzoquinonediazide sulfonic acid chloride include 1,2-naphthoquinonediazide-5-sulfonyl chloride and 1,2-naphthoquinonediazide-4-sulfonyl chloride.

The radiation-sensitive composition of the present embodiment is preferably prepared by, for example, dissolving each component in a solvent upon use into a homogeneous solution, and then if required, filtering through a filter or the like with a pore diameter of about 0.2 µm, for example.

[Solvent]

Examples of the solvent that can be used in the radiation-sensitive composition of the present embodiment include, but not particularly limited to, propylene glycol monomethyl ether acetate, propylene glycol monomethyl ether, cyclohexanone, cyclopentanone, 2-heptanone, anisole, butyl acetate, ethyl propionate, and ethyl lactate. Among them, propylene glycol monomethyl ether acetate, propylene glycol monomethyl ether, or cyclohexanone is preferable. The solvent may be used alone as one kind or may be used in combination of two or more kinds.

The content of the solvent is 20 to 99% by mass based on 100% by mass in total of the radiation-sensitive composition, preferably 50 to 99% by mass, more preferably 60 to 98% by mass, and particularly preferably 90 to 98% by mass.

The content of components except for the solvent (solid components) is 1 to 80% by mass based on 100% by mass in total of the radiation-sensitive composition, preferably 1 to 50% by mass, more preferably 2 to 40% by mass, particularly preferably 2 to 10% by mass.

[Properties of Radiation-Sensitive Composition]

The radiation-sensitive composition of the present embodiment can form an amorphous film by spin coating. Also, the radiation-sensitive composition of the present embodiment can be applied to a general semiconductor production process. Any of positive type and negative type resist patterns can be individually prepared depending on the kind of a developing solution to be used.

In the case of a positive type resist pattern, the dissolution rate of the amorphous film formed by spin coating with the radiation-sensitive composition of the present embodiment in a developing solution at 23° C. is preferably 5 angstrom/sec or less, more preferably 0.05 to 5 angstrom/sec, and still more preferably 0.0005 to 5 angstrom/sec. When the dissolution rate is 5 angstrom/sec or less, the above portion is insoluble in a developing solution, and thus the amorphous film can form a resist. When the amorphous film has a dissolution rate of 0.0005 angstrom/sec or more, the resolution may improve. It is presumed that this is because due to the change in the solubility before and after exposure of the component (A), contrast at the interface between the exposed portion being dissolved in a developing solution and the unexposed portion not being dissolved in a developing solution is increased. Also, there are effects of reducing LER and defects.

In the case of a negative type resist pattern, the dissolution rate of the amorphous film formed by spin coating with the radiation-sensitive composition of the present embodiment in a developing solution at 23° C. is preferably 10 angstrom/sec or more. When the dissolution rate is 10 angstrom/sec or more, the amorphous film more easily dissolves in a developing solution, and is more suitable for a resist. When the amorphous film has a dissolution rate of 10 angstrom/sec or more, the resolution may improve. It is presumed that this is because the micro surface portion of the component (A) dissolves, and LER is reduced. Also, there are effects of reducing defects.

The dissolution rate can be determined by immersing the amorphous film in a developing solution for a predetermined period of time at 23° C. and then measuring the film thickness before and after immersion by a publicly known method such as visual, ellipsometric, or QCM method.

In the case of a positive type resist pattern, the dissolution rate of the exposed portion after irradiation with radiation such as KrF excimer laser, extreme ultraviolet, electron beam or X-ray, or after heating at 20 to 500° C., of the amorphous film formed by spin coating with the radiation-sensitive composition of the present embodiment, in a developing solution at 23° C. is preferably 10 angstrom/sec or more, more preferably 10 to 10000 angstrom/sec, and still more preferably 100 to 1000 angstrom/sec. When the dissolution rate is 10 angstrom/sec or more, the amorphous film more easily dissolves in a developing solution, and is more suitable for a resist. When the amorphous film has a dissolution rate of 10000 angstrom/sec or less, the resolution may improve. It is presumed that this is because the micro surface portion of the component (A) dissolves, and LER is reduced. Also, there are effects of reducing defects.

In the case of a negative type resist pattern, the dissolution rate of the exposed portion after irradiation with radiation such as KrF excimer laser, extreme ultraviolet, electron beam or X-ray, or after heating at 20 to 500° C., of the amorphous film formed by spin coating with the radiation-sensitive composition of the present embodiment, in a developing solution at 23° C. is preferably 5 angstrom/sec or less, more preferably 0.05 to 5 angstrom/sec, and still more preferably 0.0005 to 5 angstrom/sec. When the dissolution rate is 5 angstrom/sec or less, the above portion is insoluble in a developing solution, and thus the amorphous film can form a resist. When the amorphous film has a dissolution rate of 0.0005 angstrom/sec or more, the resolution may improve. It is presumed that this is because due to the change in the solubility before and after exposure of the component (A), contrast at the interface between the unexposed portion being dissolved in a developing solution and the exposed portion not being dissolved in a developing solution is increased. Also, there are effects of reducing LER and defects.

[Content Ratio of Each Component]

In the radiation-sensitive composition of the present embodiment, the content of the component (A) is preferably 1 to 99% by mass of the total weight of the solid components (summation of the component (A), the optically active diazonaphthoquinone compound (B), and optionally used solid components such as further component (D), hereinafter the same), more preferably 5 to 95% by mass, still more preferably 10 to 90% by mass, and particularly preferably 25 to 75% by mass. When the content of the component (A) falls within the above range, the radiation-sensitive composition of the present embodiment can produce a pattern with high sensitivity and low roughness.

In the radiation-sensitive composition of the present embodiment, the content of the optically active diazonaphthoquinone compound (B) is preferably 1 to 99% by mass of the total weight of the solid components (summation of the component (A), the optically active diazonaphthoquinone compound (B), and optionally used solid components such as further component (D), hereinafter the same), more preferably 5 to 95% by mass, still more preferably 10 to 90% by mass, and particularly preferably 25 to 75% by mass. When the content of the optically active diazonaphthoquinone compound (B) falls within the above range, the radiation-sensitive composition of the present embodiment can produce a pattern with high sensitivity and low roughness.

[Further Component (D)]

To the radiation-sensitive composition of the present embodiment, if required, as a component other than the component (A) and the optically active diazonaphthoquinone compound (B), one kind or two kinds or more of various additive agents such as the above acid generating agent, acid crosslinking agent, acid diffusion controlling agent, dissolution promoting agent, dissolution controlling agent, sensitizing agent, surfactant, and organic carboxylic acid or oxo acid of phosphor or derivative thereof can be added. In the present specification, the further component (D) is also referred to as an optional component (D).

The content ratio of the component (A), the optically active diazonaphthoquinone compound (B), and the further optional component (D) that may be optionally contained in the radiation-sensitive composition ((A)/(B)/(D)) is preferably 1 to 99% by mass/99 to 1% by mass/0 to 98% by mass based on 100% by mass of the solid components of the radiation-sensitive composition, more preferably 5 to 95% by mass/95 to 5% by mass/0 to 49% by mass, still more preferably 10 to 90% by mass/90 to 10% by mass/0 to 10% by mass, particularly preferably 20 to 80% by mass/80 to 20% by mass/0 to 5% by mass, and most preferably 25 to 75% by mass/75 to 25% by mass/0% by mass.

The content ratio of each component is selected from each range so that the summation thereof is 100% by mass. When the content ratio of each component falls within the above range, the radiation-sensitive composition of the present embodiment is excellent in performance such as sensitivity and resolution, in addition to roughness.

The radiation-sensitive composition of the present embodiment may contain a resin other than the resin of the present embodiment. Examples of such a resin include a novolac resin, polyvinyl phenols, polyacrylic acid, polyvinyl alcohol, a styrene-maleic anhydride resin, and polymers containing an acrylic acid, vinyl alcohol or vinylphenol as a monomeric unit, and derivatives thereof. The content of these resins, which is arbitrarily adjusted according to the kind of the component (A) to be used, is preferably 30 parts by mass or less per 100 parts by mass of the component (A), more preferably 10 parts by mass or less, still more preferably 5 parts by mass or less, and particularly preferably 0 part by mass.

[Method for Producing Amorphous Film]

The method for producing an amorphous film according to the present embodiment comprises the step of forming an amorphous film on a substrate using the above radiation-sensitive composition.

[Resist Pattern Formation Method Using Radiation-Sensitive Composition]

A resist pattern formation method using the radiation-sensitive composition of the present embodiment includes the steps of: forming a resist film on a substrate using the above radiation-sensitive composition; exposing at least a portion of the formed resist film; and developing the exposed resist film, thereby forming a resist pattern. Specifically, the same operation as in the following resist pattern formation method using the resist composition can be performed.

[Resist Pattern Formation Method Using Resist Composition]

A resist pattern formation method using the resist composition of the present embodiment includes the steps of: forming a resist film on a substrate using the above resist composition of the present embodiment; exposing at least a portion of the formed resist film; and developing the exposed resist film, thereby forming a resist pattern. The resist pattern according to the present embodiment can also be formed as an upper layer resist in a multilayer process.

Examples of the resist pattern formation method include, but not particularly limited to, the following methods. A resist film is formed by coating a conventionally publicly known substrate with the above resist composition of the present embodiment using a coating means such as spin coating, flow casting coating, and roll coating. The conventionally publicly known substrate is not particularly limited. For example, a substrate for electronic components, and the one having a predetermined wiring pattern formed thereon, or the like can be exemplified. More specific examples include a substrate made of a metal such as a silicon wafer, copper, chromium, iron and aluminum, and a glass substrate. Examples of a wiring pattern material include copper, aluminum, nickel, and gold. Also if required, the substrate may be a substrate having an inorganic and/or organic film provided thereon. Examples of the inorganic film include an inorganic antireflection film (inorganic BARC). Examples of the organic film include an organic antireflection film (organic BARC). Surface treatment with hexamethylene disilazane or the like may be conducted.

Next, the coated substrate is heated if required. The heating conditions vary according to the compounding composition of the resist composition, or the like, but are preferably 20 to 250° C., and more preferably 20 to 150° C. By heating, the adhesiveness of a resist to a substrate may improve, which is preferable. Then, the resist film is exposed to a desired pattern by any radiation selected from the group consisting of visible light, ultraviolet, excimer laser, electron beam, extreme ultraviolet (EUV), X-ray, and ion beam. The exposure conditions or the like are arbitrarily selected according to the compounding composition of the resist composition, or the like. In the present embodiment, in order to stably form a fine pattern with a high degree of accuracy in exposure, the resist film is preferably heated after radiation irradiation.

Next, by developing the exposed resist film in a developing solution, a predetermined resist pattern is formed. As the developing solution, a solvent having a solubility parameter (SP value) close to that of the component (A) to be used is preferably selected. A polar solvent such as a ketone-based solvent, an ester-based solvent, an alcohol-based solvent, an amide-based solvent, and an ether-based solvent; and a hydrocarbon-based solvent, or an alkaline aqueous solution can be used.

Examples of the ketone-based solvent include 1-octanone, 2-octanone, 1-nonanone, 2-nonanone, acetone, 4-heptanone, 1-hexanone, 2-hexanone, diisobutyl ketone, cyclohexanone, methylcyclohexanone, phenylacetone, methyl ethyl ketone, methyl isobutyl ketone, acetylacetone, acetonylacetone, ionone, diacetonyl alcohol, acetyl carbinol, acetophenone, methyl naphthyl ketone, isophorone, and propylene carbonate.

Examples of the ester-based solvent include methyl acetate, butyl acetate, ethyl acetate, isopropyl acetate, amyl acetate, propylene glycol monomethyl ether acetate, ethylene glycol monoethyl ether acetate, diethylene glycol monobutyl ether acetate, diethylene glycol monoethyl ether acetate, ethyl-3-ethoxypropionate, 3-methoxybutyl acetate, 3-methyl-3-methoxybutyl acetate, methyl formate, ethyl formate, butyl formate, propyl formate, ethyl lactate, butyl lactate, and propyl lactate.

Examples of the alcohol-based solvent include an alcohol such as methyl alcohol, ethyl alcohol, n-propyl alcohol, isopropyl alcohol (2-propanol), n-butyl alcohol, sec-butyl alcohol, tert-butyl alcohol, isobutyl alcohol, n-hexyl alcohol, 4-methyl-2-pentanol, n-heptyl alcohol, n-octyl alcohol, and n-decanol; a glycol-based solvent such as ethylene glycol, diethylene glycol, and triethylene glycol; and a glycol ether-based solvent such as ethylene glycol monomethyl ether, propylene glycol monomethyl ether, ethylene glycol monoethyl ether, propylene glycol monoethyl ether, diethylene glycol monomethyl ether, triethylene glycol monoethyl ether, and methoxymethyl butanol.

Examples of the ether-based solvent include dioxane and tetrahydrofuran in addition to the glycol ether-based solvents.

Examples of the amide-based solvent that can be used include N-methyl-2-pyrrolidone, N,N-dimethylacetamide, N,N-dimethylformamide, phosphoric hexamethyltriamide, and 1,3-dimethyl-2-imidazolidinone.

Examples of the hydrocarbon-based solvent include an aromatic hydrocarbon-based solvent such as toluene and xylene; and an aliphatic hydrocarbon-based solvent such as pentane, hexane, octane, and decane.

A plurality of above solvents may be mixed, or the solvent may be used by mixing the solvent with a solvent other than those described above or water within the range having performance. In order to sufficiently exhibit the effect of the present invention, the water content ratio as the whole developing solution is preferably less than 70% by mass and less than 50% by mass, more preferably less than 30% by mass, and further preferably less than 10% by mass. Particularly preferably, the developing solution is substantially moisture free. That is, the content of the organic solvent in the developing solution is not particularly limited, and is preferably 30% by mass or more and 100% by mass or less based on the total amount of the developing solution, preferably 50% by mass or more and 100% by mass or less, more preferably 70% by mass or more and 100% by mass or less, still more preferably 90% by mass or more and 100% by mass or less, and particularly preferably 95% by mass or more and 100% by mass or less.

Examples of the alkaline aqueous solution include an alkaline compound such as mono-, di- or tri-alkylamines, mono-, di- or tri-alkanolamines, heterocyclic amines, tetramethyl ammonium hydroxide (TMAH), and choline.

Particularly, the developing solution containing at least one kind of solvent selected from a ketone-based solvent, an ester-based solvent, an alcohol-based solvent, an amide-based solvent, and an ether-based solvent improves resist performance such as resolution and roughness of the resist pattern, which is preferable.

The vapor pressure of the developing solution is preferably 5 kPa or less at 20° C., more preferably 3 kPa or less, and particularly preferably 2 kPa or less. The evaporation of the developing solution on the substrate or in a developing cup is inhibited by setting the vapor pressure of the developing solution to 5 kPa or less, to improve temperature uniformity within a wafer surface, thereby resulting in improvement in size uniformity within the wafer surface.

Specific examples having a vapor pressure of 5 kPa or less include a ketone-based solvent such as 1-octanone, 2-octanone, 1-nonanone, 2-nonanone, 4-heptanone, 2-hexanone, diisobutyl ketone, cyclohexanone, methylcyclohexanone, phenylacetone, and methyl isobutyl ketone; an ester-based solvent such as butyl acetate, amyl acetate, propylene glycol monomethyl ether acetate, ethylene glycol monoethyl ether acetate, diethylene glycol monobutyl ether acetate, diethylene glycol monoethyl ether acetate, ethyl-3-ethoxy propionate, 3-methoxy butyl acetate, 3-methyl-3-methoxy butyl acetate, butyl formate, propyl formate, ethyl lactate, butyl lactate, and propyl lactate; an alcohol-based solvent such as n-propyl alcohol, isopropyl alcohol, n-butyl alcohol, sec-butyl alcohol, tert-butyl alcohol, isobutyl alcohol, n-hexyl alcohol, 4-methyl-2-pentanol, n-heptyl alcohol, n-octyl alcohol, and n-decanol; a glycol-based solvent such as ethylene glycol, diethylene glycol, and triethylene glycol; a glycol ether-based solvent such as ethylene glycol monomethyl ether, propylene glycol monoethyl ether, ethylene glycol monoethyl ether, propylene glycol monoethyl ether, diethylene glycol monomethyl ether, triethylene glycol monoethyl ether, and methoxymethyl butanol; an ether-based solvent such as tetrahydrofuran; an amide-based solvent such as N-methyl-2-pyrrolidone, N,N-dimethylacetamide, and N,N-dimethylformamide; an aromatic hydrocarbon-based solvent such as toluene and xylene; and an aliphatic hydrocarbon-based solvent such as octane and decane.

Specific examples having a vapor pressure of 2 kPa or less which is a particularly preferable range include a ketone-based solvent such as 1-octanone, 2-octanone, 1-nonanone, 2-nonanone, 4-heptanone, 2-hexanone, diisobutyl ketone, cyclohexanone, methylcyclohexanone, and phenylacetone; an ester-based solvent such as butyl acetate, amyl acetate, propylene glycol monomethyl ether acetate, ethylene glycol monoethyl ether acetate, diethylene glycol monobutyl ether acetate, diethylene glycol monoethyl ether acetate, ethyl-3-ethoxy propionate, 3-methoxy butyl acetate, 3-methyl-3-methoxy butyl acetate, ethyl lactate, butyl lactate, and propyl lactate; an alcohol-based solvent such as n-butyl alcohol, sec-butyl alcohol, tert-butyl alcohol, isobutyl alcohol, n-hexyl alcohol, 4-methyl-2-pentanol, n-heptyl alcohol, n-octyl alcohol, and n-decanol; a glycol-based solvent such as ethylene glycol, diethylene glycol, and triethylene glycol; a glycol ether-based solvent such as ethylene glycol monomethyl ether, propylene glycol monomethyl ether, ethylene glycol monoethyl ether, propylene glycol monoethyl ether, diethylene glycol monomethyl ether, triethylene glycol monoethyl ether, and methoxymethyl butanol; an amide-based solvent such as N-methyl-2-pyrrolidone, N,N-dimethylacetamide, and N,N-dimethylformamide; an aromatic hydrocarbon-based solvent such as xylene; and an aliphatic hydrocarbon-based solvent such as octane and decane.

To the developing solution, a surfactant can be added in an appropriate amount, if required. The surfactant is not particularly limited but, for example, an ionic or nonionic fluorine-based and/or silicon-based surfactant can be used. Examples of the fluorine-based and/or silicon-based surfactant can include the surfactants described in Japanese Patent Application Laid-Open Nos. 62-36663, 61-226746, 61-226745, 62-170950, 63-34540, 7-230165, 8-62834, 9-54432, and 9-5988, and U.S. Pat. Nos. 5,405,720, 5,360,692, 5,529,881, 5,296,330, 5,436,098, 5,576,143, 5,294,511, and U.S. Pat. No. 5,824,451. The surfactant is preferably a nonionic surfactant. The nonionic surfactant is not particularly limited, but a fluorine-based surfactant or a silicon-based surfactant is further preferably used.

The amount of the surfactant used is usually 0.001 to 5% by mass based on the total amount of the developing solution, preferably 0.005 to 2% by mass, and further preferably 0.01 to 0.5% by mass.

The development method is, for example, a method for dipping a substrate in a bath filled with a developing solution for a fixed time (dipping method), a method for raising a developing solution on a substrate surface by the effect of a surface tension and keeping it still for a fixed time, thereby conducting the development (puddle method), a method for spraying a developing solution on a substrate surface (spraying method), and a method for continuously ejecting a developing solution on a substrate rotating at a constant speed while scanning a developing solution ejecting nozzle at a constant rate (dynamic dispense method), or the like may be applied. The time for conducting the pattern development is not particularly limited, but is preferably 10 seconds to 90 seconds.

After the step of conducting development, a step of stopping the development by the replacement with another solvent may be practiced.

A step of rinsing the resist film with a rinsing solution containing an organic solvent is preferably provided after the development.

The rinsing solution used in the rinsing step after development is not particularly limited as long as the rinsing solution does not dissolve the resist pattern cured by crosslinking. A solution containing a general organic solvent or water may be used as the rinsing solution. As the rinsing solution, a rinsing solution containing at least one kind of organic solvent selected from a hydrocarbon-based solvent, a ketone-based solvent, an ester-based solvent, an alcohol-based solvent, an amide-based solvent, and an ether-based solvent is preferably used. More preferably, after development, a step of rinsing the film by using a rinsing solution containing at least one kind of organic solvent selected from the group consisting of a ketone-based solvent, an ester-based solvent, an alcohol-based solvent and an amide-based solvent is conducted. Still more preferably, after development, a step of rinsing the film by using a rinsing solution containing an alcohol-based solvent or an ester-based solvent is conducted. Still more preferably, after development, a step of rinsing the film by using a rinsing solution containing a monohydric alcohol is conducted. Particularly preferably, after development, a step of rinsing the film by using a rinsing solution containing a monohydric alcohol having 5 or more carbon atoms is conducted. The time for rinsing the pattern is not particularly limited, but is preferably 10 seconds to 90 seconds.

Herein, examples of the monohydric alcohol used in the rinsing step after development include a linear, branched or cyclic monohydric alcohol. Specific examples which can be used in the rinsing step include 1-butanol, 2-butanol, 3-methyl-1-butanol, tert-butyl alcohol, 1-pentanol, 2-pentanol, 1-hexanol, 4-methyl-2-pentanol, 1-heptanol, 1-octanol, 2-hexanol, cyclopentanol, 2-heptanol, 2-octanol, 3-hexanol, 3-heptanol, 3-octanol, and 4-octanol or the like. Particularly preferable examples of monohydric alcohol having 5 or more carbon atoms which can be used include 1-hexanol, 2-hexanol, 4-methyl-2-pentanol, 1-pentanol, and 3-methyl-1-butanol or the like.

A plurality of these components may be mixed, or the component may be used by mixing the component with an organic solvent other than those described above.

The water content ratio in the rinsing solution is preferably 10% by mass or less, more preferably 5% by mass or less, and particularly preferably 3% by mass or less. By setting the water content ratio to 10% by mass or less, better development characteristics can be obtained.

The vapor pressure at 20° C. of the rinsing solution used after development is preferably 0.05 kPa or more and 5 kPa or less, more preferably 0.1 kPa or more and 5 kPa or less, and most preferably 0.12 kPa or more and 3 kPa or less. By setting the vapor pressure of the rinsing solution to 0.05 kPa or more and 5 kPa or less, the temperature uniformity in the wafer surface is enhanced and moreover, swelling due to permeation of the rinsing solution is further inhibited. As a result, the dimensional uniformity in the wafer surface is further improved.

The rinsing solution may also be used after adding an appropriate amount of a surfactant to the rinsing solution.

In the rinsing step, the wafer after development is rinsed using the organic solvent-containing rinsing solution. The method for rinsing treatment is not particularly limited. However, for example, a method for continuously ejecting a rinsing solution on a substrate spinning at a constant speed (spin coating method), a method for dipping a substrate in a bath filled with a rinsing solution for a fixed time (dipping method), and a method for spraying a rinsing solution on a substrate surface (spraying method), or the like can be applied. Above all, it is preferable to conduct the rinsing treatment by the spin coating method and after the rinsing, spin the substrate at a rotational speed of 2,000 rpm to 4,000 rpm, to remove the rinsing solution from the substrate surface.

After forming the resist pattern, a pattern wiring substrate is obtained by etching. Etching can be conducted by a publicly known method such as dry etching using plasma gas, and wet etching with an alkaline solution, a cupric chloride solution, and a ferric chloride solution or the like.

After forming the resist pattern, plating can also be conducted. Examples of the above plating method include copper plating, solder plating, nickel plating, and gold plating.

The remaining resist pattern after etching can be peeled by an organic solvent. Examples of the above organic solvent include PGMEA (propylene glycol monomethyl ether acetate), PGME (propylene glycol monomethyl ether), and EL (ethyl lactate). Examples of the above peeling method include a dipping method and a spraying method. A wiring substrate having a resist pattern formed thereon may be a multilayer wiring substrate, and may have a small diameter through hole.

In the present embodiment, the wiring substrate can also be formed by a method for forming a resist pattern, then depositing a metal in vacuum, and subsequently dissolving the resist pattern in a solution, i.e., a liftoff method.

[Underlayer Film Forming Material for Lithography]

The underlayer film forming material for lithography of the present embodiment contains the compound of the present embodiment and/or the resin of the present embodiment. The content of the compound of the present embodiment and/or the resin of the present embodiment in the underlayer film forming material for lithography is preferably 1 to 100% by mass, more preferably 10 to 100% by mass, still more preferably 50 to 100% by mass, particularly preferably 100% by mass, from the viewpoint of coatability and quality stability.

The underlayer film forming material for lithography of the present embodiment is applicable to a wet process and is excellent in heat resistance and etching resistance. Furthermore, the underlayer film forming material for lithography of the present embodiment employs the above substances and can therefore form an underlayer film that is prevented from deteriorating during high temperature baking and is also excellent in etching resistance against oxygen plasma etching or the like. Moreover, the underlayer film forming material for lithography of the present embodiment is also excellent in adhesiveness to a resist layer and can therefore produce an excellent resist pattern. The underlayer film forming material for lithography of the present embodiment may contain an already known underlayer film forming material for lithography or the like, within the range not deteriorating the effect of the present invention.

[Composition for Underlayer Film Formation for Lithography]

The composition for underlayer film formation for lithography of the present embodiment contains the above underlayer film forming material for lithography and a solvent.

[Solvent]

A publicly known solvent can be arbitrarily used as the solvent in the composition for underlayer film formation for lithography of the present embodiment as long as at least the above component (A) dissolves.

Specific examples of the solvent include, but not particularly limited to: ketone-based solvents such as acetone, methyl ethyl ketone, methyl isobutyl ketone, and cyclohexanone; cellosolve-based solvents such as propylene glycol monomethyl ether and propylene glycol monomethyl ether acetate; ester-based solvents such as ethyl lactate, methyl acetate, ethyl acetate, butyl acetate, isoamyl acetate, ethyl lactate, methyl methoxypropionate, and methyl hydroxyisobutyrate; alcohol-based solvents such as methanol, ethanol, isopropanol, and 1-ethoxy-2-propanol; and aromatic hydrocarbons such as toluene, xylene, and anisole. These solvents can be used alone as one kind or used in combination of two or more kinds.

Among the above solvents, cyclohexanone, propylene glycol monomethyl ether, propylene glycol monomethyl ether acetate, ethyl lactate, methyl hydroxyisobutyrate, or anisole is particularly preferable from the viewpoint of safety.

The content of the solvent is not particularly limited and is preferably 100 to 10,000 parts by mass per 100 parts by mass of the above underlayer film forming material, more preferably 200 to 5,000 parts by mass, and still more preferably 200 to 1,000 parts by mass, from the viewpoint of solubility and film formation.

[Crosslinking Agent]

The composition for underlayer film formation for lithography of the present embodiment may contain a crosslinking agent, if required, from the viewpoint of, for example, suppressing intermixing. The crosslinking agent that may be used in the present embodiment is not particularly limited, and, for example, a crosslinking agent described in International Publication No. WO2013/024779 can be used. In the present embodiment, the crosslinking agent can be used alone or in combination of two or more kinds.

In the composition for underlayer film formation for lithography of the present embodiment, the content of the crosslinking agent is not particularly limited and is preferably 5 to 50 parts by mass per 100 parts by mass of the underlayer film forming material, and more preferably 10 to 40 parts by mass. By the above preferable range, a mixing event with a resist layer tends to be prevented. Also, an antireflection effect is enhanced, and film formability after crosslinking tends to be enhanced.

[Acid Generating Agent]

The composition for underlayer film formation for lithography of the present embodiment may contain an acid generating agent, if required, from the viewpoint of, for example, further accelerating crosslinking reaction by heat. An acid generating agent that generates an acid by thermal decomposition, an acid generating agent that generates an acid by light irradiation, and the like are known, any of which can be used.

The acid generating agent is not particularly limited, and, for example, an acid generating agent described in International Publication No. WO2013/024779 can be used. In the present embodiment, the acid generating agent can be used alone or in combination of two or more kinds.

In the composition for underlayer film formation for lithography of the present embodiment, the content of the acid generating agent is not particularly limited and is preferably 0.1 to 50 parts by mass per 100 parts by mass of the underlayer film forming material, and more preferably 0.5 to 40 parts by mass. By the above preferable range, crosslinking reaction tends to be enhanced by an increased amount of an acid generated. Also, a mixing event with a resist layer tends to be prevented.

[Basic Compound]

The composition for underlayer film formation for lithography of the present embodiment may further contain a basic compound from the viewpoint of, for example, improving storage stability.

The basic compound plays a role as a quencher against acids in order to prevent crosslinking reaction from proceeding due to a trace amount of an acid generated by the acid generating agent. Examples of such a basic compound include, but not particularly limited to, primary, secondary or tertiary aliphatic amines, amine blends, aromatic amines, heterocyclic amines, nitrogen-containing compounds having a carboxy group, nitrogen-containing compounds having a sulfonyl group, nitrogen-containing compounds having a hydroxy group, nitrogen-containing compounds having a hydroxyphenyl group, alcoholic nitrogen-containing compounds, amide derivatives, and imide derivatives.

The basic compound used in the present embodiment is not particularly limited, and, for example, a basic compound described in International Publication No. WO2013/024779 can be used. In the present embodiment, the basic compound can be used alone or in combination of two or more kinds.

In the composition for underlayer film formation for lithography of the present embodiment, the content of the basic compound is not particularly limited and is preferably 0.001 to 2 parts by mass per 100 parts by mass of the underlayer film forming material, and more preferably 0.01 to 1 parts by mass. By the above preferable range, storage stability tends to be enhanced without excessively deteriorating crosslinking reaction.

[Further Additive Agent]

The composition for underlayer film formation for lithography of the present embodiment may also contain an additional resin and/or compound for the purpose of conferring thermosetting properties or controlling absorbance. Examples of such an additional resin and/or compound include, but not particularly limited to, naphthol resin, xylene resin naphthol-modified resin, phenol-modified resin of naphthalene resin, polyhydroxystyrene, dicyclopentadiene resin, resins containing (meth)acrylate, dimethacrylate, trimethacrylate, tetramethacrylate, a naphthalene ring such as vinylnaphthalene or polyacenaphthylene, a biphenyl ring such as phenanthrenequinone or fluorene, or a heterocyclic ring having a heteroatom such as thiophene or indene, and resins containing no aromatic ring; and resins or compounds containing an alicyclic structure, such as rosin-based resin, cyclodextrin, adamantine(poly)ol, tricyclodecane(poly)ol, and derivatives thereof. The composition for underlayer film formation for lithography of the present embodiment may further contain a publicly known additive agent. Examples of the above publicly known additive agent include, but not limited to, ultraviolet absorbers, surfactants, colorants, and nonionic surfactants.

[Method for Forming Underlayer Film for Lithography]

The method for forming an underlayer film for lithography according to the present embodiment includes the step of forming an underlayer film on a substrate using the composition for underlayer film formation for lithography of the present embodiment.

[Resist Pattern Formation Method Using Composition for Underlayer Film Formation for Lithography]

A resist pattern formation method using the composition for underlayer film formation for lithography of the present embodiment has the steps of: forming a underlayer film on a substrate using the composition for underlayer film formation for lithography of the present embodiment (step (A-1)); forming at least one photoresist layer on the underlayer film (step (A-2)); and irradiating a predetermined region of the photoresist layer with radiation for development, thereby forming a resist pattern (step (A-3)).

[Circuit Pattern Formation Method Using Composition for Underlayer Film Formation for Lithography]

A circuit pattern formation method using the composition for underlayer film formation for lithography of the present embodiment has the steps of: forming an underlayer film on a substrate using the composition for underlayer film formation for lithography of the present embodiment (step (B-1)); forming an intermediate layer film on the underlayer film using a resist intermediate layer film material containing a silicon atom (step (B-2)); forming at least one photoresist layer on the intermediate layer film (step (B-3)); after the step (B-3), irradiating a predetermined region of the photoresist layer with radiation for development, thereby forming a resist pattern (step (B-4)); after the step (B-4), etching the intermediate layer film with the resist pattern as a mask, thereby forming an intermediate layer film pattern (step (B-5)); etching the underlayer film with the obtained intermediate layer film pattern as an etching mask, thereby forming a underlayer film pattern (step (B-6)); and etching the substrate with the obtained underlayer film pattern as an etching mask, thereby forming a pattern on the substrate (step (B-7)).

The underlayer film for lithography of the present embodiment is not particularly limited by its formation method as long as it is formed from the composition for underlayer film formation for lithography of the present embodiment. A publicly known approach can be applied thereto. The underlayer film can be formed by, for example, applying the composition for underlayer film formation for lithography of the present embodiment onto a substrate by a publicly known coating method or printing method such as spin coating or screen printing, and then removing an organic solvent by volatilization or the like.

It is preferable to perform baking in the formation of the underlayer film, for preventing a mixing event with an upper layer resist while accelerating crosslinking reaction. In this case, the baking temperature is not particularly limited and is preferably in the range of 80 to 450° C., and more preferably 200 to 400° C. The baking time is not particularly limited and is preferably in the range of 10 to 300 seconds. The thickness of the underlayer film can be arbitrarily selected according to required performance and is not particularly limited, but is usually preferably about 30 to 20,000 nm, and more preferably 50 to 15,000 nm.

After preparing the underlayer film, it is preferable to prepare a silicon-containing resist layer or a usual single-layer resist made of hydrocarbon thereon in the case of a two-layer process, and to prepare a silicon-containing intermediate layer thereon and further a silicon-free single-layer resist layer thereon in the case of a three-layer process. In this case, a publicly known photoresist material can be used for forming this resist layer.

After preparing the underlayer film on the substrate, in the case of a two-layer process, a silicon-containing resist layer or a usual single-layer resist made of hydrocarbon can be prepared on the underlayer film. In the case of a three-layer process, a silicon-containing intermediate layer can be prepared on the underlayer film, and a silicon-free single-layer resist layer can be further prepared on the silicon-containing intermediate layer. In these cases, a publicly known photoresist material can be arbitrarily selected and used for forming the resist layer, without particular limitations.

For the silicon-containing resist material for a two-layer process, a silicon atom-containing polymer such as a polysilsesquioxane derivative or a vinylsilane derivative is used as a base polymer, and a positive type photoresist material further containing an organic solvent, an acid generating agent, and if required, a basic compound or the like is preferably used, from the viewpoint of oxygen gas etching resistance. Herein, a publicly known polymer that is used in this kind of resist material can be used as the silicon atom-containing polymer.

A polysilsesquioxane-based intermediate layer is preferably used as the silicon-containing intermediate layer for a three-layer process. By imparting effects as an antireflection film to the intermediate layer, there is a tendency that reflection can be effectively suppressed. For example, use of a material containing a large amount of an aromatic group and having high substrate etching resistance as the underlayer film in a process for exposure at 193 nm tends to increase a k value and enhance substrate reflection. However, the intermediate layer suppresses the reflection so that the substrate reflection can be 0.5% or less. The intermediate layer having such an antireflection effect is not limited, and polysilsesquioxane that closslinks by an acid or heat in which a light absorbing group having a phenyl group or a silicon-silicon bond is introduced is preferably used for exposure at 193 nm.

Alternatively, an intermediate layer formed by chemical vapour deposition (CVD) may be used. The intermediate layer highly effective as an antireflection film prepared by CVD is not limited, and, for example, a SiON film is known. In general, the formation of an intermediate layer by a wet process such as spin coating or screen printing is more convenient and more advantageous in cost, as compared with CVD. The upper layer resist for a three-layer process may be positive type or negative type, and the same as a single-layer resist generally used can be used.

The underlayer film according to the present embodiment can also be used as an antireflection film for usual single-layer resists or an underlying material for suppression of pattern collapse. The underlayer film of the present embodiment is excellent in etching resistance for an underlying process and can be expected to also function as a hard mask for an underlying process.

In the case of forming a resist layer from the above photoresist material, a wet process such as spin coating or screen printing is preferably used, as in the case of forming the above underlayer film. After coating with the resist material by spin coating or the like, prebaking is generally performed. This prebaking is preferably performed at 80 to 180° C. in the range of 10 to 300 seconds. Then, exposure, post-exposure baking (PEB), and development can be performed according to a conventional method to obtain a resist pattern. The thickness of the resist film is not particularly limited and is generally preferably 30 to 500 nm, and more preferably 50 to 400 nm.

The exposure light can be arbitrarily selected and used according to the photoresist material to be used. General examples thereof can include a high energy ray having a wavelength of 300 nm or less, specifically, excimer laser of 248 nm, 193 nm, or 157 nm, soft x-ray of 3 to 20 nm, electron beam, and X-ray.

In a resist pattern formed by the above method, pattern collapse is suppressed by the underlayer film according to the present embodiment. Therefore, use of the underlayer film according to the present embodiment can produce a finer pattern and can reduce an exposure amount necessary for obtaining the resist pattern.

Next, etching is performed with the obtained resist pattern as a mask. Gas etching is preferably used as the etching of the underlayer film in a two-layer process. The gas etching is preferably etching using oxygen gas. In addition to oxygen gas, an inert gas such as He or Ar, or CO, $CO_2$, $NH_3$, $SO_2$, $N_2$, $NO_2$, or $H_2$ gas may be added. Alternatively, the gas etching may be performed with CO, $CO_2$, $NH_3$, $N_2$, $NO_2$, or $H_2$ gas without the use of oxygen gas. Particularly, the latter gas is preferably used for side wall protection in order to prevent the undercut of pattern side walls.

On the other hand, gas etching is also preferably used as the etching of the intermediate layer in a three-layer process. The same gas etching as described in the above two-layer process is applicable. Particularly, it is preferable to process the intermediate layer in a three-layer process by using chlorofluorocarbon-based gas and using the resist pattern as a mask. Then, as mentioned above, for example, the underlayer film can be processed by oxygen gas etching with the intermediate layer pattern as a mask.

Herein, in the case of forming an inorganic hard mask intermediate layer film as the intermediate layer, a silicon oxide film, a silicon nitride film, or a silicon oxynitride film (SiON film) is formed by CVD, ALD, or the like. A method for forming the nitride film is not limited, and, for example, a method described in Japanese Patent Laid-Open No. 2002-334869 (Patent Literature 6) or WO2004/066377 (Patent Literature 7) can be used. Although a photoresist film can be formed directly on such an intermediate layer film, an organic antireflection film (BARC) may be formed on the intermediate layer film by spin coating and a photoresist film may be formed thereon.

A polysilsesquioxane-based intermediate layer is preferably used as the intermediate layer. By imparting effects as an antireflection film to the resist intermediate layer film, there is a tendency that reflection can be effectively suppressed. A specific material for the polysilsesquioxane-based intermediate layer is not limited, and, for example, a material described in Japanese Patent Laid-Open No. 2007-226170 (Patent Literature 8) or Japanese Patent Laid-Open No. 2007-226204 (Patent Literature 9) can be used.

The subsequent etching of the substrate can also be performed by a conventional method. For example, the substrate made of $SiO_2$ or SiN can be etched mainly using chlorofluorocarbon-based gas, and the substrate made of p-Si, Al, or W can be etched mainly using chlorine- or bromine-based gas. In the case of etching the substrate with chlorofluorocarbon-based gas, the silicon-containing resist of the two-layer resist process or the silicon-containing intermediate layer of the three-layer process is peeled at the same time with substrate processing. On the other hand, in the case of etching the substrate with chlorine- or bromine-based gas, the silicon-containing resist layer or the silicon-containing intermediate layer is separately peeled and in general, peeled by dry etching using chlorofluorocarbon-based gas after substrate processing.

A feature of the underlayer film according to the present embodiment is that it is excellent in etching resistance of these substrates. The substrate can be arbitrarily selected from publicly known ones and used and is not particularly limited. Examples thereof include Si, α-Si, p-Si, $SiO_2$, SiN, SiON, W, TiN, and Al. The substrate may be a laminate having a film to be processed (substrate to be processed) on a base material (support). Examples of such a film to be processed include various low-k films such as Si, $SiO_2$, SiON, SiN, p-Si, α-Si, W, W—Si, Al, Cu, and Al—Si, and stopper films thereof. A material different from that for the base material (support) is generally used. The thickness of the substrate to be processed or the film to be processed is not particularly limited and is generally preferably about 50 to 10,000 nm, and more preferably 75 to 5,000 nm.

[Method for Purifying Compound and/or Resin]

The method for purifying the compound and/or the resin of the present embodiment comprises the steps of: obtaining a solution (S) by dissolving the compound of the present embodiment and/or the resin of the present embodiment in a solvent; and extracting impurities in the compound and/or the resin by bringing the obtained solution (S) into contact with an acidic aqueous solution (a first extraction step), wherein the solvent used in the step of obtaining the solution (S) contains an organic solvent that does not mix with water.

In the first extraction step, the resin is preferably a resin obtained by a reaction between the compound represented by the above formula (A) and a crosslinking compound. According to the purification method of the present embodiment, the contents of various metals that may be contained as impurities in the compound or the resin having a specific structure described above can be reduced.

More specifically, in the purification method of the present embodiment, the above compound and/or resin is dissolved in an organic solvent that does not mix with water to obtain the solution (S), and further, extraction treatment can be carried out by bringing the solution (S) into contact with an acidic aqueous solution. Thereby, metals contained in the solution (S) containing the compound and/or the resin of the present embodiment are transferred to the aqueous phase, then the organic phase and the aqueous phase are separated, and thus the compound and/or the resin of the present embodiment having a reduced metal content can be obtained.

The compound and/or the resin of the present embodiment used in the purification method of the present embodiment may be alone, or may be a mixture of two or more kinds. Also, the compound and/or the resin of the present embodiment may contain various surfactants, various crosslinking agents, various acid generating agents, various stabilizers, and the like.

The solvent that does not mix with water used in the present embodiment is not particularly limited, but is preferably an organic solvent that is safely applicable to semiconductor manufacturing processes, and specifically it is an organic solvent having a solubility in water at room temperature of less than 30%, and more preferably is an organic solvent having a solubility of less than 20% and particularly preferably less than 10%. The amount of the organic solvent used is preferably 1 to 100 times the mass of the compound and/or the resin of the present embodiment to be used.

Specific examples of the solvent that does not mix with water include, but not limited to, ethers such as diethyl ether and diisopropyl ether; esters such as ethyl acetate, n-butyl acetate, and isoamyl acetate; ketones such as methyl ethyl ketone, methyl isobutyl ketone, ethyl isobutyl ketone, cyclohexanone, cyclopentanone, 2-heptanone, and 2-pentanone; glycol ether acetates such as ethylene glycol monoethyl ether acetate, ethylene glycol monobutyl ether acetate, propylene glycol monomethyl ether acetate (PGMEA), and propylene glycol monoethyl ether acetate; aliphatic hydrocarbons such as n-hexane and n-heptane; aromatic hydrocarbons such as toluene and xylene; and halogenated hydrocarbons such as methylene chloride and chloroform. Among these, toluene, 2-heptanone, cyclohexanone, cyclopentanone, methyl isobutyl ketone, propylene glycol monomethyl ether acetate, ethyl acetate, and the like are preferable, methyl isobutyl ketone, ethyl acetate, cyclohexanone, and propylene glycol monomethyl ether acetate are more preferable, and methyl isobutyl ketone and ethyl acetate are still more preferable. Methyl isobutyl ketone, ethyl acetate, and the like have relatively high saturation solubility for the compound and the resin of the present embodiment and a relatively low boiling point, and it is thus possible to reduce the load in the case of industrially distilling off the solvent and in the step of removing the solvent by drying. These solvents can be each used alone, and can be used as a mixture of two or more kinds.

Examples of the acidic aqueous solution used in the purification method of the present embodiment include, but not particularly limited to, aqueous mineral acid solutions in which inorganic compounds are dissolved in water, and aqueous organic acid solutions in which organic compounds are dissolved in water. Examples of the aqueous mineral acid solutions include, but not particularly limited to, aqueous mineral acid solutions in which one or more types of mineral acids such as hydrochloric acid, sulfuric acid, nitric acid, and phosphoric acid are dissolved in water. Examples of the aqueous organic acid solutions include, but not particularly limited to, aqueous organic acid solutions in which one or more types of organic acids such as acetic acid, propionic acid, oxalic acid, malonic acid, succinic acid, fumaric acid, maleic acid, tartaric acid, citric acid, methanesulfonic acid, phenolsulfonic acid, p-toluenesulfonic acid, and trifluoroacetic acid are dissolved in water. These acidic aqueous solutions can be each used alone, and can be also used as a combination of two or more kinds. Among these acidic aqueous solutions, aqueous solutions of one or more mineral acids selected from the group consisting of hydrochloric acid, sulfuric acid, nitric acid, and phosphoric acid, or aqueous solutions of one or more organic acids selected from the group consisting of acetic acid, propionic acid, oxalic acid, malonic acid, succinic acid, fumaric acid, maleic acid, tartaric acid, citric acid, methanesulfonic acid, phenolsulfonic acid, p-toluenesulfonic acid, and trifluoroacetic acid are preferable, aqueous solutions of sulfuric acid, nitric acid, and carboxylic acids such as acetic acid, oxalic acid, tartaric acid, and citric acid are more preferable, aqueous solutions of sulfuric acid, oxalic acid, tartaric acid, and citric acid are still more preferable, and an aqueous solution of oxalic acid is further preferable. It is considered that polyvalent carboxylic acids such as oxalic acid, tartaric acid, and citric acid coordinate with metal ions and provide a chelating effect, and thus tend to be capable of more effectively removing metals. As for water used herein, it is preferable to use water, the metal content of which is small, such as ion exchanged water, according to the purpose of the purification method of the present embodiment.

The pH of the acidic aqueous solution used in the purification method of the present embodiment is not particularly limited, but it is preferable to regulate the acidity of the aqueous solution in consideration of an influence on the compound and/or the resin of the present embodiment. Normally, the pH range is about 0 to 5, and is preferably about pH 0 to 3.

The amount of the acidic aqueous solution used in the purification method of the present embodiment is not particularly limited, but it is preferable to regulate the amount from the viewpoint of reducing the number of extraction operations for removing metals and from the viewpoint of ensuring operability in consideration of the overall amount of fluid. From the above viewpoints, the amount of the acidic aqueous solution used is preferably 10 to 200% by mass, more preferably 20 to 100% by mass, based on 100% by mass of the solution (S).

In the purification method of the present embodiment, by bringing an acidic aqueous solution as described above into contact with the solution (S) containing the compound and/or the resin of the present embodiment and the solvent that does not mix with water, metals can be extracted from the compound or the resin in the solution (S).

In the purification method of the present embodiment, it is preferable that the solution (S) further contains an organic solvent that mixes with water. When an organic solvent that mixes with water is contained, there is a tendency that the amount of the compound and/or the resin of the present embodiment charged can be increased, also the fluid separability is improved, and purification can be carried out at a high reaction vessel efficiency. The method for adding the organic solvent that mixes with water is not particularly limited. For example, any of a method involving adding it to the organic solvent-containing solution in advance, a method involving adding it to water or the acidic aqueous solution in advance, and a method involving adding it after bringing the organic solvent-containing solution into contact with water or the acidic aqueous solution. Among these, the method involving adding it to the organic solvent-containing solution in advance is preferable in terms of the workability of operations and the ease of managing the amount.

The organic solvent that mixes with water used in the purification method of the present embodiment is not particularly limited, but is preferably an organic solvent that is safely applicable to semiconductor manufacturing processes. The amount of the organic solvent used that mixes with water is not particularly limited as long as the solution phase and the aqueous phase separate, but is preferably 0.1 to 100 times, more preferably 0.1 to 50 times, and further preferably 0.1 to 20 times the mass of the compound and/or the resin of the present embodiment.

Specific examples of the organic solvent used in the purification method of the present embodiment that mixes with water include, but not limited to, ethers such as tetrahydrofuran and 1,3-dioxolane; alcohols such as methanol, ethanol, and isopropanol; ketones such as acetone and N-methylpyrrolidone; aliphatic hydrocarbons such as glycol ethers such as ethylene glycol monoethyl ether, ethylene glycol monobutyl ether, propylene glycol monomethyl ether (PGME), and propylene glycol monoethyl ether. Among these, N-methylpyrrolidone, propylene glycol monomethyl ether, and the like are preferable, and N-methylpyrrolidone and propylene glycol monomethyl ether are more preferable. These solvents can be each used alone, and can be used as a mixture of two or more kinds.

The temperature when extraction treatment is carried out is generally in the range of 20 to 90° C., and preferably 30 to 80° C. The extraction operation is carried out, for example, by thoroughly mixing the solution (S) and the acidic aqueous solution by stirring or the like and then leaving the obtained mixed solution to stand still. Thereby, metals contained in the solution containing the compound and/or the resin of the present embodiment and the organic solvents are transferred to the aqueous phase. Also, by this operation, the acidity of the solution is lowered, and the degradation of the compound and/or the resin of the present embodiment can be suppressed.

By being left to stand still, the mixed solution is separated into an aqueous phase and a solution phase containing the compound and/or the resin of the present embodiment and the solvents, and thus the solution phase containing the compound and/or the resin of the present embodiment and the solvents is recovered by decantation. The time for leaving the mixed solution to stand still is not particularly limited, but it is preferable to regulate the time for leaving the mixed solution to stand still from the viewpoint of attaining good separation of the solution phase containing the solvents and the aqueous phase. Normally, the time for leaving the mixed solution to stand still is 1 minute or longer, preferably 10 minutes or longer, and more preferably 30 minutes or longer. While the extraction treatment may be carried out once, it is effective to repeat mixing, leaving-to-stand-still, and separating operations multiple times.

It is preferable that the purification method of the present embodiment includes the step of extracting impurities in the compound or the resin by further bringing the solution phase containing the compound or the resin into contact with water after the first extraction step (the second extraction step). Specifically, for example, it is preferable that after the above extraction treatment is carried out using an acidic aqueous solution, the solution phase that is extracted and recovered from the aqueous solution and that contains the compound and/or the resin of the present embodiment and the solvents is further subjected to extraction treatment with water. The above extraction treatment with water is not particularly limited, and can be carried out, for example, by thoroughly mixing the solution phase and water by stirring or the like and then leaving the obtained mixed solution to stand still. The mixed solution after being left to stand still is separated into an aqueous phase and a solution phase containing the compound and/or the resin of the present embodiment and the solvents, and thus the solution phase containing the compound and/or the resin of the present embodiment and the solvents can be recovered by decantation.

Water used herein is preferably water, the metal content of which is small, such as ion exchanged water, according to the purpose of the present embodiment. While the extraction treatment may be carried out once, it is effective to repeat mixing, leaving-to-stand-still, and separating operations multiple times. The proportions of both used in the extraction treatment and temperature, time, and other conditions are not particularly limited, and may be the same as those of the previous contact treatment with the acidic aqueous solution.

Water that is possibly present in the thus-obtained solution containing the compound and/or the resin of the present embodiment and the solvents can be easily removed by performing vacuum distillation or a like operation. Also, if required, the concentration of the compound and/or the resin of the present embodiment can be regulated to be any concentration by adding a solvent to the solution.

The method for isolating the compound and/or the resin of the present embodiment from the obtained solution containing the compound and/or the resin of the present embodiment and the solvents is not particularly limited, and publicly known methods can be carried out, such as reduced-pressure removal, separation by reprecipitation, and a combination thereof. Publicly known treatments such as concentration operation, filtration operation, centrifugation operation, and drying operation can be carried out if required.

EXAMPLES

The embodiment of the present invention will be more specifically described with reference to examples below. However, the present embodiment is not particularly limited to these examples.

Methods for evaluating a compound are as follows.

Measurement of Thermal Decomposition Temperature

EXSTAR 6000 DSC apparatus manufactured by SII NanoTechnology Inc. was used. About 5 mg of a sample was placed in an unsealed container made of aluminum, and the temperature was raised to 500° C. at a temperature increase rate of 10° C./min in a nitrogen gas stream (30 ml/min). The temperature at which a decrease in baseline appeared was defined as the thermal decomposition temperature.

Synthesis Example 1

To a container (internal capacity: 100 ml) equipped with a stirrer, a condenser tube, and a burette, 3.20 g (20 mmol) of 2,6-naphthalenediol (a reagent manufactured by Sigma-Aldrich) and 1.82 g (10 mmol) of 4-biphenylcarboxyaldehyde (manufactured by Mitsubishi Gas Chemical Company Inc.) were added with 30 ml of methyl isobutyl ketone, then 5 ml of 95% sulfuric acid was added, and the reaction solution was stirred at 100° C. for 6 hours and reacted. Next, the reaction solution was concentrated. The reaction product was precipitated by the addition of 50 g of pure water. After cooling to room temperature, the precipitates were separated by filtration. The obtained solid matter was subjected to filtration, dried, and then separated and purified by column chromatography to obtain 3.05 g of the objective compound represented by the following formula (3).

By 400 MHz-$^1$H-NMR, the compound was confirmed to have a chemical structure of the following formula (3).

$^1$H-NMR: (d-DMSO, internal standard TMS)

δ (ppm) 9.7 (2H, O—H), 7.2-8.5 (19H, Ph-H), 6.6 (1H, C—H)

That the substituted position of 2,6-naphthalenediol was 1-position was confirmed from the signals of the protons at 3-position and 4-position being doublet.

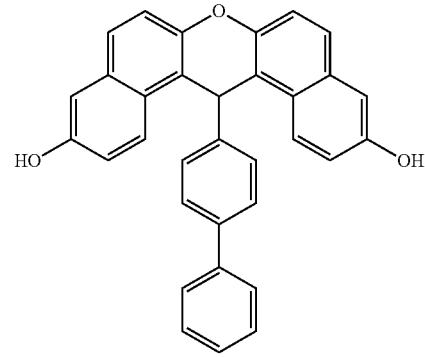

(3)

Synthesis Example 2

To a container (internal capacity: 300 ml) equipped with a stirrer, a condenser tube, and a burette, after 10 g (69.0 mmol) of 2-naphthol (a reagent manufactured by Sigma-Aldrich) was melted at 120° C., 0.27 g of sulfuric acid was added, and 2.7 g (13.8 mmol) of 4-acetylbiphenyl (a reagent manufactured by Sigma-Aldrich) was added, and the contents were reacted by being stirred at 120° C. for 6 hours to obtain a reaction solution. Next, 100 mL of N-methyl-2-pyrrolidone (manufactured by Kanto Chemical Co., Inc.) and 50 mL of pure water were added to the reaction solution and then extracted by ethyl acetate. Next, the mixture was separated until neutral by the addition of pure water, and then concentrated to obtain a solution.

The obtained solution was separated by column chromatography to obtain 1.0 g of the objective compound (BiN-1) represented by the following formula (BiN-1).

As a result of measuring the molecular weight of the obtained compound (BiN-1) by the above method, it was 466. The carbon concentration was 87.5% by mass, and the oxygen concentration was 6.9% by mass.

The following peaks were found by NMR measurement performed on the obtained compound (BiN-1) under the above measurement conditions, and the compound was confirmed to have a chemical structure of the following formula (BiN-1).

δ (ppm) 9.69 (2H, O—H), 7.01-7.67 (21H, Ph-H), 2.28 (3H, C—H)

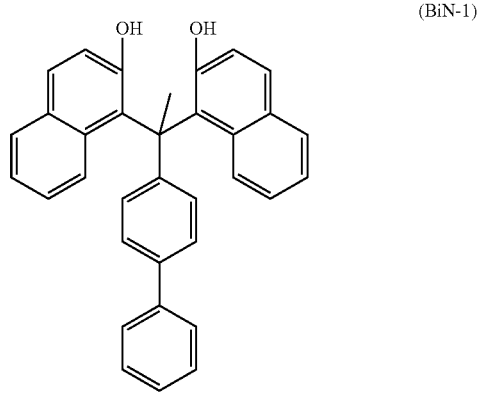 [SMILES: CC(c1ccc(-c2ccccc2)cc1)(c1c(O)ccc2ccccc12)c1c(O)ccc2ccccc12]

(BiN-1)

Synthesis Example 3

To a container (internal capacity: 100 ml) equipped with a stirrer, a condenser tube, and a burette, 3.20 g (20 mmol) of 2,6-naphthalenediol (a reagent manufactured by Sigma-Aldrich) and 1.82 g (10 mmol) of 4-biphenylcarboxyaldehyde (manufactured by Mitsubishi Gas Chemical Company Inc.) were added with 30 ml of methyl isobutyl ketone, then 5 ml of 95% sulfuric acid was added, and the reaction solution was stirred at 100° C. for 3 hours and reacted. Next, the reaction solution was concentrated. The reaction product was precipitated by the addition of 50 g of pure water. After cooling to room temperature, the precipitates were separated by filtration. The obtained solid matter was subjected to filtration, dried, and then separated and purified by column chromatography to obtain 1.0 g of the objective compound (BiN-2) represented by the following formula (BiN-2).

By 400 MHz-¹H-NMR, the compound was confirmed to have a chemical structure of the following formula (BiN-2).

¹H-NMR: (d-DMSO, internal standard TMS)

δ (ppm) 9.7 (2H, O—H), 7.2-8.5 (19H, Ph-H), 6.6 (1H, C—H)

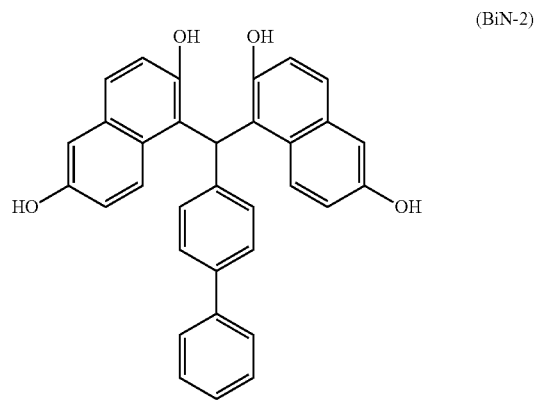 [SMILES: Oc1ccc2c(C(c3ccc(-c4ccccc4)cc3)c3c(O)ccc4cc(O)ccc34)c(O)ccc2c1]

(BiN-2)

Example 1

To a container (internal capacity: 200 ml) equipped with a stirrer, a condenser tube, and a burette, 5.8 g (12.4 mmol) of the compound represented by the above formula (3) and 4 g (28 mmol) of potassium carbonate were added with 100 ml of acetone, then 2.8 g (27 mmol) of methacryloyl chloride and 0.8 g of 10-crown-6 were added, and the reaction solution was stirred under reflux for 7 hours and reacted. Next, the reaction solution was cooled in an ice bath and concentrated. The precipitated solid matter was subjected to filtration, dried, and then separated and purified by column chromatography to obtain 2.0 g of the objective compound represented by the following formula (4).

By 400 MHz-¹H-NMR, the compound was confirmed to have a chemical structure of the following formula (4).

¹H-NMR: (d-DMSO, internal standard TMS)

δ (ppm) 7.2-7.8 (19H, Ph-H), 6.7 (1H, C—H), 5.6-6.0 (4H, —C(CH₃)=CH₂), 1.9 (6H, —C(CH₃)=CH₂)

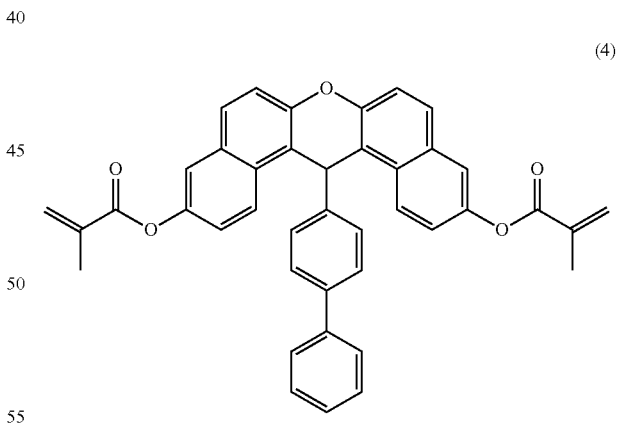

(4)

The thermal decomposition temperature of the obtained compound was 385° C., and high heat resistance was able to be confirmed.

Example 2

The same operations as in Example 1 were performed except that 2.8 g (28 mol) of acryloyl chloride was used instead of methacryloyl chloride, to obtain 1.8 g of the objective compound represented by the following formula (7).

By 400 MHz-$^1$H-NMR, the compound was confirmed to have a chemical structure of the following formula (7).

$^1$H-NMR: (d-DMSO, internal standard TMS)

δ (ppm) 7.2-7.8 (19H, Ph-H), 6.7 (1H, C—H), 5.9-6.3 (6H, —CH=CH$_2$)

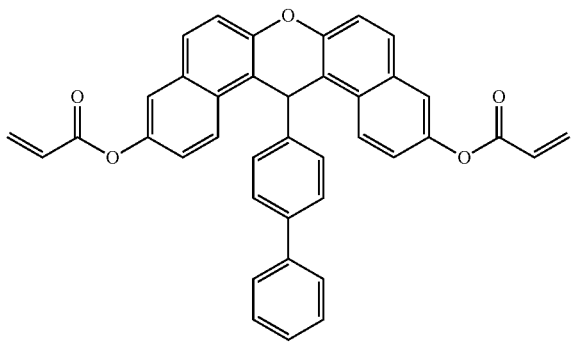

(7)

The thermal decomposition temperature of the obtained compound was 385° C., and high heat resistance was able to be confirmed.

Example 3

To a container (internal capacity: 200 ml) equipped with a stirrer, a condenser tube, and a burette, 5.8 g (12.4 mmol) of the compound represented by the above formula (BiN-1) and 4 g (28 mmol) of potassium carbonate were added with 100 ml of acetone, then 2.8 g (27 mmol) of methacryloyl chloride and 0.8 g of 10-crown-6 were added, and the reaction solution was stirred under reflux for 7 hours and reacted. Next, the reaction solution was cooled in an ice bath and concentrated. The precipitated solid matter was subjected to filtration, dried, and then separated and purified by column chromatography to obtain 2.0 g of the objective compound represented by the following formula (12).

By 400 MHz-$^1$H-NMR, the compound was confirmed to have a chemical structure of the following formula (12).

$^1$H-NMR: (d-DMSO, internal standard TMS)

δ (ppm) 7.16-8.02 (21H, Ph-H), 2.54 (3H, C—H), 6.18-6.43 (4H, —C(CH$_3$)=CH$_2$), 2.0 (6H, —C(CH$_3$)=CH$_2$)

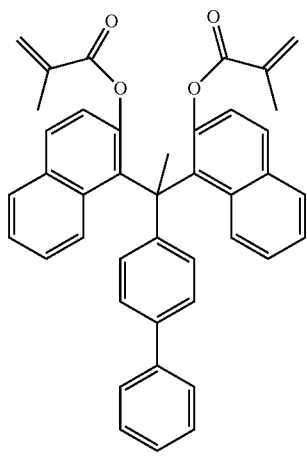

(12)

The thermal decomposition temperature of the obtained compound was 384° C., and high heat resistance was able to be confirmed.

Example 4

The same operations as in Example 3 were performed except that 2.8 g (28 mol) of acryloyl chloride was used instead of methacryloyl chloride, to obtain 1.8 g of the objective compound represented by the following formula (13).

By 400 MHz-$^1$H-NMR, the compound was confirmed to have a chemical structure of the following formula (13).

$^1$H-NMR: (d-DMSO, internal standard TMS)

δ (ppm) 7.23-8.09 (21H, Ph-H), 2.54 (3H, C—H), 5.74-6.24 (4H, —C(CH$_3$)=CH$_2$), 6.1 (6H, —C(CH$_3$)=CH$_2$)

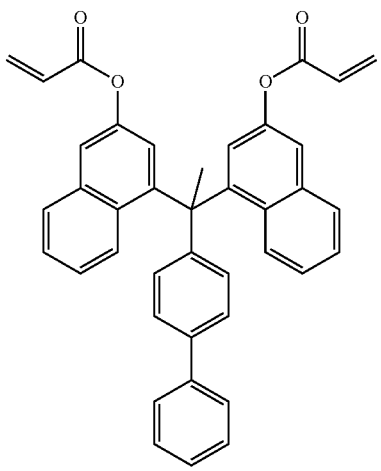

(13)

The thermal decomposition temperature of the obtained compound was 384° C., and high heat resistance was able to be confirmed.

Example 5

To a container (internal capacity: 200 ml) equipped with a stirrer, a condenser tube, and a burette, 5.8 g (12.4 mmol) of the compound represented by the above formula (BiN-2) and 4 g (28 mmol) of potassium carbonate were added with 100 ml of acetone, then 2.8 g (27 mmol) of methacryloyl chloride and 0.8 g of 10-crown-6 were added, and the reaction solution was stirred under reflux for 7 hours and reacted. Next, the reaction solution was cooled in an ice bath and concentrated. The precipitated solid matter was subjected to filtration, dried, and then separated and purified by column chromatography to obtain 2.0 g of the objective compound represented by the following formula (14).

By 400 MHz-$^1$H-NMR, the compound was confirmed to have a chemical structure of the following formula (14).

$^1$H-NMR: (d-DMSO, internal standard TMS)

δ (ppm) 6.9-7.75 (19H, Ph-H), 5.48 (1H, C—H), 6.18-6.43 (8H, —C(CH$_3$)=CH$_2$), 2.0 (12H, —C(CH$_3$)=CH$_2$)

(14)

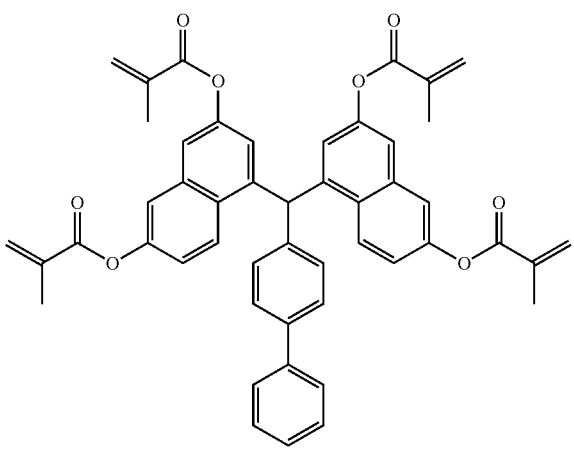

The thermal decomposition temperature of the obtained compound was 385° C., and high heat resistance was able to be confirmed.

Example 6

The same operations as in Example 5 were performed except that 2.8 g (28 mol) of acryloyl chloride was used instead of methacryloyl chloride, to obtain 1.8 g of the objective compound represented by the following formula (15).

By 400 MHz-$^1$H-NMR, the compound was confirmed to have a chemical structure of the following formula (15).

$^1$H-NMR: (d-DMSO, internal standard TMS)

δ (ppm) 6.94-7.75 (19H, Ph-H), 5.48 (1H, C—H), 5.74-6.24 (8H, —C(CH$_3$)=CH$_2$), 6.1 (12H, —C(CH$_3$)=CH$_2$)

(15)

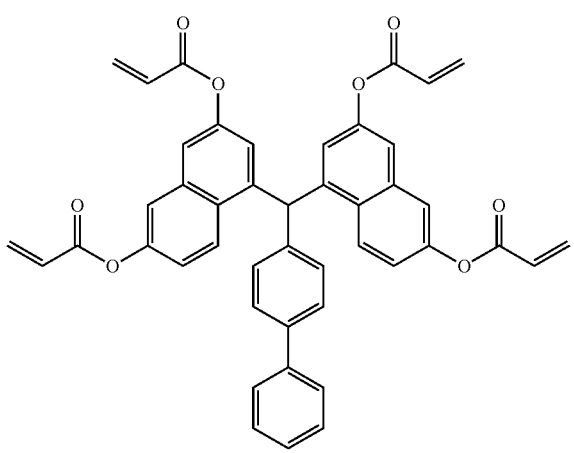

The thermal decomposition temperature of the obtained compound was 385° C., and high heat resistance was able to be confirmed.

Comparative Example 1

A four necked flask (internal capacity: 10 L) equipped with a Dimroth condenser tube, a thermometer, and a stirring blade and having a detachable bottom was prepared. To this four necked flask, 1.09 kg (7 mol) of 1,5-dimethylnaphthalene (manufactured by Mitsubishi Gas Chemical Company, Inc.), 2.1 kg (28 mol as formaldehyde) of 40% by mass of an aqueous formalin solution (manufactured by Mitsubishi Gas Chemical Company, Inc.), and 0.97 mL of 98% by mass of sulfuric acid (manufactured by Kanto Chemical Co., Inc.) were added in a nitrogen stream, and the mixture was reacted for 7 hours while refluxed at 100° C. at normal pressure. Subsequently, 1.8 kg of ethylbenzene (special grade reagent manufactured by Wako Pure Chemical Industries, Ltd.) was added as a diluting solvent to the reaction solution, and the mixture was left to stand still, followed by removal of an aqueous phase as a lower phase. Neutralization and washing with water were further performed, and ethylbenzene and unreacted 1,5-dimethylnaphthalene were distilled off under reduced pressure to obtain 1.25 kg of a light brown solid dimethylnaphthalene formaldehyde resin.

Subsequently, a four necked flask (internal capacity: 0.5 L) equipped with a Dimroth condenser tube, a thermometer, and a stirring blade was prepared. To this four necked flask, 100 g (0.51 mol) of the dimethylnaphthalene formaldehyde resin thus obtained, and 0.05 g of p-toluenesulfonic acid were added in a nitrogen stream, and the temperature was raised to 190° C. at which the mixture was then heated for 2 hours, followed by stirring. Subsequently, 52.0 g (0.36 mol) of 1-naphthol was added thereto, and the temperature was further raised to 220° C. at which the mixture was reacted for 2 hours. After solvent dilution, neutralization and washing with water were performed, and the solvent was removed under reduced pressure to obtain 126.1 g of a black-brown solid modified resin (CR-1).

Examples 1 to 6 and Comparative Example 1

(Heat Resistance and Resist Performance)

Results of conducting heat resistance test and resist performance evaluation using the compounds of the formula (4), the formula (7), the formula (12), the formula (13), the formula (14), and the formula (15), and CR-1 are shown in Table 1.

(Preparation of Resist Composition)

A resist composition was prepared according to the recipe shown in Table 1 using each compound synthesized as described above. Among the components of the resist composition in Table 1, the following acid generating agent (C), acid diffusion controlling agent (E), and solvent were used.

Acid Generating Agent(C)

P-1: triphenylbenzenesulfonium trifluoromethanesulfonate (Midori Kagaku Co., Ltd.) Acid diffusion controlling agent(E)

Q-1: trioctylamine (Tokyo Kasei Kogyo Co., Ltd.) Solvent

S-1: propylene glycol monomethyl ether (Tokyo Kasei Kogyo Co., Ltd.)

(Method for Testing Heat Resistance)

EXSTAR 6000 DSC apparatus manufactured by SII NanoTechnology Inc. was used. About 5 mg of a sample was placed in an unsealed container made of aluminum, and the temperature was raised to 500° C. at a temperature increase rate of 10° C./min in a nitrogen gas stream (30 ml/min). The temperature at which a decrease in baseline appeared was defined as the thermal decomposition temperature (Tg). The heat resistance was evaluated according to the following criteria.

Evaluation A: The thermal decomposition temperature was ≥150° C.

Evaluation C: The thermal decomposition temperature was <150° C.

(Method for Evaluating Resist Performance of Resist Composition)

A clean silicon wafer was spin coated with the homogeneous resist composition, and then prebaked (PB) before exposure in an oven of 110° C. to form a resist film with a thickness of 60 nm. The obtained resist film was irradiated with electron beams of 1:1 line and space setting with a 50 nm interval using an electron beam lithography system (ELS-7500 manufactured by ELIONIX INC.). After irradiation, the resist film was heated at each predetermined temperature for 90 seconds, and immersed in 2.38% by mass TMAH alkaline developing solution for 60 seconds for development. Subsequently, the resist film was washed with ultrapure water for 30 seconds, and dried to form a positive type resist pattern. Concerning the formed resist pattern, the line and space were observed by a scanning electron microscope (S-4800 manufactured by Hitachi High-Technologies Corporation) to evaluate the reactivity by electron beam irradiation of the resist composition.

TABLE 1

| | | Heat resistance evaluation | Resist composition | | | | |
|---|---|---|---|---|---|---|---|
| | Compound | | Compound of synthesis example [g] | P-1 [g] | Q-1 [g] | S-1 [g] | Resist performance evaluation |
| Example 1 | Formula (4) | A | 1.0 | 0.3 | 0.03 | 50.0 | Good |
| Example 2 | Formula (7) | A | 1.0 | 0.3 | 0.03 | 50.0 | Good |
| Example 3 | Formula (12) | A | 1.0 | 0.3 | 0.03 | 50.0 | Good |
| Example 4 | Formula (13) | A | 1.0 | 0.3 | 0.03 | 50.0 | Good |
| Example 5 | Formula (14) | A | 1.0 | 0.3 | 0.03 | 50.0 | Good |
| Example 6 | Formula (15) | A | 1.0 | 0.3 | 0.03 | 50.0 | Good |
| Comparative Example 1 | CR-1 | C | 1.0 | 0.3 | 0.03 | 50.0 | Poor |

TABLE 2

| | Composition | | |
|---|---|---|---|
| | Component (A) [g] | Optically active compound (B) [g] | Solvent [g] |
| Example 7 | Formula (4) 0.5 | B-1 1.5 | S-1 30.0 |
| Example 8 | Formula (7) 0.5 | B-1 1.5 | S-1 30.0 |
| Example 9 | Formula (12) 0.5 | B-1 1.5 | S-1 30.0 |
| Example 10 | Formula (13) 0.5 | B-1 1.5 | S-1 30.0 |
| Example 11 | Formula (14) 0.5 | B-1 1.5 | S-1 30.0 |
| Example 12 | Formula (15) 0.5 | B-1 1.5 | S-1 30.0 |
| Comparative Example 2 | PHS-1 0.5 | B-1 1.5 | S-1 30.0 |

As is evident from Table 1, it was able to be confirmed that the compounds used in Examples 1, 2, 3, 4, 5, and 6 (the compounds of the formula (4), the formula (7), the formula (12), the formula (13), the formula (14), and the formula (15), respectively) have good heat resistance whereas the compound (CR-1) used in Comparative Example 1 is inferior in heat resistance.

In resist pattern evaluation, a good resist pattern was obtained by irradiation with electron beams of 1:1 line and space setting with a 50 nm interval in Examples 1, 2, 3, 4, 5, and 6. On the other hand, no good resist pattern was able to be obtained in Comparative Example 1.

Thus, the compound that satisfies the requirements of the present invention has high heat resistance and can impart a good shape to a resist pattern, as compared with the comparative compound (CR-1). As long as the above requirements of the present invention are met, compounds other than those described in Examples also exhibit the same effects.

Examples 7 to 12 and Comparative Example 2

(Preparation of Radiation-Sensitive Composition)

The components set forth in Table 2 were prepared and formed into homogeneous solutions, and the obtained homogeneous solutions were filtered through a Teflon® membrane filter with a pore diameter of 0.1 μm to prepare radiation-sensitive compositions. Each prepared radiation-sensitive composition was evaluated as described below.

The following resist base material was used in Comparative Example 2.

PHS-1: polyhydroxystyrene Mw=8000 (Sigma-Aldrich)

The following optically active compound (B) was used.

B-1: naphthoquinonediazide-based sensitizing agent of the chemical structural formula (G) (4NT-300, Toyo Gosei Co., Ltd.)

The following solvent was used.

S-1: propylene glycol monomethyl ether (Tokyo Kasei Kogyo Co., Ltd.)

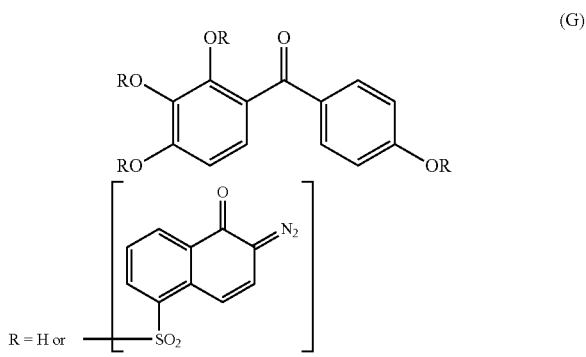

(G)

(Evaluation of Resist Performance of Radiation-Sensitive Composition)

A clean silicon wafer was spin coated with the radiation-sensitive composition obtained as described above, and then prebaked (PB) before exposure in an oven of 110° C. to form a resist film with a thickness of 200 nm. The resist film was exposed to ultraviolet using an ultraviolet exposure apparatus (mask aligner MA-10 manufactured by Mikasa Co., Ltd.). The ultraviolet lamp used was a super high pressure mercury lamp (relative intensity ratio: g-ray:h-ray:i-ray:j-ray=100:80:90:60). After irradiation, the resist film was heated at 110° C. for 90 seconds, and immersed in 2.38% by mass TMAH alkaline developing solution for 60 seconds for development. Subsequently, the resist film was washed with ultrapure water for 30 seconds, and dried to form a 5 μm positive type resist pattern.

The obtained line and space were observed in the formed resist pattern by a scanning electron microscope (S-4800 manufactured by Hitachi High-Technologies Corporation). As for the line edge roughness, a pattern having asperities of less than 50 nm was evaluated as goodness.

In the case of using the radiation-sensitive compositions of Examples 7, 8, 9, 10, 11, and 12, a good resist pattern with a resolution of 5 μm was able to be obtained. The roughness of the pattern was also small and good.

On the other hand, in the case of using the radiation-sensitive composition of Comparative Example 2, a good resist pattern with a resolution of 5 μm was able to be obtained. However, the roughness of the pattern was large and poor.

As described above, it was found that a resist pattern that has small roughness and a good shape can be formed in Examples 7, 8, 9, 10, 11, and 12, as compared with Comparative Example 2. As long as the above requirements of the present invention are met, radiation-sensitive compositions other than those described in Examples also exhibit the same effects.

The compounds obtained in Examples 1, 2, 3, 4, 5, and 6 have a relatively low molecular weight and a low viscosity, and all of their glass transition temperatures are as low as 100° C. or lower. Therefore, the embedding properties of underlayer film forming materials for lithography containing these compounds can be relatively advantageously enhanced. Furthermore, all of their thermal decomposition temperatures are 150° C. or higher (evaluation A), and high heat resistance is retained because of their rigid structures after elimination of acid dissociation groups. Therefore, the materials can be used even under high temperature baking conditions.

Examples 13 to 18 and Comparative Example 3

(Preparation of Composition for Underlayer Film Formation for Lithography)

Compositions for underlayer film formation for lithography were prepared according to the composition shown in Table 3. Next, a silicon substrate was spin coated with each of these compositions for underlayer film formation for lithography, and then baked at 240° C. for 60 seconds and further at 400° C. for 120 seconds to prepare each underlayer film with a film thickness of 200 nm. The following acid generating agent, crosslinking agent, and organic solvent were used.

Acid generating agent: di-tertiary butyl diphenyliodonium nonafluoromethanesulfonate (DTDPI) manufactured by Midori Kagaku Co., Ltd.

Crosslinking agent: NIKALAC MX270 (NIKALAC) (Sanwa Chemical Co., Ltd.)

Organic solvent: propylene glycol monomethyl ether acetate (PGMEA)

Novolac: PSM4357 manufactured by Gunei Chemical Industry Co., Ltd.

Next, etching test was conducted under conditions shown below to evaluate etching resistance. The evaluation results are shown in Table 3.

[Etching Test]

Etching apparatus: RIE-10NR manufactured by Samco International, Inc.

Output: 50 W
Pressure: 20 Pa
Time: 2 min
Etching gas
Ar gas flow rate:$CF_4$ gas flow rate:$O_2$ gas flow rate=50:5:5 (sccm)

(Evaluation of Etching Resistance)

The evaluation of etching resistance was conducted by the following procedures. First, an underlayer film of novolac was prepared under the above conditions except that novolac (PSM4357 manufactured by Gunei Chemical Industry Co., Ltd.) was used. Then, this underlayer film of novolac was subjected to the above etching test, and the etching rate was measured.

Next, underlayer films of Examples 13, 14, 15, 16, 17, and 18 and Comparative Example 3 were prepared under the same conditions as in the underlayer film of novolac, and subjected to the above etching test in the same way as above, and the etching rate was measured.

Then, the etching resistance was evaluated according to the following evaluation criteria on the basis of the etching rate of the underlayer film of novolac.

[Evaluation Criteria]

A: The etching rate was less than −10% as compared with the underlayer film of novolac.

B: The etching rate was −10% to +5% as compared with the underlayer film of novolac.

C: The etching rate was more than +5% as compared with the underlayer film of novolac.

TABLE 3

| | Underlayer film forming material (part by mass) | Solvent (part by mass) | Acid generating agent (part by mass) | Cross-linking agent (part by mass) | Evaluation of etching resistance |
|---|---|---|---|---|---|
| Example 13 | Formula (4) (10) | PGMEA (90) | DTDPI (0.5) | NIKALAC (0.5) | A |
| Example 14 | Formula (7) (10) | PGMEA (90) | DTDPI (0.5) | NIKALAC (0.5) | A |
| Example 15 | Formula (12) (10) | PGMEA (90) | DTDPI (0.5) | NIKALAC (0.5) | A |
| Example 16 | Formula (13) (10) | PGMEA (90) | DTDPI (0.5) | NIKALAC (0.5) | A |
| Example 17 | Formula (14) (10) | PGMEA (90) | DTDPI (0.5) | NIKALAC (0.5) | A |
| Example 18 | Formula (15) (10) | PGMEA (90) | DTDPI (0.5) | NIKALAC (0.5) | A |
| Comparative Example 3 | CR-1 (10) | PGMEA (90) | DTDPI (0.5) | NIKALAC (0.5) | C |

It was found that an excellent etching rate is exerted in Examples 13, 14, 15, 16, 17, and 18 as compared with the underlayer film of novolac.

On the other hand, it was found that an etching rate was poor in Comparative Example 3 as compared with the underlayer film of novolac.

Example 19

Next, a SiO$_2$ substrate with a film thickness of 300 nm was coated with the composition for underlayer film formation for lithography of Example 13, and baked at 240° C. for 60 seconds and further at 400° C. for 120 seconds to form an underlayer film with a film thickness of 85 nm. This underlayer film was coated with a resist solution for ArF and baked at 130° C. for 60 seconds to form a photoresist layer with a film thickness of 140 nm.

The ArF resist solution used was prepared by containing 5 parts by mass of a compound of the formula (16) given below, 1 part by mass of triphenylsulfonium nonafluoromethanesulfonate, 2 parts by mass of tributylamine, and 92 parts by mass of PGMEA.

The compound of the formula (16) was prepared as follows. 4.15 g of 2-methyl-2-methacryloyloxyadamantane, 3.00 g of methacryloyloxy-γ-butyrolactone, 2.08 g of 3-hydroxy-1-adamantyl methacrylate, and 0.38 g of azobisisobutyronitrile were dissolved in 80 mL of tetrahydrofuran to prepare a reaction solution. This reaction solution was polymerized for 22 hours with the reaction temperature kept at 63° C. in a nitrogen atmosphere. Then, the reaction solution was added dropwise into 400 mL of n-hexane. The product resin thus obtained was solidified and purified, and the resulting white powder was filtered and dried overnight at 40° C. under reduced pressure to obtain a compound represented by the following formula.

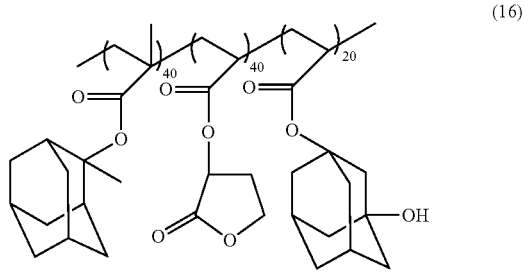

(16)

wherein 40, 40, and 20 represent the ratio of each constituent unit and do not represent a block copolymer.

Subsequently, the photoresist layer was exposed using an electron beam lithography system (manufactured by ELIONIX INC.; ELS-7500, 50 keV), baked (PEB) at 115° C. for 90 seconds, and developed for 60 seconds in 2.38% by mass tetramethylammonium hydroxide (TMAH) aqueous solution to obtain a positive type resist pattern.

Comparative Example 4

The same operations as in Example 19 were performed except that no underlayer film was formed so that a photoresist layer was formed directly on a SiO$_2$ substrate to obtain a positive type resist pattern.

[Evaluation]

Concerning each of Example 19 and Comparative Example 4, the shapes of the obtained 45 nm L/S (1:1) and 80 nm L/S (1:1) resist patterns were observed under an electron microscope manufactured by Hitachi, Ltd. (S-4800). The shapes of the resist patterns after development were evaluated as goodness when having good rectangularity without pattern collapse, and as poorness if this was not the case. The smallest line width having good rectangularity without pattern collapse as a result of this observation was used as an index for resolution evaluation. The smallest electron beam energy quantity capable of lithographing good pattern shapes was used as an index for sensitivity evaluation. The results are shown in Table 4.

TABLE 4

| | Underlayer film forming material | Resolution (nmL/S) | Sensitivity (μC/cm$^2$) | Resist pattern shape after development |
|---|---|---|---|---|
| Example 19 | As described in Example 1 | 47 | 12 | Good |
| Comparative Example 4 | None | 81 | 25 | Poor |

As is evident from Table 4, the underlayer film of Example 19 was confirmed to be significantly superior in both resolution and sensitivity to Comparative Example 4. Also, the resist pattern shapes after development were confirmed to have good rectangularity without pattern collapse. The difference in the resist pattern shapes after development indicated that the underlayer film forming material for lithography of Example 19 has good adhesiveness to a resist material.

Example 20

A SiO$_2$ substrate with a film thickness of 300 nm was coated with the composition for underlayer film formation for lithography used in Example 13, and baked at 240° C. for 60 seconds and further at 400° C. for 120 seconds to form an underlayer film with a film thickness of 90 nm. This underlayer film was coated with a silicon-containing intermediate layer material and baked at 200° C. for 60 seconds to form an intermediate layer film with a film thickness of 35 nm. This intermediate layer film was further coated with the above resist solution for ArF and baked at 130° C. for 60 seconds to form a photoresist layer with a film thickness of 150 nm. The silicon-containing intermediate layer material used was the silicon atom-containing polymer described in <Synthesis Example 1> of Japanese Patent Laid-Open No. 2007-226170.

Subsequently, the photoresist layer was mask exposed using an electron beam lithography system (manufactured by ELIONIX INC.; ELS-7500, 50 keV), baked (PEB) at 115° C. for 90 seconds, and developed for 60 seconds in 2.38% by mass tetramethylammonium hydroxide (TMAH) aqueous solution to obtain a 45 nm L/S (1:1) positive type resist pattern.

Then, the silicon-containing intermediate layer film (SOG) was dry etched with the obtained resist pattern as a mask using RIE-10NR manufactured by Samco International, Inc. Subsequently, dry etching of the underlayer film with the obtained silicon-containing intermediate layer film pattern as a mask and dry etching of the SiO$_2$ film with the obtained underlayer film pattern as a mask were performed in order.

Respective etching conditions are as shown below.

Conditions for Etching of Resist Intermediate Layer Film with Resist Pattern

Output: 50 W

Pressure: 20 Pa

Time: 1 min

Etching gas

Ar gas flow rate:$CF_4$ gas flow rate:$O_2$ gas flow rate=50:8:2 (sccm)

Conditions for Etching of Resist Underlayer Film with Resist Intermediate Film Pattern
Output: 50 W
Pressure: 20 Pa
Time: 2 min
Etching gas
Ar gas flow rate:$CF_4$ gas flow rate:$O_2$ gas flow rate=50:5:5 (sccm)

Conditions for Etching of $SiO_2$ Film with Resist Underlayer Film Pattern
Output: 50 W
Pressure: 20 Pa
Time: 2 min
Etching gas
Ar gas flow rate:$C_5F_{12}$ gas flow rate:$C_2F_6$ gas flow rate:$O_2$ gas flow rate=50:4:3:1 (sccm)

[Evaluation]

The pattern cross section (the shape of the $SiO_2$ film after etching) of Example 20 obtained as described above was observed under an electron microscope manufactured by Hitachi, Ltd. (S-4800). As a result, it was confirmed that the shape of the $SiO_2$ film after etching in a multilayer resist process is a rectangular shape in Examples using the underlayer film of the present invention and is good without defects.

The present application is based on Japanese Patent Application No. 2015-145643 filed on Jul. 23, 2015 with the Japan Patent Office, the contents of which are incorporated herein by reference.

The present invention has industrial applicability as a compound that can be used in photoresist components, resin raw materials for materials for electric or electronic components, raw materials for curable resins such as photocurable resins, resin raw materials for structural materials, or resin curing agents, etc.

The invention claimed is:

1. A (meth)acryloyl compound represented by the following formula (A):

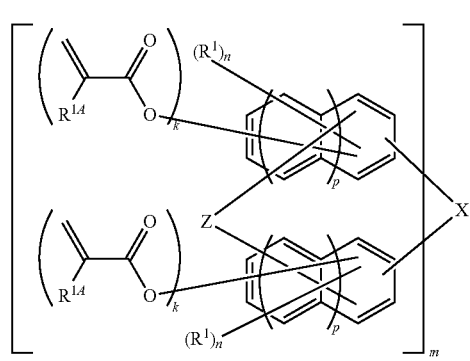

wherein X is a 2m-valent group having 1 to 60 carbon atoms or a single bond; each Z is independently an oxygen atom, a sulfur atom, or not a crosslink; each $R^1$ is independently a linear, branched, or cyclic alkyl group having 1 to 30 carbon atoms, an aryl group having 6 to 30 carbon atoms and optionally having a substituent, an alkenyl group having 2 to 30 carbon atoms and optionally having a substituent, an alkoxy group having 1 to 30 carbon atoms and optionally having a substituent, a halogen atom, a nitro group, an amino group, a carboxylic acid group, a thiol group, a hydroxy group, or a group in which a hydrogen atom of a hydroxy group is replaced with a vinylphenylmethyl group, wherein the alkyl group, the aryl group, the alkenyl group, or the alkoxy group optionally contains an ether bond, a ketone bond, or an ester bond; each $R^{1A}$ is independently a methyl group or a hydrogen atom; each k is independently an integer of 0 to 2, provided that all of the k moieties are not 0 at the same time; m is an integer of 1 to 3; each n is independently an integer of 0 to 5; and each p is independently 0 or 1; and wherein every p is 1, in the above formula (A).

2. The (meth)acryloyl compound according to claim 1, wherein X is a 2m-valent group having 1 to 19 carbon atoms or a single bond, each Z is independently an oxygen atom, a sulfur atom, or not a crosslink, each $R^1$ is independently an alkyl group having 1 to 4 carbon atoms or a halogen atom, each $R^{1A}$ is independently a methyl group or a hydrogen atom, each k is independently an integer of 0 to 2, provided that all of the k moieties are not 0 at the same time, m is an integer of 1 to 3, each n is independently an integer of 0 to 5, and each p is independently 0 or 1, in the above formula (A).

3. The (meth)acryloyl compound according to claim 1, wherein Z is an oxygen atom, in the above formula (A).

4. The (meth)acryloyl compound according to claim 1, wherein Z is not a crosslink, in the above formula (A).

5. The (meth)acryloyl compound according to claim 3, wherein the compound represented by the above formula (A) is a compound represented by the following formula (1):

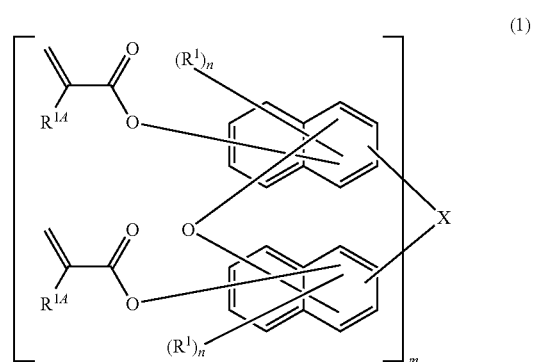

wherein X, $R^1$, $R^{1A}$, m, and n are the same as the groups in the above formula (A).

6. A method for producing the (meth)acryloyl compound according to claim 5, comprising:

a step of reacting a compound represented by the following formula (2) with a (meth)acryloyl group introducing agent in the presence of a basic catalyst:

(2)

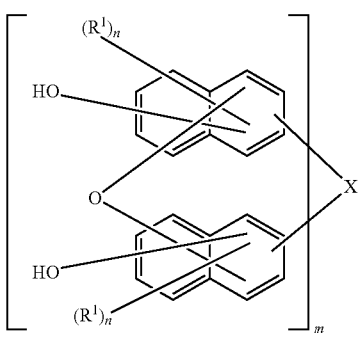

wherein X is a 2m-valent group having 1 to 19 carbon atoms or a single bond; each $R^1$ is independently an alkyl group having 1 to 4 carbon atoms or a halogen atom; m is an integer of 1 to 3; and each n is independently an integer of 0 to 5.

7. The (meth)acryloyl compound according to claim 3, wherein the compound represented by the above formula (A) is a compound represented by the following formula (1'):

(1')

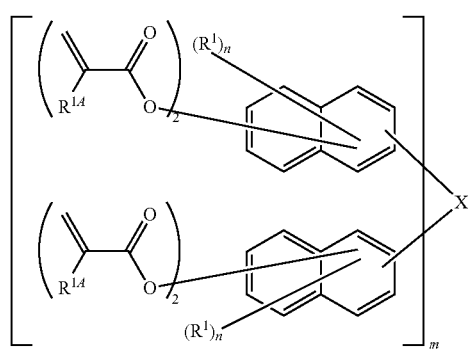

wherein X, $R^1$, $R^{1A}$, m, and n are the same as the groups in the above formula (A).

8. A method for producing the (meth)acryloyl compound according to claim 7, comprising:
a step of reacting a compound represented by the following formula (2') with a (meth)acryloyl group introducing agent in the presence of a basic catalyst:

(2')

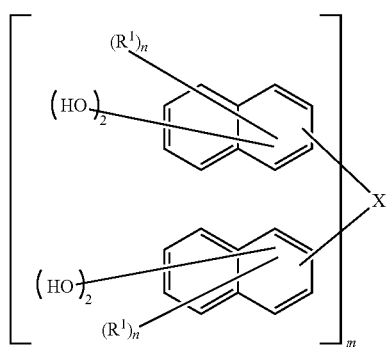

wherein X is a 2m-valent group having 1 to 19 carbon atoms or a single bond; each $R^1$ is independently an alkyl group having 1 to 4 carbon atoms or a halogen atom; m is an integer of 1 to 3; and each n is independently an integer of 0 to 5.

9. The (meth)acryloyl compound according to claim 5, wherein the compound represented by the above formula (1) is a compound represented by the following formula (4) or (7):

(4)

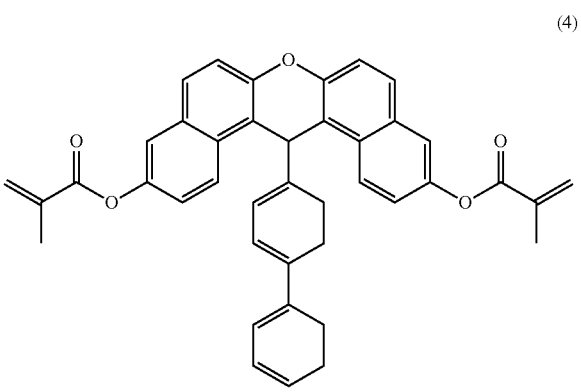

(7)

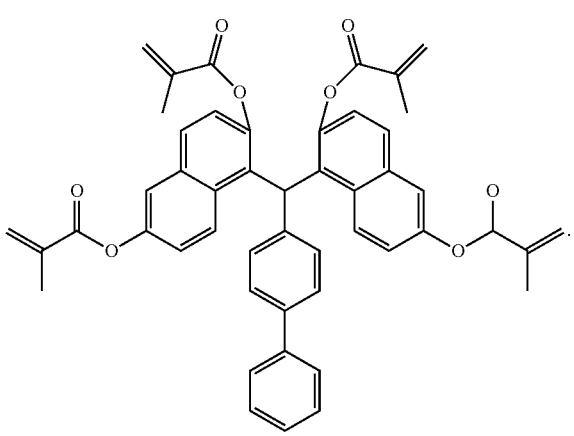

10. The (meth)acryloyl compound according to claim 7, wherein the compound represented by the above formula (1') is a compound represented by the following formula (4'):

(4')

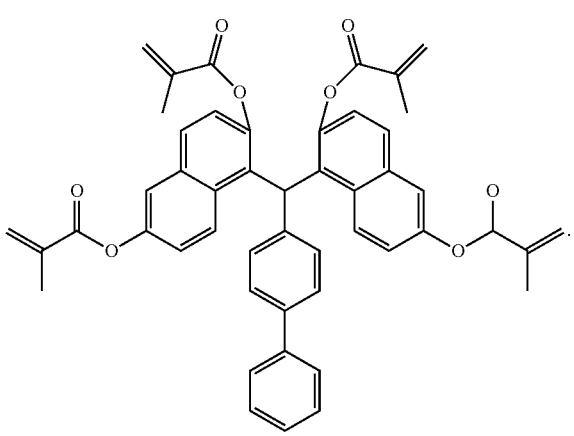

* * * * *